US010912930B2

(12) United States Patent
Warring et al.

(10) Patent No.: US 10,912,930 B2
(45) Date of Patent: Feb. 9, 2021

(54) INTRAVENOUS CATHETER INSERTION DEVICE AND METHOD OF USE

(71) Applicant: Vascular Pathways, Inc., Salt Lake City, UT (US)

(72) Inventors: Jessica A. Warring, Millbrae, CA (US); Amir Belson, Los Altos, CA (US); Winfield S. Fisher, Maple Ridge (CA)

(73) Assignee: Vascular Pathways, Inc., Salt Lake City, UT (US)

( * ) Notice: Subject to any disclaimer, the term of this patent is extended or adjusted under 35 U.S.C. 154(b) by 807 days.

(21) Appl. No.: 14/866,738

(22) Filed: Sep. 25, 2015

(65) Prior Publication Data

US 2016/0015945 A1     Jan. 21, 2016

Related U.S. Application Data

(63) Continuation of application No. 14/250,093, filed on Apr. 10, 2014, which is a continuation of application
(Continued)

(51) Int. Cl.
*A61M 25/09*     (2006.01)
*A61M 25/06*     (2006.01)
(Continued)

(52) U.S. Cl.
CPC .. *A61M 25/09041* (2013.01); *A61M 25/0606* (2013.01); *A61M 25/0631* (2013.01);
(Continued)

(58) Field of Classification Search
CPC ........ A61M 25/0606; A61M 25/09041; A61M 2025/0175; A61M 2025/09116;
(Continued)

(56) References Cited

U.S. PATENT DOCUMENTS 2,211,975 A     8/1940    Hendrickson
2,259,488 A    10/1941    Raiche
(Continued)

FOREIGN PATENT DOCUMENTS

AU       710967 B2    9/1999
CN      1178707 A     4/1998
(Continued)

OTHER PUBLICATIONS

"Torayguide Guidewire". Accessed from <http://www.toray.us/products/medical/med_us001.html> on Oct. 30, 2017.*
(Continued)

*Primary Examiner* — Kami A Bosworth
(74) *Attorney, Agent, or Firm* — Rutan & Tucker LLP

(57) ABSTRACT

A catheter insertion device includes a housing, a needle, a guide wire, and a catheter disposed coaxially over the needle. The needle has a proximal end in the housing and a distal end extending from a distal end of the housing in an insertion position. The guide wire has a distal portion disposed in a lumen of the needle in a withdrawn position. The guide wire may include a safety tip having a non-coiled configuration in the withdrawn position and a coiled configuration in an advanced position. The catheter insertion device may include a sliding member attached to the guide wire, wherein movement of the sliding member translates the guide wire from the withdrawn position to the advanced position.

7 Claims, 28 Drawing Sheets

Related U.S. Application Data

No. 12/307,519, filed as application No. PCT/US2007/068393 on May 7, 2007, now Pat. No. 8,728,035, which is a continuation-in-part of application No. 11/577,491, filed as application No. PCT/US2006/026671 on Jul. 6, 2006, now Pat. No. 9,162,037.

(60) Provisional application No. 60/697,333, filed on Jul. 6, 2005.

(51) Int. Cl.
*A61M 5/32* (2006.01)
*A61M 25/01* (2006.01)

(52) U.S. Cl.
CPC ............ A61M 25/09 (2013.01); *A61M 5/3232* (2013.01); *A61M 5/3234* (2013.01); *A61M 5/3243* (2013.01); *A61M 5/3257* (2013.01); *A61M 25/01* (2013.01); *A61M 25/065* (2013.01); *A61M 2025/09133* (2013.01)

(58) Field of Classification Search
CPC ........ A61M 2025/09125; A61M 25/01; A61M 25/0631; A61M 2025/09133; A61M 2025/09175

See application file for complete search history.

(56) References Cited

U.S. PATENT DOCUMENTS

| | | |
|---|---|---|
| 2,330,400 A | 9/1943 | Hinder |
| D138,589 S | 8/1944 | Brandenburg |
| 3,185,151 A | 5/1965 | Czorny |
| 3,297,030 A | 1/1967 | Czorny et al. |
| 3,416,567 A | 12/1968 | von Dardel et al. |
| 3,469,579 A | 9/1969 | Hubert |
| 3,500,828 A | 3/1970 | Podhora |
| 3,552,384 A | 1/1971 | Pierie et al. |
| 3,572,334 A | 3/1971 | Petterson |
| 3,585,996 A | 6/1971 | Reynolds et al. |
| 3,589,361 A | 6/1971 | Loper et al. |
| 3,592,192 A | 7/1971 | Harautuneian |
| 3,595,230 A | 7/1971 | Suyeoka et al. |
| 3,610,240 A | 10/1971 | Harautuneian |
| 3,682,173 A | 8/1972 | Center |
| 3,884,242 A | 5/1975 | Bazell et al. |
| 3,921,631 A | 11/1975 | Thompson |
| 3,995,628 A | 12/1976 | Gula et al. |
| 4,027,668 A | 6/1977 | Dunn |
| 4,037,600 A | 7/1977 | Poncy et al. |
| 4,079,738 A | 3/1978 | Dunn et al. |
| 4,106,506 A | 8/1978 | Koehn et al. |
| 4,177,809 A | 12/1979 | Moorehead |
| 4,292,970 A | 10/1981 | Hession, Jr. |
| 4,317,445 A | 3/1982 | Robinson |
| 4,345,602 A | 8/1982 | Yoshimura et al. |
| 4,354,491 A | 10/1982 | Marbry |
| 4,368,730 A | 1/1983 | Sharrock |
| 4,387,879 A | 6/1983 | Tauschinski |
| 4,417,886 A | 11/1983 | Frankhouser et al. |
| 4,449,693 A | 5/1984 | Gereg |
| 4,456,017 A | 6/1984 | Miles |
| 4,464,171 A | 8/1984 | Garwin |
| 4,509,534 A | 4/1985 | Tassin, Jr. |
| 4,509,945 A | 4/1985 | Kramann et al. |
| 4,511,359 A | 4/1985 | Vaillancourt |
| 4,512,766 A | 4/1985 | Vailancourt |
| 4,581,019 A | 4/1986 | Curelaru et al. |
| 4,585,440 A | 4/1986 | Tchervenkov et al. |
| D287,877 S | 1/1987 | Holewinski et al. |
| 4,728,322 A | 3/1988 | Walker et al. |
| 4,738,659 A | 4/1988 | Sleiman |
| 4,747,831 A | 5/1988 | Kulli |
| 4,767,407 A | 8/1988 | Foran |
| 4,772,264 A | 9/1988 | Cragg |
| 4,772,267 A | 9/1988 | Brown |
| 4,781,703 A | 11/1988 | Walker et al. |
| 4,792,531 A | 12/1988 | Kakihana |
| 4,798,193 A | 1/1989 | Giesy et al. |
| 4,813,934 A | 3/1989 | Engelson et al. |
| 4,826,070 A | 5/1989 | Kakihana |
| 4,828,547 A | 5/1989 | Sahi et al. |
| 4,834,708 A | 5/1989 | Pillari |
| 4,834,718 A | 5/1989 | McDonald |
| 4,840,613 A | 6/1989 | Balbierz |
| 4,840,622 A | 6/1989 | Hardy |
| 4,842,591 A | 6/1989 | Luther |
| 4,846,812 A | 7/1989 | Walker et al. |
| 4,869,259 A | 9/1989 | Elkins |
| D304,079 S | 10/1989 | McFarlane |
| 4,871,358 A | 10/1989 | Gold |
| 4,874,377 A | 10/1989 | Newgard et al. |
| 4,883,461 A | 11/1989 | Sawyer |
| 4,883,699 A | 11/1989 | Aniuk et al. |
| 4,894,052 A | 1/1990 | Crawford |
| 4,895,346 A | 1/1990 | Steigerwald |
| 4,900,307 A | 2/1990 | Kulli |
| 4,906,956 A | 3/1990 | Kakihana |
| 4,908,021 A | 3/1990 | McFarlane |
| 4,909,793 A | 3/1990 | Vining et al. |
| 4,911,691 A | 3/1990 | Aniuk et al. |
| 4,913,704 A | 4/1990 | Kurimoto |
| 4,917,102 A | 4/1990 | Miller et al. |
| 4,917,671 A | 4/1990 | Chang |
| 4,929,235 A | 5/1990 | Merry et al. |
| 4,935,010 A | 6/1990 | Cox et al. |
| 4,944,725 A | 7/1990 | McDonald |
| 4,944,728 A | 7/1990 | Carrell et al. |
| 4,955,863 A | 9/1990 | Walker et al. |
| 4,961,729 A | 10/1990 | Vaillancourt |
| 4,966,586 A | 10/1990 | Vaillancourt |
| 4,966,589 A | 10/1990 | Kaufman |
| 4,994,042 A | 2/1991 | Vadher |
| 4,994,047 A | 2/1991 | Walker et al. |
| 4,995,866 A | 2/1991 | Amplatz et al. |
| 5,007,901 A | 4/1991 | Shields |
| 5,009,642 A | 4/1991 | Bahl |
| 5,019,048 A | 5/1991 | Margolin |
| 5,019,049 A | 5/1991 | Raining |
| D318,733 S | 7/1991 | Wyzgala |
| 5,034,347 A | 7/1991 | Kakihana |
| 5,047,013 A | 9/1991 | Rossdeutscher |
| D321,250 S | 10/1991 | Jepson et al. |
| 5,053,014 A | 10/1991 | Van Heugten |
| 5,054,501 A * | 10/1991 | Chuttani ............... A61M 25/09 600/585 |
| 5,061,254 A | 10/1991 | Karakelle et al. |
| 5,064,416 A | 11/1991 | Newgard et al. |
| 5,078,694 A | 1/1992 | Wallace |
| 5,078,696 A | 1/1992 | Nedbaluk |
| 5,078,702 A | 1/1992 | Pomeranz |
| 5,084,023 A | 1/1992 | Lemieux |
| 5,085,645 A | 2/1992 | Purdy et al. |
| 5,088,984 A | 2/1992 | Fields |
| 5,093,692 A | 3/1992 | Su et al. |
| 5,098,392 A | 3/1992 | Fleisch Hacker et al. |
| 5,098,395 A | 3/1992 | Fields |
| 5,098,405 A | 3/1992 | Peterson et al. |
| 5,108,375 A | 4/1992 | Harrison et al. |
| 5,108,376 A | 4/1992 | Bonaldo |
| 5,112,312 A | 5/1992 | Luther |
| 5,116,323 A | 5/1992 | Kreuzer et al. |
| 5,120,317 A | 6/1992 | Luther |
| 5,125,906 A | 6/1992 | Fleck |
| 5,135,487 A | 8/1992 | Morrill et al. |
| 5,137,515 A | 8/1992 | Hogan |
| 5,149,326 A | 9/1992 | Woodgrift et al. |
| 5,154,703 A | 10/1992 | Bonaldo |
| 5,156,544 A | 10/1992 | Weinstein |
| 5,156,590 A | 10/1992 | Vilmar |
| 5,156,596 A | 10/1992 | Balbierz et al. |
| 5,158,544 A | 10/1992 | Weinstein |

(56) References Cited

U.S. PATENT DOCUMENTS

| | | |
|---|---|---|
| 5,167,637 A | 12/1992 | Okada |
| 5,176,650 A | 1/1993 | Haining |
| 5,186,168 A | 2/1993 | Spofford et al. |
| 5,186,712 A | 2/1993 | Kelso et al. |
| 5,188,607 A | 2/1993 | Wu |
| 5,190,528 A | 3/1993 | Fonger et al. |
| 5,192,301 A | 3/1993 | Kamiya et al. |
| 5,195,974 A | 3/1993 | Hardy |
| 5,195,980 A | 3/1993 | Catlin |
| 5,195,985 A | 3/1993 | Hall |
| 5,205,830 A | 4/1993 | Dassa |
| 5,215,527 A | 6/1993 | Beck et al. |
| 5,215,528 A | 6/1993 | Purdy et al. |
| 5,217,435 A | 6/1993 | Kring |
| 5,219,335 A | 6/1993 | Willard et al. |
| 5,221,255 A | 6/1993 | Mahurkar et al. |
| 5,222,944 A | 6/1993 | Harris |
| 5,225,369 A | 7/1993 | Su et al. |
| 5,226,899 A | 7/1993 | Lee et al. |
| D338,955 S | 8/1993 | Gresl et al. |
| 5,234,410 A | 8/1993 | Graham et al. |
| 5,242,411 A | 9/1993 | Yamamoto et al. |
| 5,246,426 A | 9/1993 | Lewis et al. |
| 5,246,430 A | 9/1993 | MacFarlane |
| 5,254,107 A | 10/1993 | Soltesz |
| 5,257,980 A | 11/1993 | Van Antwerp et al. |
| 5,267,982 A | 12/1993 | Sylvanowicz |
| 5,269,771 A | 12/1993 | Thomas et al. |
| D345,419 S | 3/1994 | Horrigan et al. |
| 5,290,310 A | 3/1994 | Makower et al. |
| 5,297,546 A | 3/1994 | Spofford et al. |
| 5,312,359 A | 5/1994 | Wallace |
| 5,312,361 A | 5/1994 | Zadini et al. |
| 5,312,363 A | 5/1994 | Ryan et al. |
| 5,320,608 A | 6/1994 | Gerrone |
| 5,322,517 A | 6/1994 | Sircom et al. |
| 5,330,435 A | 7/1994 | Vaillancourt |
| 5,334,159 A | 8/1994 | Turkel |
| 5,338,311 A | 8/1994 | Mahurkar |
| 5,352,205 A | 10/1994 | Dales et al. |
| 5,358,796 A | 10/1994 | Nakamura et al. |
| 5,366,441 A | 11/1994 | Crawford |
| 5,368,661 A | 11/1994 | Nakamura et al. |
| D353,668 S | 12/1994 | Banks et al. |
| 5,376,082 A | 12/1994 | Phelps |
| 5,376,094 A | 12/1994 | Kline |
| 5,380,290 A | 1/1995 | Makower et al. |
| 5,380,292 A | 1/1995 | Wilson |
| 5,395,341 A | 3/1995 | Slater |
| 5,397,311 A | 3/1995 | Walker et al. |
| 5,405,323 A | 4/1995 | Rogers et al. |
| 5,415,177 A | 5/1995 | Zadini et al. |
| 5,415,645 A | 5/1995 | Friend |
| 5,419,766 A | 5/1995 | Chang |
| 5,419,777 A | 5/1995 | Honing |
| 5,423,760 A | 6/1995 | Yoon |
| 5,425,718 A | 6/1995 | Tay et al. |
| 5,431,506 A | 7/1995 | Masunaga |
| 5,445,625 A | 8/1995 | Voda |
| 5,454,785 A | 10/1995 | Smith |
| 5,454,790 A | 10/1995 | Dubrul |
| 5,456,258 A | 10/1995 | Kondo et al. |
| 5,456,668 A | 10/1995 | Ogle, II |
| 5,458,658 A | 10/1995 | Sircom |
| 5,466,230 A | 11/1995 | Davila |
| 5,480,389 A | 1/1996 | McWha et al. |
| 5,482,395 A | 1/1996 | Gasparini |
| 5,484,419 A | 1/1996 | Fleck |
| 5,487,734 A | 1/1996 | Thorne et al. |
| 5,489,273 A | 2/1996 | Whitney et al. |
| 5,496,281 A | 3/1996 | Krebs |
| 5,501,675 A | 3/1996 | Erskine |
| 5,507,300 A | 4/1996 | Mukai et al. |
| 5,512,052 A | 4/1996 | Jesch |
| 5,514,108 A | 5/1996 | Stevens |
| 5,520,655 A | 5/1996 | Davila et al. |
| 5,520,657 A | 5/1996 | Sellers et al. |
| D371,195 S | 6/1996 | Krebs |
| 5,522,807 A | 6/1996 | Luther |
| 5,527,290 A | 6/1996 | Zadini et al. |
| 5,527,291 A | 6/1996 | Zadini et al. |
| 5,531,701 A | 7/1996 | Luther |
| 5,531,713 A | 7/1996 | Mastronardi et al. |
| 5,533,988 A | 7/1996 | Dickerson et al. |
| 5,535,785 A | 7/1996 | Werge |
| 5,542,933 A | 8/1996 | Marks |
| 5,554,136 A | 9/1996 | Luther |
| 5,562,629 A | 10/1996 | Haughton et al. |
| 5,562,630 A | 10/1996 | Nichols |
| 5,562,631 A | 10/1996 | Bogert |
| 5,562,633 A | 10/1996 | Wozencroft |
| 5,562,634 A | 10/1996 | Flumene et al. |
| 5,569,202 A | 10/1996 | Kovalic et al. |
| 5,569,217 A | 10/1996 | Luther |
| 5,571,073 A | 11/1996 | Castillo |
| 5,573,510 A | 11/1996 | Isaacson |
| 5,591,194 A | 1/1997 | Berthiaume |
| 5,599,291 A | 2/1997 | Balbierz et al. |
| 5,599,327 A | 2/1997 | Sugahara et al. |
| 5,609,583 A | 3/1997 | Hakki et al. |
| 5,613,663 A | 3/1997 | Schmidt et al. |
| 5,613,954 A | 3/1997 | Nelson et al. |
| 5,630,802 A | 5/1997 | Moellmann et al. |
| 5,630,823 A | 5/1997 | Schmitz-Rode et al. |
| 5,634,475 A | 6/1997 | Wolvek |
| 5,634,913 A | 6/1997 | Stinger |
| 5,637,091 A | 6/1997 | Hakky et al. |
| 5,645,076 A | 7/1997 | Yoon |
| 5,651,772 A | 7/1997 | Arnett |
| D383,538 S | 9/1997 | Erskine et al. |
| 5,662,622 A | 9/1997 | Gore et al. |
| 5,674,241 A | 10/1997 | Bley et al. |
| 5,676,658 A | 10/1997 | Erskine |
| 5,683,368 A | 11/1997 | Schmidt |
| 5,683,370 A | 11/1997 | Luther et al. |
| 5,685,855 A | 11/1997 | Erskine |
| 5,685,858 A | 11/1997 | Kawand |
| 5,685,860 A | 11/1997 | Chang et al. |
| 5,688,249 A | 11/1997 | Chang et al. |
| 5,693,025 A | 12/1997 | Stevens |
| 5,695,474 A | 12/1997 | Daugherty |
| 5,700,250 A | 12/1997 | Erskine |
| 5,702,369 A | 12/1997 | Mercereau |
| 5,704,914 A * | 1/1998 | Stocking ............ A61M 25/0606 604/164.07 |
| 5,722,425 A * | 3/1998 | Bostrom ................ A61M 25/09 600/585 |
| 5,725,503 A | 3/1998 | Arnett |
| 5,730,150 A | 3/1998 | Peppel et al. |
| 5,730,733 A | 3/1998 | Mortier et al. |
| 5,730,741 A | 3/1998 | Horzewski et al. |
| 5,738,144 A | 4/1998 | Rogers |
| 5,738,660 A | 4/1998 | Luther |
| 5,743,882 A | 4/1998 | Luther |
| 5,743,888 A | 4/1998 | Wilkes et al. |
| 5,749,371 A | 5/1998 | Zadini et al. |
| 5,749,857 A | 5/1998 | Cuppy |
| 5,750,741 A | 5/1998 | Crocker et al. |
| 5,755,693 A | 5/1998 | Walker et al. |
| 5,755,709 A | 5/1998 | Cuppy |
| 5,762,630 A | 6/1998 | Bley et al. |
| 5,762,636 A | 6/1998 | Rupp et al. |
| 5,765,682 A | 6/1998 | Bley et al. |
| 5,779,679 A | 7/1998 | Shaw |
| 5,779,680 A | 7/1998 | Yoon |
| 5,779,681 A | 7/1998 | Bonn |
| 5,782,807 A | 7/1998 | Falvai et al. |
| D397,434 S | 8/1998 | Pike |
| 5,792,124 A | 8/1998 | Horrigan et al. |
| 5,800,395 A | 9/1998 | Botich et al. |
| 5,807,339 A | 9/1998 | Bostrom et al. |
| 5,807,342 A | 9/1998 | Musgrave et al. |
| 5,807,350 A | 9/1998 | Diaz |
| 5,810,835 A | 9/1998 | Ryan et al. |

(56) References Cited

U.S. PATENT DOCUMENTS

| | | |
|---|---|---|
| 5,813,411 A | 9/1998 | Van Bladel et al. |
| 5,817,058 A | 10/1998 | Shaw |
| 5,817,069 A | 10/1998 | Arnett |
| 5,824,001 A | 10/1998 | Erskine |
| 5,827,202 A | 10/1998 | Miraki et al. |
| 5,827,221 A | 10/1998 | Phelps |
| 5,827,227 A | 10/1998 | DeLago |
| 5,830,190 A | 11/1998 | Howell |
| 5,830,224 A | 11/1998 | Cohn et al. |
| 5,839,470 A | 11/1998 | Hiejima et al. |
| 5,843,038 A | 12/1998 | Bailey |
| 5,846,259 A | 12/1998 | Berthiaume |
| 5,851,196 A | 12/1998 | Arnett |
| 5,853,393 A | 12/1998 | Bogert |
| 5,855,615 A | 1/1999 | Bley et al. |
| 5,858,002 A | 1/1999 | Jesch |
| 5,865,806 A | 2/1999 | Howell |
| 5,873,864 A | 2/1999 | Luther et al. |
| 5,879,332 A | 3/1999 | Schwemberger et al. |
| 5,885,217 A | 3/1999 | Gisselberg et al. |
| 5,885,251 A | 3/1999 | Luther |
| 5,891,098 A | 4/1999 | Huang |
| 5,891,105 A | 4/1999 | Mahurkar |
| 5,895,398 A | 4/1999 | Wensel et al. |
| 5,902,274 A | 5/1999 | Yamamoto et al. |
| 5,902,832 A | 5/1999 | Van Bladel et al. |
| 5,911,705 A | 6/1999 | Howell |
| 5,911,710 A | 6/1999 | Barry et al. |
| 5,913,848 A | 6/1999 | Luther et al. |
| 5,916,208 A | 6/1999 | Luther et al. |
| 5,928,199 A | 7/1999 | Nakagami |
| 5,935,110 A | 8/1999 | Brimhall |
| 5,941,854 A | 8/1999 | Bhitiyakul |
| 5,944,690 A | 8/1999 | Falwell et al. |
| 5,947,930 A | 9/1999 | Schwemberger et al. |
| 5,951,520 A | 9/1999 | Burzynski et al. |
| 5,954,698 A | 9/1999 | Pike |
| 5,957,893 A | 9/1999 | Luther et al. |
| 5,964,744 A | 10/1999 | Balbierz et al. |
| 5,967,490 A | 10/1999 | Pike |
| 5,984,895 A | 11/1999 | Padilla et al. |
| 5,984,903 A | 11/1999 | Nadal |
| 5,989,220 A | 11/1999 | Shaw et al. |
| 5,989,271 A | 11/1999 | Bonnette et al. |
| 5,997,507 A | 12/1999 | Dysarz |
| 5,997,510 A | 12/1999 | Schwemberger |
| 6,004,278 A | 12/1999 | Botich et al. |
| 6,004,294 A | 12/1999 | Brimhall et al. |
| 6,004,295 A | 12/1999 | Langer et al. |
| 6,011,988 A | 1/2000 | Lynch et al. |
| 6,019,736 A | 2/2000 | Avellanet et al. |
| 6,022,319 A | 2/2000 | Willard et al. |
| 6,024,727 A | 2/2000 | Thorne et al. |
| 6,024,729 A | 2/2000 | Dehdashtian et al. |
| 6,045,734 A | 4/2000 | Luther et al. |
| 6,056,726 A | 5/2000 | Isaacson |
| 6,066,100 A | 5/2000 | Willard et al. |
| 6,074,378 A | 6/2000 | Mouri et al. |
| 6,077,244 A | 6/2000 | Botich et al. |
| 6,080,137 A | 6/2000 | Pike |
| 6,083,237 A | 7/2000 | Huitema et al. |
| 6,096,004 A | 8/2000 | Meglan et al. |
| 6,096,005 A | 8/2000 | Botich et al. |
| 6,120,494 A | 9/2000 | Jonkman |
| 6,126,633 A | 10/2000 | Kaji et al. |
| 6,126,641 A | 10/2000 | Shields |
| 6,139,532 A | 10/2000 | Howell et al. |
| 6,139,557 A | 10/2000 | Passafaro et al. |
| 6,159,179 A | 12/2000 | Simonson |
| 6,171,234 B1 | 1/2001 | White et al. |
| 6,171,287 B1 | 1/2001 | Lynn et al. |
| 6,176,842 B1 | 1/2001 | Tachibana et al. |
| 6,193,690 B1 | 2/2001 | Dysarz |
| 6,197,001 B1 | 3/2001 | Wilson et al. |
| 6,197,007 B1 | 3/2001 | Thorne et al. |
| 6,197,041 B1 | 3/2001 | Shichman et al. |
| 6,203,527 B1 | 3/2001 | Zadini et al. |
| 6,213,978 B1 | 4/2001 | Voyten |
| 6,217,558 B1 | 4/2001 | Zadini et al. |
| 6,221,047 B1 | 4/2001 | Green et al. |
| 6,221,049 B1 | 4/2001 | Selmon et al. |
| 6,224,569 B1 | 5/2001 | Brimhall |
| 6,228,060 B1 | 5/2001 | Howell |
| 6,228,062 B1 | 5/2001 | Howell et al. |
| 6,228,073 B1 | 5/2001 | Noone |
| 6,245,045 B1 | 6/2001 | Stratienko |
| 6,251,092 B1 | 6/2001 | Qin et al. |
| 6,268,399 B1 | 7/2001 | Hultine et al. |
| 6,270,480 B1 | 8/2001 | Dorr et al. |
| 6,273,871 B1 | 8/2001 | Davis et al. |
| 6,280,419 B1 | 8/2001 | Vojtasek |
| 6,309,379 B1 | 10/2001 | Willard et al. |
| 6,319,244 B2 | 11/2001 | Suresh et al. |
| 6,322,537 B1 | 11/2001 | Chang |
| D452,003 S | 12/2001 | Niermann |
| 6,325,781 B1 | 12/2001 | Takagi et al. |
| 6,325,797 B1 | 12/2001 | Stewart et al. |
| 6,336,914 B1 | 1/2002 | Gillespie, III |
| 6,352,520 B1 | 3/2002 | Miyazaki et al. |
| 6,368,337 B1 | 4/2002 | Kieturakis et al. |
| 6,379,333 B1 | 4/2002 | Brimhall et al. |
| 6,379,372 B1 | 4/2002 | Dehdashtian et al. |
| D457,955 S | 5/2002 | Bilitz |
| 6,406,442 B1 | 6/2002 | McFann et al. |
| D460,179 S | 7/2002 | Isoda et al. |
| 6,422,989 B1 | 7/2002 | Hektner |
| 6,436,070 B1 | 8/2002 | Botich et al. |
| 6,436,112 B2 | 8/2002 | Wensel et al. |
| 6,451,052 B1 | 9/2002 | Burmeister et al. |
| 6,461,362 B1 | 10/2002 | Halseth et al. |
| 6,475,217 B1 | 11/2002 | Platt |
| 6,478,779 B1 | 11/2002 | Hu |
| 6,485,473 B1 | 11/2002 | Lynn |
| 6,485,497 B2 | 11/2002 | Vvensel et al. |
| 6,497,681 B1 | 12/2002 | Brenner |
| 6,506,181 B2 | 1/2003 | Meng et al. |
| 6,514,236 B1 | 2/2003 | Stratienko |
| 6,524,276 B1 | 2/2003 | Halseth et al. |
| D471,980 S | 3/2003 | Caizza |
| 6,527,759 B1 | 3/2003 | Tachibana et al. |
| 6,530,913 B1 | 3/2003 | Giba et al. |
| 6,530,935 B2 | 3/2003 | Wensel et al. |
| 6,540,725 B1 | 4/2003 | Ponzi |
| 6,540,732 B1 | 4/2003 | Botich et al. |
| 6,544,239 B2 | 4/2003 | Kinsey et al. |
| 6,547,762 B1 | 4/2003 | Botich et al. |
| 6,558,355 B1 | 5/2003 | Metzger et al. |
| 6,582,402 B1 | 6/2003 | Erskine |
| 6,582,440 B1 | 6/2003 | Brumbach |
| 6,585,703 B1 | 7/2003 | Kassel et al. |
| 6,589,262 B1 | 7/2003 | Honebrink et al. |
| 6,595,955 B2 | 7/2003 | Ferguson et al. |
| 6,595,959 B1 | 7/2003 | Stratienko |
| 6,607,511 B2 | 8/2003 | Halseth et al. |
| 6,616,630 B1 | 9/2003 | Woehr et al. |
| 6,620,136 B1 | 9/2003 | Pressly, Sr. et al. |
| 6,623,449 B2 | 9/2003 | Paskar |
| 6,626,868 B1 | 9/2003 | Prestidge et al. |
| 6,626,869 B1 | 9/2003 | Bint |
| 6,632,201 B1 | 10/2003 | Mathias et al. |
| 6,638,252 B2 | 10/2003 | Moulton et al. |
| 6,641,564 B1 | 11/2003 | Kraus |
| 6,645,178 B1 | 11/2003 | Junker et al. |
| 6,652,486 B2 | 11/2003 | Bialecki et al. |
| 6,652,490 B2 | 11/2003 | Howell |
| 6,663,577 B2 | 12/2003 | Jen et al. |
| 6,663,592 B2 | 12/2003 | Rhad et al. |
| 6,666,865 B2 | 12/2003 | Platt |
| 6,679,900 B2 | 1/2004 | Kieturakis et al. |
| 6,689,102 B2 | 2/2004 | Greene |
| 6,692,508 B2 | 2/2004 | Wensel et al. |
| 6,692,509 B2 | 2/2004 | Wensel et al. |
| 6,695,814 B2 | 2/2004 | Greene et al. |
| 6,695,856 B2 | 2/2004 | Kieturakis et al. |

(56) References Cited

U.S. PATENT DOCUMENTS

| | | |
|---|---|---|
| 6,695,860 B1 | 2/2004 | Ward et al. |
| 6,699,221 B2 | 3/2004 | Vaillancourt |
| 6,702,811 B2 | 3/2004 | Stewart et al. |
| 6,706,018 B2 | 3/2004 | Westlund et al. |
| 6,711,444 B2 | 3/2004 | Koblish |
| 6,712,790 B1 | 3/2004 | Prestidge et al. |
| 6,712,797 B1 | 3/2004 | Southern, Jr. |
| 6,716,197 B2 | 4/2004 | Svendsen |
| 6,730,062 B2 | 5/2004 | Hoffman et al. |
| 6,740,063 B2 | 5/2004 | Lynn |
| 6,740,096 B2 | 5/2004 | Teague et al. |
| 6,745,080 B2 | 6/2004 | Koblish |
| 6,749,588 B1 | 6/2004 | Howell et al. |
| 6,764,468 B1 | 7/2004 | East |
| D494,270 S | 8/2004 | Reschke |
| 6,776,788 B1 | 8/2004 | Klint et al. |
| 6,796,962 B2 | 9/2004 | Ferguson et al. |
| 6,824,545 B2 | 11/2004 | Sepetka et al. |
| 6,832,715 B2 | 12/2004 | Eungard et al. |
| 6,835,190 B2 | 12/2004 | Nguyen |
| 6,837,867 B2 | 1/2005 | Kortelling |
| 6,860,871 B2 | 3/2005 | Kuracina et al. |
| 6,872,193 B2 | 3/2005 | Shaw et al. |
| 6,887,220 B2 | 5/2005 | Hogendijk |
| 6,902,546 B2 | 6/2005 | Ferguson |
| 6,905,483 B2 | 6/2005 | Newby et al. |
| 6,913,595 B2 | 7/2005 | Mastorakis |
| 6,916,311 B2 | 7/2005 | Vojtasek |
| 6,921,386 B2 | 7/2005 | Shue et al. |
| 6,921,391 B1 | 7/2005 | Barker et al. |
| 6,929,624 B1 | 8/2005 | Del Castillo |
| 6,939,325 B2 | 9/2005 | Raining |
| 6,942,652 B1 | 9/2005 | Pressly, Sr. et al. |
| 6,953,448 B2 | 10/2005 | Moulton et al. |
| 6,958,054 B2 | 10/2005 | Fitzgerald |
| 6,958,055 B2 | 10/2005 | Donnan et al. |
| 6,960,191 B2 | 11/2005 | Howlett et al. |
| 6,972,002 B2 | 12/2005 | Thorne |
| 6,974,438 B2 | 12/2005 | Shekalim |
| 6,994,693 B2 | 2/2006 | Tal |
| 7,001,396 B2 | 2/2006 | Glazier et al. |
| 7,004,927 B2 | 2/2006 | Ferguson et al. |
| 7,008,404 B2 | 3/2006 | Nakajima |
| 7,018,372 B2 | 3/2006 | Casey |
| 7,018,390 B2 | 3/2006 | Turovskiy et al. |
| 7,025,746 B2 | 4/2006 | Tal |
| 7,029,467 B2 | 4/2006 | Currier et al. |
| 7,033,335 B2 | 4/2006 | Haarala et al. |
| 7,044,935 B2 | 5/2006 | Shue et al. |
| 7,060,055 B2 | 6/2006 | Wilkinson et al. |
| 7,090,656 B1 | 8/2006 | Botich et al. |
| 7,094,243 B2 | 8/2006 | Mulholland et al. |
| 7,097,633 B2 | 8/2006 | Botich et al. |
| 7,125,396 B2 | 10/2006 | Leinsing et al. |
| 7,141,040 B2 | 11/2006 | Lichtenberg |
| 7,153,276 B2 | 12/2006 | Barker et al. |
| 7,163,520 B2 | 1/2007 | Bernard et al. |
| 7,169,159 B2 | 1/2007 | Green et al. |
| 7,179,244 B2 | 2/2007 | Smith et al. |
| 7,191,900 B2 | 3/2007 | Opie et al. |
| 7,192,433 B2 | 3/2007 | Osypka et al. |
| 7,204,813 B2 | 4/2007 | Shue et al. |
| 7,291,130 B2 | 11/2007 | McGurk |
| 7,303,547 B2 | 12/2007 | Pressly, Sr. et al. |
| 7,303,548 B2 | 12/2007 | Rhad et al. |
| 7,314,462 B2 | 1/2008 | O'Reagan et al. |
| 7,331,966 B2 | 2/2008 | Soma et al. |
| 7,344,516 B2 | 3/2008 | Erskine |
| 7,354,422 B2 | 4/2008 | Riesenberger et al. |
| 7,381,205 B2 | 6/2008 | Thommen |
| 7,396,346 B2 | 7/2008 | Nakajima |
| 7,413,562 B2 | 8/2008 | Ferguson et al. |
| 7,422,572 B2 | 9/2008 | Popov et al. |
| 7,458,954 B2 | 12/2008 | Ferguson et al. |
| 7,465,294 B1 | 12/2008 | Vladimirsky |
| 7,468,057 B2 | 12/2008 | Ponzi |
| 7,470,254 B2 | 12/2008 | Basta et al. |
| 7,491,176 B2 | 2/2009 | Mann |
| 7,494,010 B2 | 2/2009 | Opie et al. |
| 7,500,965 B2 | 3/2009 | Menzi et al. |
| 7,507,222 B2 | 3/2009 | Cindrich et al. |
| 7,513,887 B2 | 4/2009 | Halseth et al. |
| 7,513,888 B2 | 4/2009 | Sircom et al. |
| 7,524,306 B2 | 4/2009 | Botich et al. |
| 7,530,965 B2 | 5/2009 | Villa et al. |
| 7,534,227 B2 | 5/2009 | Kulli |
| 7,544,170 B2 | 6/2009 | Williams et al. |
| 7,556,617 B2 | 7/2009 | Voorhees, Jr. et al. |
| 7,566,323 B2 | 7/2009 | Chang |
| D601,243 S | 9/2009 | Bierman et al. |
| 7,597,681 B2 | 10/2009 | Sutton et al. |
| D604,839 S | 11/2009 | Crawford et al. |
| 7,611,485 B2 | 11/2009 | Ferguson |
| 7,618,395 B2 | 11/2009 | Ferguson |
| 7,628,769 B2 | 12/2009 | Grandt et al. |
| 7,632,243 B2 | 12/2009 | Bialecki et al. |
| 7,645,263 B2 | 1/2010 | Angel et al. |
| 7,654,988 B2 | 2/2010 | Moulton et al. |
| 7,658,725 B2 | 2/2010 | Bialecki et al. |
| D612,043 S | 3/2010 | Young et al. |
| 7,678,080 B2 | 3/2010 | Shue et al. |
| 7,682,358 B2 | 3/2010 | Gullickson et al. |
| 7,691,088 B2 | 4/2010 | Howell |
| 7,691,090 B2 | 4/2010 | Belley et al. |
| 7,691,093 B2 | 4/2010 | Brimhall |
| 7,695,458 B2 | 4/2010 | Belley et al. |
| 7,699,807 B2 | 4/2010 | Faust et al. |
| D615,197 S | 5/2010 | Koh et al. |
| 7,708,721 B2 | 5/2010 | Khaw |
| 7,713,243 B2 | 5/2010 | Hillman |
| 7,717,875 B2 | 5/2010 | Knudson et al. |
| 7,722,567 B2 | 5/2010 | Tal |
| 7,722,569 B2 | 5/2010 | Soderholm et al. |
| D617,893 S | 6/2010 | Bierman et al. |
| 7,731,691 B2 | 6/2010 | Cote et al. |
| 7,736,332 B2 | 6/2010 | Carlyon et al. |
| 7,736,337 B2 | 6/2010 | Diep et al. |
| 7,736,339 B2 | 6/2010 | Woehr |
| 7,736,342 B2 | 6/2010 | Abriles et al. |
| 7,740,615 B2 | 6/2010 | Shaw et al. |
| 7,744,574 B2 | 6/2010 | Pederson et al. |
| 7,753,877 B2 | 7/2010 | Bialecki et al. |
| 7,753,887 B2 | 7/2010 | Botich et al. |
| 7,762,984 B2 | 7/2010 | Kumoyama et al. |
| 7,762,993 B2 | 7/2010 | Perez |
| 7,766,879 B2 | 8/2010 | Tan et al. |
| 7,776,052 B2 | 8/2010 | Greenberg et al. |
| 7,785,296 B2 | 8/2010 | Muskatello et al. |
| 7,794,424 B2 | 9/2010 | Paskar |
| 7,798,994 B2 | 9/2010 | Brimhall |
| 7,803,142 B2 | 9/2010 | Longson et al. |
| 7,828,773 B2 | 11/2010 | Swisher et al. |
| 7,828,774 B2 | 11/2010 | Harding et al. |
| 7,850,644 B2 | 12/2010 | Gonzalez et al. |
| D634,843 S | 3/2011 | Kim et al. |
| 7,896,862 B2 | 3/2011 | Long et al. |
| 7,905,857 B2 | 3/2011 | Swisher |
| 7,914,488 B2 | 3/2011 | Dickerson |
| 7,914,492 B2 | 3/2011 | Heuser |
| 7,922,696 B2 | 4/2011 | Tal et al. |
| 7,922,698 B2 | 4/2011 | Riesenberger et al. |
| 7,927,314 B2 | 4/2011 | Kuracina et al. |
| 7,935,080 B2 | 5/2011 | Howell et al. |
| 7,959,613 B2 | 6/2011 | Rhad et al. |
| 7,972,324 B2 | 7/2011 | Quint |
| 8,029,470 B2 | 10/2011 | Whiting et al. |
| 8,029,472 B2 | 10/2011 | Leinsing et al. |
| 8,048,031 B2 | 11/2011 | Shaw et al. |
| 8,048,039 B2 | 11/2011 | Carlyon et al. |
| 8,057,404 B2 | 11/2011 | Fujiwara et al. |
| 8,079,979 B2 | 12/2011 | Moorehead |
| D653,329 S | 1/2012 | Lee-Sepsick |
| 8,105,286 B2 | 1/2012 | Anderson et al. |
| 8,105,315 B2 | 1/2012 | Johnson et al. |

(56) References Cited

U.S. PATENT DOCUMENTS

| | | |
|---|---|---|
| 8,123,727 B2 | 2/2012 | Luther et al. |
| 8,152,758 B2 | 4/2012 | Chan et al. |
| 8,162,881 B2 | 4/2012 | Lilley, Jr. et al. |
| 8,167,851 B2 | 5/2012 | Sen |
| 8,177,753 B2 | 5/2012 | Vitullo et al. |
| RE43,473 E | 6/2012 | Newby et al. |
| 8,192,402 B2 | 6/2012 | Anderson et al. |
| 8,202,253 B1 | 6/2012 | Wexler |
| 8,206,343 B2 | 6/2012 | Racz |
| 8,221,387 B2 | 7/2012 | Shelso et al. |
| 8,251,923 B2 | 8/2012 | Carrez et al. |
| 8,251,950 B2 | 8/2012 | Albert et al. |
| D667,111 S | 9/2012 | Robinson |
| 8,257,322 B2 | 9/2012 | Koehler et al. |
| 8,273,054 B2 | 9/2012 | St. Germain et al. |
| 8,286,657 B2 | 10/2012 | Belley et al. |
| 8,298,186 B2 | 10/2012 | Popov |
| 8,308,691 B2 | 11/2012 | Woehr et al. |
| D672,456 S | 12/2012 | Lee-Sepsick |
| 8,328,762 B2 | 12/2012 | Woehr et al. |
| 8,328,837 B2 | 12/2012 | Binmoeller |
| 8,333,735 B2 | 12/2012 | Woehr et al. |
| 8,337,424 B2 | 12/2012 | Palmer et al. |
| 8,337,463 B2 | 12/2012 | Woehr et al. |
| 8,337,471 B2 | 12/2012 | Baid |
| D675,318 S | 1/2013 | Luk et al. |
| 8,361,020 B2 | 1/2013 | Stout |
| 8,377,006 B2 | 2/2013 | Tal et al. |
| 8,388,583 B2 | 3/2013 | Stout et al. |
| 8,403,886 B2 | 3/2013 | Bialecki et al. |
| 8,412,300 B2 | 4/2013 | Sonderegger |
| 8,419,688 B2 | 4/2013 | Woehr et al. |
| 8,454,536 B2 | 6/2013 | Raulerson et al. |
| 8,460,247 B2 | 6/2013 | Woehr et al. |
| 8,469,928 B2 | 6/2013 | Stout et al. |
| 8,496,628 B2 | 7/2013 | Erskine |
| D687,548 S | 8/2013 | Hayashi |
| 8,506,533 B2 | 8/2013 | Carlyon et al. |
| 8,509,340 B2 | 8/2013 | Michelitsch |
| 8,517,959 B2 | 8/2013 | Kurosawa et al. |
| 8,535,271 B2 | 9/2013 | Fuchs et al. |
| 8,540,728 B2 | 9/2013 | Woehr et al. |
| 8,574,203 B2 | 11/2013 | Stout et al. |
| 8,585,660 B2 | 11/2013 | Murphy |
| 8,591,467 B2 | 11/2013 | Walker et al. |
| 8,591,468 B2 | 11/2013 | Woehr et al. |
| 8,597,249 B2 | 12/2013 | Woehr et al. |
| 8,622,931 B2 | 1/2014 | Teague et al. |
| 8,622,972 B2 | 1/2014 | Nystrom et al. |
| D700,318 S | 2/2014 | Amoah et al. |
| 8,647,301 B2 | 2/2014 | Bialecki et al. |
| 8,647,313 B2 | 2/2014 | Woehr et al. |
| 8,647,324 B2 | 2/2014 | DeLegge et al. |
| 8,652,104 B2 | 2/2014 | Goral et al. |
| 8,657,790 B2 | 2/2014 | Tal et al. |
| 8,672,888 B2 | 3/2014 | Tal |
| 8,679,063 B2 | 3/2014 | Stout et al. |
| 8,690,833 B2 | 4/2014 | Belson |
| 8,721,546 B2 | 5/2014 | Belson |
| 8,728,030 B2 | 5/2014 | Woehr |
| 8,728,035 B2 | 5/2014 | Warring et al. |
| 8,740,964 B2 | 6/2014 | Hartley |
| 8,747,387 B2 | 6/2014 | Belley et al. |
| 8,753,317 B2 | 6/2014 | Osborne et al. |
| 8,764,711 B2 | 7/2014 | Kuracina et al. |
| D710,495 S | 8/2014 | Wu et al. |
| 8,814,833 B2 | 8/2014 | Farrell et al. |
| D713,957 S | 9/2014 | Woehr et al. |
| D714,436 S | 9/2014 | Lee-Sepsick |
| 8,845,584 B2 | 9/2014 | Ferguson et al. |
| D715,931 S | 10/2014 | Watanabe et al. |
| 8,864,714 B2 | 10/2014 | Harding et al. |
| 8,900,192 B2 | 12/2014 | Anderson et al. |
| 8,932,257 B2 | 1/2015 | Woehr |
| 8,932,258 B2 | 1/2015 | Blanchard et al. |
| 8,956,327 B2 | 2/2015 | Bierman et al. |
| 8,974,426 B2 | 3/2015 | Corcoran et al. |
| 8,979,802 B2 | 3/2015 | Woehr |
| 8,986,227 B2 | 3/2015 | Belson |
| D726,908 S | 4/2015 | Yu et al. |
| 8,998,852 B2 | 4/2015 | Blanchard et al. |
| 9,005,169 B2 | 4/2015 | Gravesen et al. |
| 9,011,351 B2 | 4/2015 | Hoshinouchi |
| 9,011,381 B2 | 4/2015 | Yamada et al. |
| D728,781 S | 5/2015 | Pierson et al. |
| 9,033,927 B2 | 5/2015 | Maan et al. |
| D733,289 S | 6/2015 | Blanchard et al. |
| 9,044,583 B2 | 6/2015 | Vaillancourt |
| D735,321 S | 7/2015 | Blanchard |
| 9,095,683 B2 | 8/2015 | Hall et al. |
| 9,101,746 B2 | 8/2015 | Stout et al. |
| 9,114,241 B2 | 8/2015 | Stout et al. |
| 9,138,252 B2 | 9/2015 | Bierman et al. |
| 9,138,545 B2 | 9/2015 | Shaw et al. |
| 9,138,559 B2 | 9/2015 | Odland et al. |
| RE45,776 E | 10/2015 | Root et al. |
| D740,410 S | 10/2015 | Korkuch et al. |
| 9,162,036 B2 | 10/2015 | Caples et al. |
| 9,162,037 B2 | 10/2015 | Belson et al. |
| 9,180,275 B2 | 11/2015 | Helm |
| D746,445 S | 12/2015 | Lazarus |
| 9,216,109 B2 | 12/2015 | Badawi et al. |
| 9,220,531 B2 | 12/2015 | Datta et al. |
| 9,220,871 B2 | 12/2015 | Thorne et al. |
| D748,254 S | 1/2016 | Freigang et al. |
| 9,227,038 B2 | 1/2016 | Woehr |
| D748,774 S | 2/2016 | Caron |
| D748,777 S | 2/2016 | Uenishi et al. |
| D749,214 S | 2/2016 | Uenishi et al. |
| D749,727 S | 2/2016 | Wapler et al. |
| D751,194 S | 3/2016 | Yu et al. |
| D752,737 S | 3/2016 | Ohashi |
| D755,368 S | 5/2016 | Efinger et al. |
| 9,522,254 B2 | 12/2016 | Belson |
| 9,616,201 B2 | 4/2017 | Belson |
| 9,675,784 B2 | 6/2017 | Belson |
| 9,757,540 B2 | 9/2017 | Belson |
| 9,861,792 B2 | 1/2018 | Hall et al. |
| 9,872,971 B2 | 1/2018 | Blanchard |
| 9,950,139 B2 | 4/2018 | Blanchard et al. |
| 10,086,171 B2 | 10/2018 | Belson |
| 10,232,146 B2 | 3/2019 | Braithwaite et al. |
| 10,328,239 B2 | 6/2019 | Belson |
| 10,493,262 B2 | 12/2019 | Tran et al. |
| 10,525,236 B2 | 1/2020 | Belson |
| 10,688,280 B2 | 6/2020 | Blanchard et al. |
| 10,688,281 B2 | 6/2020 | Blanchard et al. |
| 10,722,685 B2 | 7/2020 | Blanchard et al. |
| 2001/0014786 A1 | 8/2001 | Greene et al. |
| 2001/0020153 A1 | 9/2001 | Howell |
| 2002/0052576 A1 | 5/2002 | Massengale |
| 2002/0077595 A1 | 6/2002 | Hundertmark et al. |
| 2002/0103446 A1 | 8/2002 | McFann et al. |
| 2002/0107526 A1 | 8/2002 | Greenberg et al. |
| 2002/0128604 A1 | 9/2002 | Nakajima |
| 2002/0165497 A1 | 11/2002 | Greene |
| 2002/0177812 A1 | 11/2002 | Moulton et al. |
| 2003/0032922 A1 | 2/2003 | Moorehead |
| 2003/0032936 A1 | 2/2003 | Lederman |
| 2003/0060760 A1 | 3/2003 | Botich et al. |
| 2003/0073956 A1 | 4/2003 | Hoffman et al. |
| 2003/0120214 A1 | 6/2003 | Howell |
| 2003/0153874 A1 | 8/2003 | Tal |
| 2003/0187396 A1 | 10/2003 | Ponzi |
| 2003/0204186 A1 | 10/2003 | Geistert |
| 2004/0019329 A1 | 1/2004 | Erskine |
| 2004/0044302 A1 | 3/2004 | Bernard et al. |
| 2004/0044313 A1 | 3/2004 | Nakajima |
| 2004/0092879 A1 | 5/2004 | Kraus et al. |
| 2004/0106903 A1 | 6/2004 | Shue et al. |
| 2004/0111059 A1 | 6/2004 | Howlett et al. |
| 2004/0122373 A1 | 6/2004 | Botich et al. |
| 2004/0176758 A1 | 9/2004 | Yassinzadeh |
| 2004/0193118 A1 | 9/2004 | Bergeron |

(56) References Cited

U.S. PATENT DOCUMENTS

| | | |
|---|---|---|
| 2004/0215146 A1 | 10/2004 | Lampropoulos et al. |
| 2004/0236288 A1 | 11/2004 | Howell et al. |
| 2004/0243061 A1 | 12/2004 | McGurk |
| 2004/0267204 A1 | 12/2004 | Brustowicz |
| 2005/0004524 A1 | 1/2005 | Newby et al. |
| 2005/0010095 A1 | 1/2005 | Stewart et al. |
| 2005/0020940 A1 | 1/2005 | Opie et al. |
| 2005/0021002 A1 | 1/2005 | Deckman et al. |
| 2005/0027256 A1 | 2/2005 | Barker |
| 2005/0033137 A1 | 2/2005 | Oral et al. |
| 2005/0040061 A1 | 2/2005 | Opie et al. |
| 2005/0075606 A1 | 4/2005 | Botich et al. |
| 2005/0107769 A1 | 5/2005 | Thommen |
| 2005/0119619 A1 | 6/2005 | Raining |
| 2005/0131350 A1 | 6/2005 | Shaw et al. |
| 2005/0165355 A1 | 7/2005 | Fitzgerald |
| 2005/0197623 A1 | 9/2005 | Leeflang et al. |
| 2005/0245847 A1 | 11/2005 | Schaeffer |
| 2005/0256505 A1 | 11/2005 | Long et al. |
| 2005/0273057 A1 | 12/2005 | Popov |
| 2006/0025721 A1 | 2/2006 | Duffy et al. |
| 2006/0079787 A1 | 4/2006 | Whiting et al. |
| 2006/0084964 A1 | 4/2006 | Knudson et al. |
| 2006/0155245 A1 | 7/2006 | Woehr |
| 2006/0167405 A1 | 7/2006 | King et al. |
| 2006/0229563 A1 | 10/2006 | O'Reagan et al. |
| 2006/0264834 A1 | 11/2006 | Vaillancourt |
| 2007/0043422 A1 | 2/2007 | Shmulewitz et al. |
| 2007/0060999 A1 | 3/2007 | Randall et al. |
| 2007/0083162 A1 | 4/2007 | O'Reagan et al. |
| 2007/0083188 A1 | 4/2007 | Grandt et al. |
| 2007/0100284 A1 | 5/2007 | Leinsing et al. |
| 2007/0123803 A1 | 5/2007 | Fujiwara et al. |
| 2007/0142779 A1 | 6/2007 | Duane et al. |
| 2007/0179446 A1 | 8/2007 | Carrez et al. |
| 2007/0191777 A1 | 8/2007 | King |
| 2007/0193903 A1 | 8/2007 | Opie et al. |
| 2007/0225647 A1 | 9/2007 | Luther et al. |
| 2007/0233007 A1 | 10/2007 | Adams |
| 2007/0244438 A1 | 10/2007 | Perez |
| 2007/0276288 A1 | 11/2007 | Khaw |
| 2008/0065011 A1 | 3/2008 | Marchand et al. |
| 2008/0097330 A1 | 4/2008 | King et al. |
| 2008/0108911 A1 | 5/2008 | Palmer |
| 2008/0108944 A1 | 5/2008 | Woehr et al. |
| 2008/0108974 A1 | 5/2008 | Yee Roth |
| 2008/0125709 A1 | 5/2008 | Chang et al. |
| 2008/0131300 A1 | 6/2008 | Junod et al. |
| 2008/0243165 A1 | 10/2008 | Mauch et al. |
| 2008/0262430 A1 | 10/2008 | Anderson et al. |
| 2008/0262431 A1 | 10/2008 | Anderson et al. |
| 2008/0294111 A1 | 11/2008 | Tal et al. |
| 2008/0300574 A1 | 12/2008 | Belson et al. |
| 2009/0018567 A1 | 1/2009 | Escudero et al. |
| 2009/0030380 A1 | 1/2009 | Binmoeller |
| 2009/0036836 A1 | 2/2009 | Nystrom et al. |
| 2009/0048566 A1 | 2/2009 | Ferguson et al. |
| 2009/0131872 A1 | 5/2009 | Popov |
| 2009/0157006 A1 | 6/2009 | Nardeo et al. |
| 2009/0221961 A1 | 9/2009 | Tal et al. |
| 2009/0292243 A1 | 11/2009 | Harding et al. |
| 2009/0299291 A1 | 12/2009 | Baid |
| 2010/0010447 A1 | 1/2010 | Luther et al. |
| 2010/0036331 A1 | 2/2010 | Sen |
| 2010/0056910 A1 | 3/2010 | Yanuma |
| 2010/0087787 A1 | 4/2010 | Woehr et al. |
| 2010/0094310 A1 | 4/2010 | Warring et al. |
| 2010/0168674 A1 | 7/2010 | Shaw et al. |
| 2010/0204654 A1 | 8/2010 | Mulholland et al. |
| 2010/0204660 A1 | 8/2010 | McKinnon et al. |
| 2010/0204675 A1 | 8/2010 | Woehr et al. |
| 2010/0210934 A1 | 8/2010 | Belson |
| 2010/0246707 A1 | 9/2010 | Michelitsch |
| 2010/0331732 A1 | 12/2010 | Raulerson et al. |
| 2011/0009827 A1 | 1/2011 | Bierman et al. |
| 2011/0015573 A1 | 1/2011 | Maan et al. |
| 2011/0021994 A1 | 1/2011 | Anderson et al. |
| 2011/0125097 A1 | 5/2011 | Shaw et al. |
| 2011/0137252 A1 | 6/2011 | Oster et al. |
| 2011/0196315 A1 | 8/2011 | Chappel |
| 2011/0207157 A1 | 8/2011 | Gautier et al. |
| 2011/0218496 A1 | 9/2011 | Bierman |
| 2011/0251559 A1 | 10/2011 | Tal et al. |
| 2011/0276002 A1 | 11/2011 | Bierman |
| 2011/0282285 A1 | 11/2011 | Blanchard et al. |
| 2011/0288482 A1 | 11/2011 | Farrell et al. |
| 2011/0306933 A1 | 12/2011 | Djordjevic et al. |
| 2011/0319838 A1 | 12/2011 | Goral et al. |
| 2012/0053523 A1 | 3/2012 | Harding |
| 2012/0071857 A1 | 3/2012 | Goldfarb et al. |
| 2012/0078231 A1 | 3/2012 | Hoshinouchi |
| 2012/0101440 A1 | 4/2012 | Kamen et al. |
| 2012/0123332 A1 | 5/2012 | Erskine |
| 2012/0157854 A1 | 6/2012 | Kurrus et al. |
| 2012/0184896 A1 | 7/2012 | DeLegge et al. |
| 2012/0197200 A1 | 8/2012 | Belson |
| 2012/0220942 A1 | 8/2012 | Hall et al. |
| 2012/0220956 A1 | 8/2012 | Kuracina et al. |
| 2012/0259293 A1 | 10/2012 | Bialecki et al. |
| 2012/0271232 A1 | 10/2012 | Katsurada et al. |
| 2012/0296282 A1 | 11/2012 | Koehler et al. |
| 2012/0316500 A1 | 12/2012 | Bierman et al. |
| 2012/0323181 A1 | 12/2012 | Shaw et al. |
| 2013/0204206 A1 | 8/2013 | Morgan et al. |
| 2013/0204226 A1 | 8/2013 | Keyser |
| 2013/0218082 A1 | 8/2013 | Hyer et al. |
| 2013/0304030 A1 | 11/2013 | Gray et al. |
| 2013/0324930 A1 | 12/2013 | Fuchs et al. |
| 2014/0012203 A1 | 1/2014 | Woehr et al. |
| 2014/0031752 A1 | 1/2014 | Blanchard et al. |
| 2014/0039461 A1 | 2/2014 | Anderson et al. |
| 2014/0058357 A1 | 2/2014 | Keyser et al. |
| 2014/0073928 A1 | 3/2014 | Yamashita et al. |
| 2014/0074034 A1 | 3/2014 | Tanabe et al. |
| 2014/0088509 A1 | 3/2014 | Sonderegger et al. |
| 2014/0094774 A1 | 4/2014 | Blanchard |
| 2014/0094836 A1 | 4/2014 | Feng et al. |
| 2014/0114239 A1 | 4/2014 | Dib et al. |
| 2014/0128775 A1 | 5/2014 | Andreae et al. |
| 2014/0135702 A1 | 5/2014 | Woehr et al. |
| 2014/0135703 A1 | 5/2014 | Yeh et al. |
| 2014/0180250 A1 | 6/2014 | Belson |
| 2014/0188003 A1 | 7/2014 | Belson |
| 2014/0194853 A1 | 7/2014 | Morgan et al. |
| 2014/0214005 A1 | 7/2014 | Belson |
| 2014/0221977 A1 | 8/2014 | Belson |
| 2014/0236099 A1 | 8/2014 | Nakagami et al. |
| 2014/0249488 A1 | 9/2014 | Woehr |
| 2014/0257359 A1 | 9/2014 | Tegels et al. |
| 2014/0276224 A1 | 9/2014 | Ranganathan et al. |
| 2014/0276434 A1 | 9/2014 | Woehr et al. |
| 2014/0336582 A1 | 11/2014 | Tisci et al. |
| 2014/0357983 A1 | 12/2014 | Toomey et al. |
| 2014/0364809 A1 | 12/2014 | Isaacson et al. |
| 2014/0371715 A1 | 12/2014 | Farrell et al. |
| 2014/0378867 A1 | 12/2014 | Belson |
| 2015/0025467 A1 | 1/2015 | Woehr |
| 2015/0038909 A1 | 2/2015 | Christensen et al. |
| 2015/0038910 A1 | 2/2015 | Harding et al. |
| 2015/0038943 A1 | 2/2015 | Warring et al. |
| 2015/0051584 A1 | 2/2015 | Korkuch et al. |
| 2015/0080801 A1 | 3/2015 | Tanabe et al. |
| 2015/0080810 A1 | 3/2015 | Henderson et al. |
| 2015/0088095 A1 | 3/2015 | Luther et al. |
| 2015/0119806 A1 | 4/2015 | Blanchard et al. |
| 2015/0119852 A1 | 4/2015 | Wexler |
| 2015/0126932 A1 | 5/2015 | Knutsson |
| 2015/0190168 A1 | 7/2015 | Bierman et al. |
| 2015/0190617 A1 | 7/2015 | Anderson et al. |
| 2015/0202414 A1 | 7/2015 | Hwang |
| 2015/0202421 A1 | 7/2015 | Ma et al. |
| 2015/0224267 A1 | 8/2015 | Farrell et al. |
| 2015/0231364 A1 | 8/2015 | Blanchard et al. |
| 2015/0290431 A1 | 10/2015 | Hall et al. |

(56) References Cited

U.S. PATENT DOCUMENTS

| | | |
|---|---|---|
| 2015/0306347 A1 | 10/2015 | Yagi |
| 2015/0306356 A1 | 10/2015 | Gill |
| 2015/0328434 A1 | 11/2015 | Gaur |
| 2015/0328438 A1 | 11/2015 | Baid |
| 2015/0359473 A1 | 12/2015 | Garrett et al. |
| 2016/0015943 A1 | 1/2016 | Belson et al. |
| 2016/0015945 A1 | 1/2016 | Warring et al. |
| 2016/0022963 A1 | 1/2016 | Belson |
| 2016/0256667 A1 | 9/2016 | Ribelin et al. |
| 2016/0331938 A1 | 11/2016 | Blanchard et al. |
| 2017/0035992 A1 | 2/2017 | Harding et al. |
| 2017/0087338 A1 | 3/2017 | Belson |
| 2017/0209668 A1 | 7/2017 | Belson |
| 2017/0259036 A1 | 9/2017 | Belson |
| 2017/0361071 A1 | 12/2017 | Belson |
| 2018/0028780 A1 | 2/2018 | Blanchard et al. |
| 2018/0071509 A1 | 3/2018 | Tran et al. |
| 2018/0126125 A1 | 5/2018 | Hall et al. |
| 2018/0133437 A1 | 5/2018 | Blanchard |
| 2018/0229003 A1 | 8/2018 | Blanchard et al. |
| 2018/0229004 A1 | 8/2018 | Blanchard et al. |
| 2019/0022358 A1 | 1/2019 | Belson |
| 2019/0192829 A1 | 6/2019 | Belson et al. |
| 2019/0201667 A1 | 7/2019 | Braithwaite et al. |
| 2019/0240459 A1 | 8/2019 | Belson |
| 2019/0275303 A1 | 9/2019 | Tran et al. |
| 2019/0307986 A1 | 10/2019 | Belson |
| 2019/0351193 A1 | 11/2019 | Hall |
| 2019/0351196 A1 | 11/2019 | Ribelin et al. |
| 2020/0001051 A1 | 1/2020 | Huang et al. |
| 2020/0094037 A1 | 3/2020 | Tran et al. |

FOREIGN PATENT DOCUMENTS

| | | | |
|---|---|---|---|
| CN | 1319023 | A | 10/2001 |
| CN | 1871043 | A | 11/2006 |
| CN | 101242868 | A | 8/2008 |
| CN | 101417159 | A | 4/2009 |
| CN | 101784300 | A | 7/2010 |
| CN | 102099075 | A | 6/2011 |
| CN | 102939129 | A | 2/2013 |
| CN | 105073174 | A | 11/2015 |
| CN | 105188826 | A | 12/2015 |
| CN | 105705191 | A | 6/2016 |
| DE | 20210394 | U1 | 9/2002 |
| EP | 0314470 | A2 | 5/1989 |
| EP | 417764 | A1 | 3/1991 |
| EP | 475857 | A1 | 3/1992 |
| EP | 515710 | A1 | 12/1992 |
| EP | 567321 | A2 | 10/1993 |
| EP | 652020 | A2 | 5/1995 |
| EP | 747075 | A2 | 12/1996 |
| EP | 750916 | A2 | 1/1997 |
| EP | 778043 | A1 | 6/1997 |
| EP | 800790 | A2 | 10/1997 |
| EP | 832663 | A2 | 4/1998 |
| EP | 910988 | A1 | 4/1999 |
| EP | 942761 | A1 | 9/1999 |
| EP | 1075850 | A2 | 2/2001 |
| EP | 1378263 | A2 | 1/2004 |
| EP | 1418971 | A2 | 5/2004 |
| EP | 1457229 | A1 | 9/2004 |
| EP | 1611916 | A1 | 1/2006 |
| EP | 1907042 | A2 | 4/2008 |
| EP | 2150304 | A2 | 2/2010 |
| EP | 2272432 | A1 | 1/2011 |
| EP | 2569046 | A1 | 3/2013 |
| JP | 2003-159334 | A | 6/2003 |
| JP | 2004-130074 | A | 4/2004 |
| JP | 2004-223252 | A | 8/2004 |
| JP | 2005-137888 | A | 6/2005 |
| JP | 2009-500129 | A | 1/2009 |
| JP | 2010-088521 | A | 4/2010 |
| JP | 2013-529111 | A | 7/2013 |
| WO | 83/01575 | A1 | 5/1983 |
| WO | 1983001575 | A1 | 5/1983 |
| WO | 1992013584 | A1 | 8/1992 |
| WO | 92/22344 | A1 | 12/1992 |
| WO | 1992022344 | A1 | 12/1992 |
| WO | 1995011710 | A1 | 5/1995 |
| WO | 95/19193 | A1 | 7/1995 |
| WO | 1995019193 | A1 | 7/1995 |
| WO | 95/23003 | A1 | 8/1995 |
| WO | 1995023003 | A1 | 8/1995 |
| WO | 96/32981 | A1 | 10/1996 |
| WO | 1996032981 | A1 | 10/1996 |
| WO | 1996040359 | A1 | 12/1996 |
| WO | 97/05912 | A2 | 2/1997 |
| WO | 1997005912 | A2 | 2/1997 |
| WO | 97/21458 | A1 | 6/1997 |
| WO | 1997021458 | A1 | 6/1997 |
| WO | 1997045151 | A1 | 12/1997 |
| WO | 98/24494 | A1 | 6/1998 |
| WO | 1998024494 | A1 | 6/1998 |
| WO | 1998030268 | A1 | 7/1998 |
| WO | 1998053875 | A1 | 12/1998 |
| WO | 1999008742 | A1 | 2/1999 |
| WO | 1999026682 | A1 | 6/1999 |
| WO | 00/06226 | A1 | 2/2000 |
| WO | 00/12160 | A1 | 3/2000 |
| WO | 2000012167 | A1 | 3/2000 |
| WO | 00/47256 | A1 | 8/2000 |
| WO | 2001007103 | A1 | 2/2001 |
| WO | 2002041932 | A2 | 5/2002 |
| WO | 02/066093 | A2 | 8/2002 |
| WO | 03/11381 | A1 | 2/2003 |
| WO | 03/43686 | A1 | 5/2003 |
| WO | 03/043686 | A1 | 5/2003 |
| WO | 03/47675 | A2 | 6/2003 |
| WO | 03/047675 | A2 | 6/2003 |
| WO | 2004/018031 | A2 | 3/2004 |
| WO | 2004106203 | A3 | 12/2004 |
| WO | 2005002659 | A1 | 1/2005 |
| WO | 2005/074412 | A2 | 8/2005 |
| WO | 2005/087306 | A1 | 9/2005 |
| WO | 2006062996 | A2 | 6/2006 |
| WO | 2007006055 | A2 | 1/2007 |
| WO | 2007/032343 | A1 | 3/2007 |
| WO | 2007094841 | A1 | 8/2007 |
| WO | 2007098355 | A1 | 8/2007 |
| WO | 2007098359 | A1 | 8/2007 |
| WO | 2008005618 | A2 | 1/2008 |
| WO | 2008030999 | A2 | 3/2008 |
| WO | 2008/131300 | A2 | 10/2008 |
| WO | 2008137956 | A2 | 11/2008 |
| WO | 2009/001309 | A1 | 12/2008 |
| WO | 2008147600 | A2 | 12/2008 |
| WO | 2009031161 | A1 | 3/2009 |
| WO | 2009114837 | A2 | 9/2009 |
| WO | 2009/124990 | A1 | 10/2009 |
| WO | 2010015676 | A1 | 2/2010 |
| WO | 2010/048449 | A2 | 4/2010 |
| WO | 2010/132608 | A2 | 11/2010 |
| WO | 2011036574 | A1 | 3/2011 |
| WO | 2011143621 | A1 | 11/2011 |
| WO | 2012106266 | A1 | 8/2012 |
| WO | 2012154277 | A1 | 11/2012 |
| WO | 2012174109 | A1 | 12/2012 |
| WO | 2013119557 | A1 | 8/2013 |
| WO | 2013126446 | A1 | 8/2013 |
| WO | 2013187827 | A1 | 12/2013 |
| WO | 2014006403 | A1 | 1/2014 |
| WO | 2014029424 | A1 | 2/2014 |
| WO | 2014074417 | A1 | 5/2014 |
| WO | 2014081942 | A1 | 5/2014 |
| WO | 2014133617 | A1 | 9/2014 |
| WO | 2014165783 | A1 | 10/2014 |
| WO | 2015035393 | A1 | 3/2015 |
| WO | 15108913 | A1 | 7/2015 |
| WO | 2015/168655 | A2 | 11/2015 |
| WO | 15164912 | A1 | 11/2015 |

(56) References Cited

FOREIGN PATENT DOCUMENTS

| | | |
|---|---|---|
| WO | 2016/037127 A1 | 3/2016 |
| WO | 2019173641 A1 | 9/2019 |

OTHER PUBLICATIONS

Access Scientific, The PICC Wand® Product Data Sheet, Revision F, May 22, 2012.
Access Scientific, The Powerwand® Extended Dwell Catheter Brochure (http://accessscientific.com/media/4Fr-POWERWAND-Brochure.pdf) last accessed Sep. 25, 2015.
BD Angiocath™ Autoguard™ Shielded IV Catheter Brochure, © 2001.
BD Medical Systems, I.V. Catheter Family Brochure (2006).
BD Saf-T-Intimalm Integrated Safety IV Catheter Brochure, © 2001.
Becton Dickinson, Insyte® AutoGuardlm Shielded I.V. Catheter Brochure, 1998.
CN 201180029526.7 filed Dec. 14, 2012 First Office Action dated Apr. 21, 2014.
CN 201280008866.6 filed Aug. 14, 2013 Second Office Action dated Aug. 17, 2015.
CN 201280008866.6 filed Aug. 14, 2013 First Office Action dated Dec. 31, 2014.
CN 201280008866.6 filed Aug. 14, 2013 Third Office Action dated Jan. 25, 2016.
EP 10075422.5 filed Jul. 5, 2008 European search report and written opinion dated Dec. 1, 2010.
Hadaway, Lynn C., A Midline Alternative to Central and Peripheral Venous Access, Caring Magazine, May 1990, pp. 45-50.
JP 2013-510353 filed Oct. 31, 2012 First Office Action dated Feb. 19, 2015.
JP 2013-510353 filed Oct. 31, 2012 Second Office Action dated Jan. 28, 2016.
Menlo Care, Landmark™ Aquavene® Catheters Brochure, 1992.
Menlo Care, Landmark® Midline Catheter Maintenance and Reference Guide (1993).
Menlo Care, Landmark® Midline Catheters Brochure, 1991.
Menlo Care, Landmark® Venous Access Device Insertion Instructions (1992).
Menlo Care, Publications on Aquavene® Technology, Aug. 1992.
PCT/US2008/062954 filed May 7, 2008 International search report and written opinion dated Jan. 16, 2009.
PCT/US2011/036530 filed May 13, 2011 International Search Report dated Oct. 6, 2011.
PCT/US2011/036530 filed May 13, 2011 Written Opinion of the International Searching Authority dated Oct. 6, 2011.
PCT/US2012/026618 International Preliminary Report on Patentability dated Aug. 27, 2013.
PCT/US2012/026618 International Search Report and Written Opinion dated Jun. 25, 2012.
PCT/US2013/073577 filed Dec. 6, 2013 International Search Report and Written Opinion dated Feb. 24, 2014.
PCT/US2014/013557 filed International search report and written opinion dated Jan. 29, 2014.
PR Newswire, Luther Medical Products, Inc. Receives Approval to Supply Improved Neonatal Product to Japan, Aug. 20, 1998.
Rasor, Julia S, Review of Catheter-related infection rates: comparison of conventional catheter materials with Aquavene®, JVAN vol. 1, No. 3, Spring 1991.
U.S. Appl. No. 12/598,053, filed Apr. 20, 2010 Notice of allowance dated Jan. 16, 2014.
U.S. Appl. No. 12/598,053, filed Apr. 20, 2010 Office action dated Aug. 28, 2013.
U.S. Appl. No. 12/598,053, filed Apr. 20, 2010 Office action dated Dec. 4, 2012.
U.S. Appl. No. 12/598,053, filed Apr. 20, 2010 Office action dated May 8, 2013.
U.S. Appl. No. 12/598,053, filed Apr. 20, 2010 Office action dated Oct. 24, 2013.
U.S. Appl. No. 13/107,781, filed May 13, 2011 Final Office Action dated Jul. 18, 2014.
U.S. Appl. No. 13/107,781, filed May 13, 2011 Non-Final Office Action dated Dec. 30, 2013.
U.S. Appl. No. 13/405,096, filed Feb. 24, 2012 Advisory Action dated Apr. 18, 2014.
U.S. Appl. No. 13/405,096, filed Feb. 24, 2012 Final Office Action dated Jan. 31, 2014.
U.S. Appl. No. 13/405,096, filed Feb. 24, 2012 Non-Final Office Action dated Aug. 20, 2013.
U.S. Appl. No. 13/405,096, filed Feb. 24, 2012 Non-Final Office Action dated Nov. 18, 2014.
U.S. Appl. No. 13/405,096, filed Feb. 24, 2012 Notice of Allowance dated Mar. 11, 2015.
U.S. Appl. No. 14/044,623, filed Oct. 2, 2013 Notice of Allowance dated Nov. 6, 2014.
U.S. Appl. No. 14/099,050, filed Dec. 6, 2013 Non-Final Office Action dated Dec. 22, 2015.
U.S. Appl. No. 14/167,149, filed Jan. 29, 2014 Non-Final Office Action dated Oct. 21, 2015.
U.S. Appl. No. 14/174,071, filed Feb. 6, 2014 Restriction Requirement dated Dec. 7, 2015.
U.S. Appl. No. 14/477,717, filed Sep. 4, 2014, Notice of allowance dated Feb. 17, 2015.
U.S. Appl. No. 14/477,717, filed Sep. 4, 2014, Office action dated Dec. 18, 2014.
U.S. Appl. No. 14/585,800, filed Dec. 30, 2014 Non-Final Office Action dated Oct. 8, 2015.
U.S. Appl. No. 14/866,441, filed Sep. 25, 2015 Non-Final Office Action dated Mar. 14, 2016.
Waltimire, B. and Rasor, J.S., Midline catheter: Virtually bloodless insertion technique and needle safety tube minimize potential for transmission of bloodborne disease. Sponsored by national Foundation for Infectious Diseases. 5th National forum on AIDS, Hepatitis, and other blood-borne diseases. Atlanta, GA, Mar. 1992.
Cook Medical "Lunderquist Extra-Stiff wire guide" (2012).
Endovascular Today "Coiled Stainless Steel Guidewires" Buyer's Guide pp. 13-20, (2012).
European office action dated Apr. 21, 2008 for EP Application No. 06800027.2.
European office action dated Aug. 6, 2012 for EP Application No. 07783404.2.
European office action dated Oct. 5, 2010 for EP Application No. 07783404.2.
European search report and opinion dated Jul. 10, 2009 for EP Application No. 07783404.2.
International search report and written opinion dated Jun. 1, 2007 for PCT/US2006/026671.
International search report and written opinion dated Oct. 23, 2008 for PCT/US2007/068393.
Notice of allowance dated Jan. 29, 2014 for U.S. Appl. No. 12/307,519.
Notice of allowance dated Jun. 10, 2015 for U.S. Appl. No. 11/577,491.
Office action dated Mar. 10, 2011 for U.S. Appl. No. 12/307,519.
Office action dated Mar. 15, 2011 for U.S. Appl. No. 11/577,491.
Office action dated Aug. 2, 2010 for U.S. Appl. No. 11/577,491.
Office action dated Aug. 18, 2014 for U.S. Appl. No. 11/577,491.
Office action dated Oct. 25, 2010 for U.S. Appl. No. 12/307,519.
Office action dated Nov. 4, 2013 for U.S. Appl. No. 12/307,519.
Office action dated Mar. 12, 2015 for U.S. Appl. No. 11/577,491.
CN 201510079782.7 filed Feb. 13, 2015 Office Action dated Dec. 30, 2016.
JP 2013-510353 filed Oct. 31, 2012 Office Action dated Dec. 15, 2016.
PCT/US2016/032449 filed May 13, 2016 International Search Report and Written Opinion dated Oct. 5, 2016.
PCT/US2016/032534 filed May 13, 2016 International Search Report and Written Opinion dated Oct. 5, 2016.
U.S. Appl. No. 14/099,050, filed Dec. 6, 2013 Final Office Action dated Jan. 30, 2017.

(56) References Cited

OTHER PUBLICATIONS

U.S. Appl. No. 14/174,071, filed Feb. 6, 2014 Final Office Action dated Dec. 2, 2016.
U.S. Appl. No. 14/192,541, filed Feb. 27, 2014 Notice of Allowance dated Dec. 6, 2016.
U.S. Appl. No. 14/250,093, filed Apr. 10, 2014 Non-Final Office Action dated Nov. 16, 2016.
U.S. Appl. No. 14/585,800, filed Dec. 30, 2014 Non-Final Office Action dated Nov. 29, 2016.
U.S. Appl. No. 14/866,441, filed Sep. 25, 2015 Advisory Action dated Dec. 22, 2016.
EP 12782187.4 filed Sep. 10, 2013 European search report and written opinion dated Aug. 30, 2016.
EP 12782187.4 filed Sep. 10, 2013 European search report and written opinion dated Dec. 17, 2015.
EP 13876666.2 filed Sep. 7, 2015 Extended European Search Report dated Sep. 20, 2016.
International search report and written opinion dated Apr. 2, 2012 for PCT/US2012/023192.
JP 2016-107046 filed May 30, 2016 Office Action dated Jul. 28, 2016.
Office action dated Mar. 27, 2013 for U.S. Appl. No. 13/358,099.
PCT/US15/28950 filed May 1, 2015 International Search Report and Written Opinion dated Oct. 19, 2015.
PCT/US2015/048676 filed Sep. 4, 2015 International search report and written opinion dated Dec. 4, 2015.
U.S. Appl. No. 14/099,050, filed Dec. 6, 2013 Non-Final Office Action dated Jul. 19, 2016.
U.S. Appl. No. 14/167,149, filed Jan. 29, 2014 Notice of Allowance dated Jul. 6, 2016.
U.S. Appl. No. 14/174,071, filed Feb. 6, 2014 Non-Final Office Action dated Jul. 29, 2016.
U.S. Appl. No. 14/174,071, filed Feb. 6, 2014 Non-Final Office Action dated Mar. 31, 2016.
U.S. Appl. No. 14/192,541, filed Feb. 27, 2014 Non-Final Office Action dated Jul. 20, 2016.
U.S. Appl. No. 14/585,800, filed Dec. 30, 2014 Non-Final Office Action dated May 16, 2016.
U.S. Appl. No. 14/866,441, filed Sep. 25, 2015 Final Office Action dated Sep. 23, 2016.
CN 201510079782.7 filed Feb. 13, 2015 Office Action dated Sep. 19, 2017.
JP 2015-560173 filed Aug. 28, 2015 Office Action dated Sep. 19, 2017.
U.S. Appl. No. 14/099,050, filed Dec. 6, 2013 Notice of Allowance dated Sep. 14, 2017.
U.S. Appl. No. 14/099,050, filed Dec. 6, 2013 Notice of Panel Decision dated Aug. 1, 2017.
U.S. Appl. No. 14/702,580, filed May 1, 2015 Final Office Action dated Sep. 1, 2017.
U.S. Appl. No. 14/846,387, filed Sep. 4, 2015 Non-Final Office Action dated Sep. 22, 2017.
U.S. Appl. No. 29/536,043, filed Aug. 12, 2015 Non-Final Office Action dated Aug. 31, 2017.
U.S. Appl. No. 29/545,436, filed Nov. 12, 2015 Non-Final Office Action dated Sep. 12, 2017.
U.S. Appl. No. 14/192,541, filed Feb. 27, 2014 Notice of Corrected Allowability dated Mar. 8, 2017.
U.S. Appl. No. 14/250,093, filed Apr. 10, 2014 Final Office Action dated Mar. 9, 2017.
U.S. Appl. No. 14/750,658, filed Jun. 25, 2016 Non-Final Office Action dated Mar. 9, 2017.
U.S. Appl. No. 14/866,441, filed Sep. 25, 2015 Non-Final Office Action dated Apr. 7, 2017.
U.S. Appl. No. 14/876,735, filed Oct. 6, 2015 Non-Final Office Action dated Mar. 30, 2017.
CA 2,799,360 filed May 13, 2011 Office Action dated Jun. 7, 2017.
JP 2016-107046 filed May 30, 2016 Office Action dated Apr. 26, 2017.
U.S. Appl. No. 14/099,050, filed Dec. 6, 2013 Advisory Action dated Jun. 1, 2017.
U.S. Appl. No. 14/250,093, filed Apr. 10, 2014 Advisory Action dated May 19, 2017.
U.S. Appl. No. 14/250,093, filed Apr. 10, 2014 Panel Decision dated Jul. 14, 2017.
U.S. Appl. No. 14/585,800, filed Dec. 30, 2014 Notice of Allowance dated Jul. 3, 2017.
U.S. Appl. No. 14/702,580, filed May 1, 2015 Non-Final Office Action dated May 3, 2017.
U.S. Appl. No. 14/750,658, filed Jun. 25, 2016 Notice of Allowance dated Jul. 20, 2017.
EP17849786.3 filed Apr. 12, 2019 Extended European Search Report dated May 13, 2020.
U.S. Appl. No. 14/250,093, filed Apr. 10, 2014 Patent Board Decision dated Jun. 8, 2020.
U.S. Appl. No. 15/154,384, filed May 13, 2016 Non-Final Office Action dated Jun. 26, 2020.
U.S. Appl. No. 15/862,380, filed Jan. 4, 2018 Non-Final Office Action dated Jul. 9, 2020.
U.S. Appl. No. 15/869,872, filed Jan. 12, 2018 Final Office Action dated Jun. 25, 2020.
U.S. Appl. No. 16/292,076, filed Mar. 4, 2019 Non-Final Office Action dated Aug. 10, 2020.
U.S. Appl. No. 29/658,136, filed Jul. 27, 2018 Restriction Requirement dated May 11, 2020.
EP 19181963.0 filed Jun. 24, 2019 Extended European Search Report dated Jul. 16, 2019.
U.S. Appl. No. 15/702,537, filed Sep. 12, 2017 Notice of Allowance dated Jul. 31, 2019.
U.S. Appl. No. 15/727,528, filed Oct. 6, 2017 Non-Final Office Action dated Sep. 20, 2019.
U.S. Appl. No. 15/727,528, filed Oct. 6, 2017 Restriction Requirement dated Aug. 7, 2019.
EP 16797029.2 filed Nov. 21, 2017 Office Action dated Mar. 27, 2020.
U.S. Appl. No. 15/727,528, filed Oct. 6, 2017 Final Office Action dated Jan. 28, 2020.
U.S. Appl. No. 15/727,528, filed Oct. 6, 2017 Notice of Allowance dated Mar. 27, 2020.
U.S. Appl. No. 15/869,872, filed Jan. 12, 2018 Non-Final Office Action dated Apr. 10, 2020.
U.S. Appl. No. 15/951,931, filed Apr. 12, 2018 Notice of Allowance dated Feb. 20, 2020.
U.S. Appl. No. 15/951,931, filed Apr. 12, 2018 Notice of Allowability dated Apr. 16, 2020.
U.S. Appl. No. 15/951,954, filed Apr. 12, 2018 Notice of Allowance dated Feb. 23, 2020.
U.S. Appl. No. 15/951,954, filed Apr. 12, 2018 Notice of Allowability dated Apr. 7, 2020.
U.S. Appl. No. 16/138,523, filed Sep. 21, 2018 Notice of Allowance dated Mar. 26, 2020.
U.S. Appl. No. 29/654,521, filed Jun. 25, 2018 Restriction Requirement dated Apr. 8, 2020.
U.S. Appl. No. 29/654,527, filed Jun. 25, 2018 Restriction Requirement dated Mar. 10, 2020.
EP 12782187.4 filed Sep. 10, 2013 Office Action dated Nov. 28, 2018.
SG 11201709185X filed Nov. 8, 2017 Office Action dated Oct. 5, 2018.
SG 11201709193S filed Nov. 8, 2017 Office Action dated Oct. 5, 2018.
U.S. Appl. No. 15/702,537, filed Sep. 12, 2017 Non-Final Office Action dated Nov. 29, 2018.
EP 16797047.4 filed Dec. 6, 2017 Supplemental European Search Report dated Jan. 9, 2019.
JP 2016-563441 filed Oct. 19, 2016 Office Action dated Jan. 25, 2019.
U.S. Appl. No. 14/585,800, filed Dec. 30, 2014 Notice of Allowance dated Feb. 25, 2019.
U.S. Appl. No. 15/154,384, filed May 13, 2016 Restriction Requirement dated Jan. 25, 2019.

(56) References Cited

OTHER PUBLICATIONS

U.S. Appl. No. 15/481,773, filed Apr. 7, 2017 Final Office Action dated Jan. 10, 2019.
U.S. Appl. No. 151/02,537, filed Sep. 12, 2017 Final Office Action dated Mar. 8, 2019.
U.S. Appl. No. 15/154,384, filed May 13, 2016 Final Office Action dated Nov. 27, 2019.
U.S. Appl. No. 15/862,380, filed Jan. 4, 2018 Restriction Requirement dated Dec. 23, 2019.
U.S. Appl. No. 15/951,931, filed Apr. 12, 2018 Non-Final Office Action dated Nov. 19, 2019.
U.S. Appl. No. 15/951,954, filed Apr. 12, 2018 Non-Final Office Action dated Nov. 4, 2019.
JP 2015-560173 filed Aug. 28, 2015 Office Action dated Aug. 2, 2018.
U.S. Appl. No. 14/846,387, filed Sep. 4, 2015 Notice of Allowance dated Oct. 29, 2018.
U.S. Appl. No. 14/866,441, filed Sep. 25, 2015 Notice of Allowance dated Oct. 17, 2018.
U.S. Appl. No. 15/154,808, filed May 13, 2016 Advisory Action dated Oct. 26, 2018.
U.S. Appl. No. 15/154,808, filed May 13, 2016 Final Office Action dated Aug. 16, 2018.
U.S. Appl. No. 15/377,880, filed Dec. 13, 2016 Final Office Action dated Oct. 19, 2018.
CN 201380073657.4 filed Aug. 21, 2015 Office Action dated Mar. 2, 2018.
CN 201510079782.7 filed Feb. 13, 2015 Office Action dated Feb. 5, 2018.
EP 07783404.2 filed Jan. 19, 2009 Office Action dated Mar. 7, 2018.
EP 12782187.4 filed Sep. 10, 2013 Office Action dated Apr. 24, 2018.
RU 2017141812 filed Nov. 30, 2017 Office Action dated Jan. 31, 2018.
U.S. Appl. No. 14/846,387, filed Sep. 4, 2015 Final Office Action dated Mar. 22, 2018.
U.S. Appl. No. 15/154,808, filed May 13, 2016 Non-Final Office Action dated Apr. 6, 2018.
U.S. Appl. No. 29/536,043, filed Aug. 12, 2015 Final Office Action dated Mar. 26, 2018.
U.S. Appl. No. 29/545,436, filed Nov. 12, 2015 Final Office Action dated Mar. 26, 2018.
EP 16797029.2 filed Nov. 21, 2017 Extended European Search Report dated May 3, 2018.
U.S. Appl. No. 14/250,093, filed Apr. 10, 2014 Examiner's Answer dated Jun. 20, 2018.
U.S. Appl. No. 14/585,800, filed Dec. 30, 2014 Final Office Action dated May 11, 2018.
U.S. Appl. No. 14/846,387, filed Sep. 4, 2015 Advisory Action dated May 10, 2018.
U.S. Appl. No. 14/866,441, filed Sep. 25, 2015 Final Office Action dated Jun. 5, 2018.
U.S. Appl. No. 15/377,880, filed Dec. 13, 2016 Non-Final Office Action dated May 14, 2018.
U.S. Appl. No. 15/481,773, filed Apr. 7, 2017 Non-Final Office Action dated Jun. 29, 2018.
CN 201380073657.4 filed Aug. 21, 2015 Office Action dated Jun. 28, 2017.
EP 11781384.0 filed Sep. 21, 2012 Extended European Search Report dated Oct. 31, 2017.
EP 15785819.2 filed Dec. 2, 2016 Extended European Search Report dated Dec. 4, 2017.
JP 2016-107046 filed May 30, 2016 Office Action dated Nov. 7, 2017.
PCT/CN2017/075370 filed Mar. 1, 2017 International Search Report and Written Opinion dated Nov. 30, 2017.
U.S. Appl. No. 14/250,093, filed Apr. 10, 2014 Final Office Action dated Nov. 6, 2017.
U.S. Appl. No. 14/585,800, filed Dec. 30, 2014 Non-Final Office Action dated Nov. 3, 2017.
U.S. Appl. No. 14/702,580, filed May 1, 2015 Advisory Action dated Nov. 13, 2017.
U.S. Appl. No. 14/702,580, filed May 1, 2015 Notice of Allowance dated Dec. 8, 2017.
U.S. Appl. No. 15/154,808, filed May 13, 2016 Restriction Requirement dated Jan. 3, 2018.
U.S. Appl. No. 15/692,915, filed Aug. 31, 2017 Non-Final Office Action dated Jan. 29, 2018.

* cited by examiner

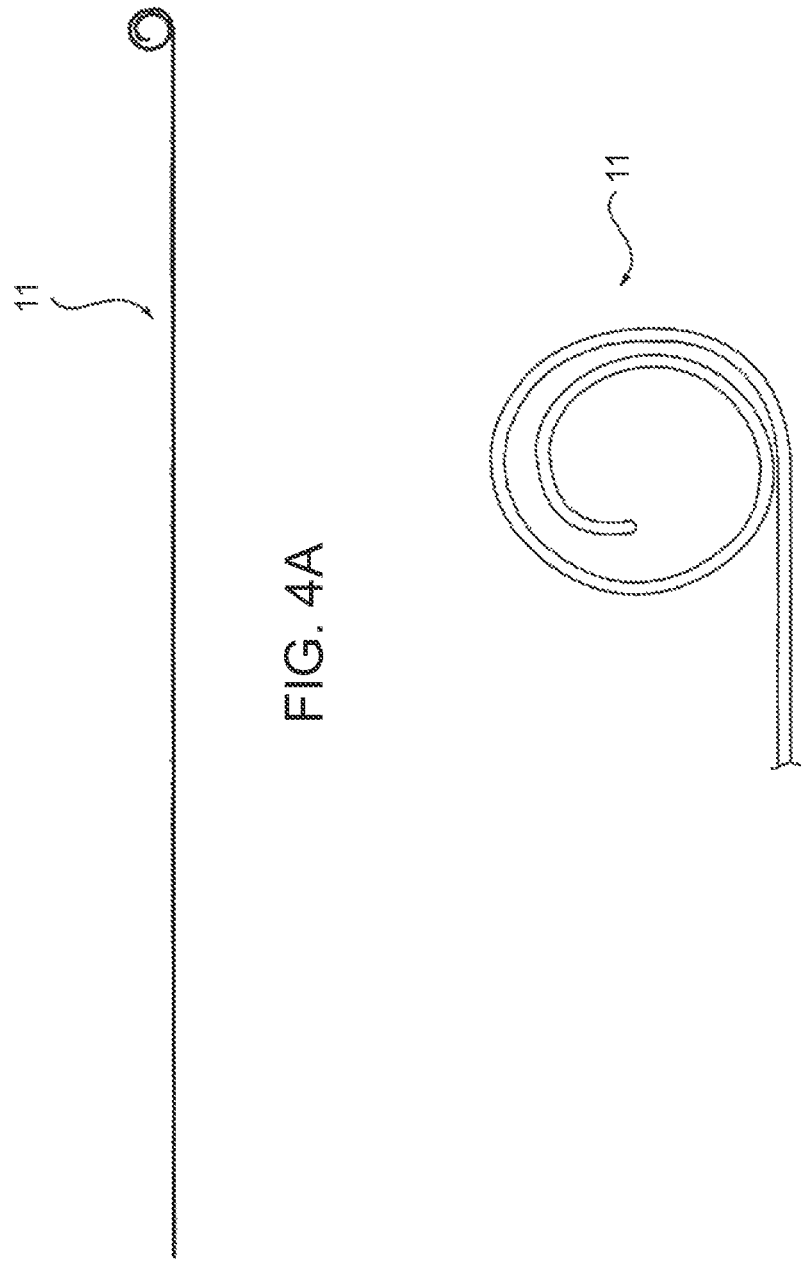
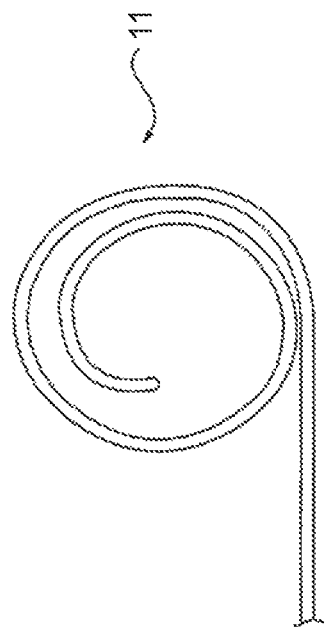
FIG. 4A
FIG. 4B

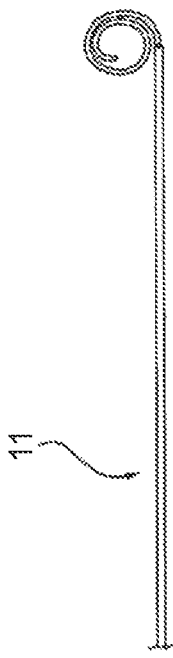
FIG. 5A
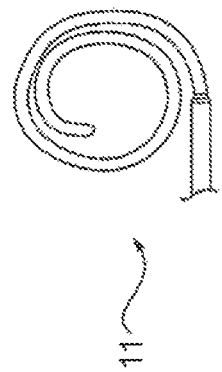
FIG. 5B
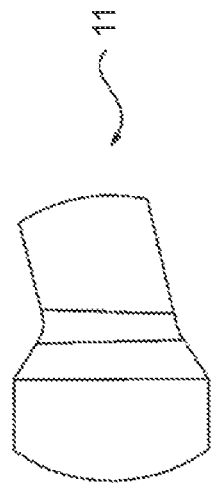
FIG. 5C

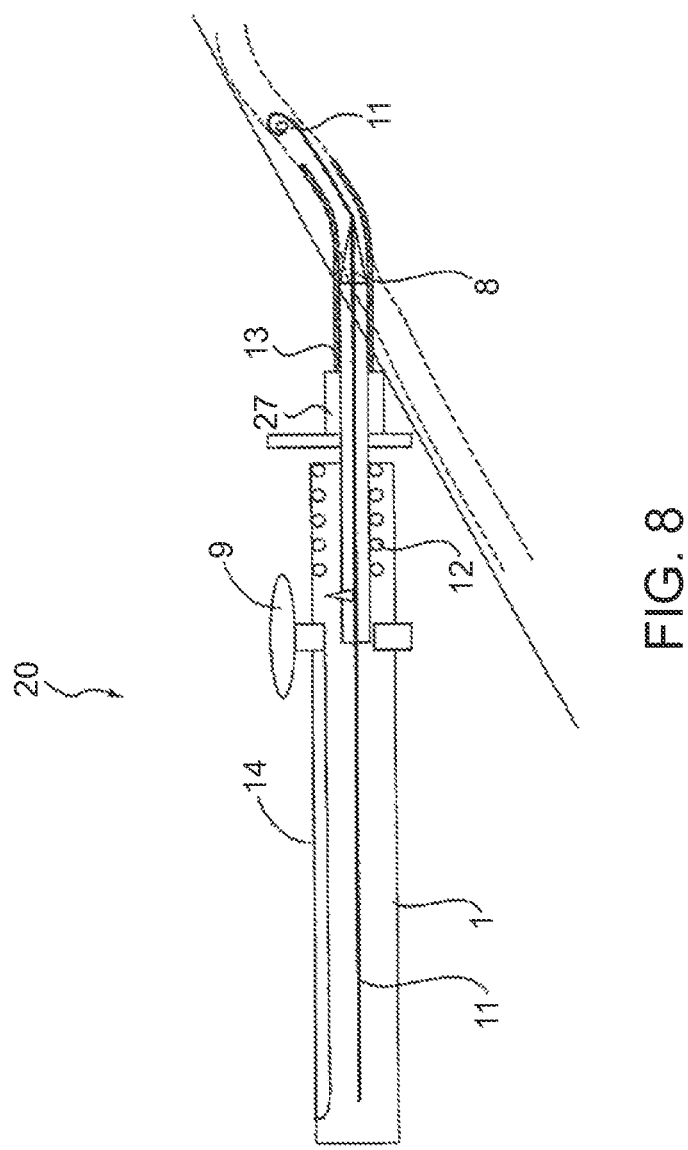

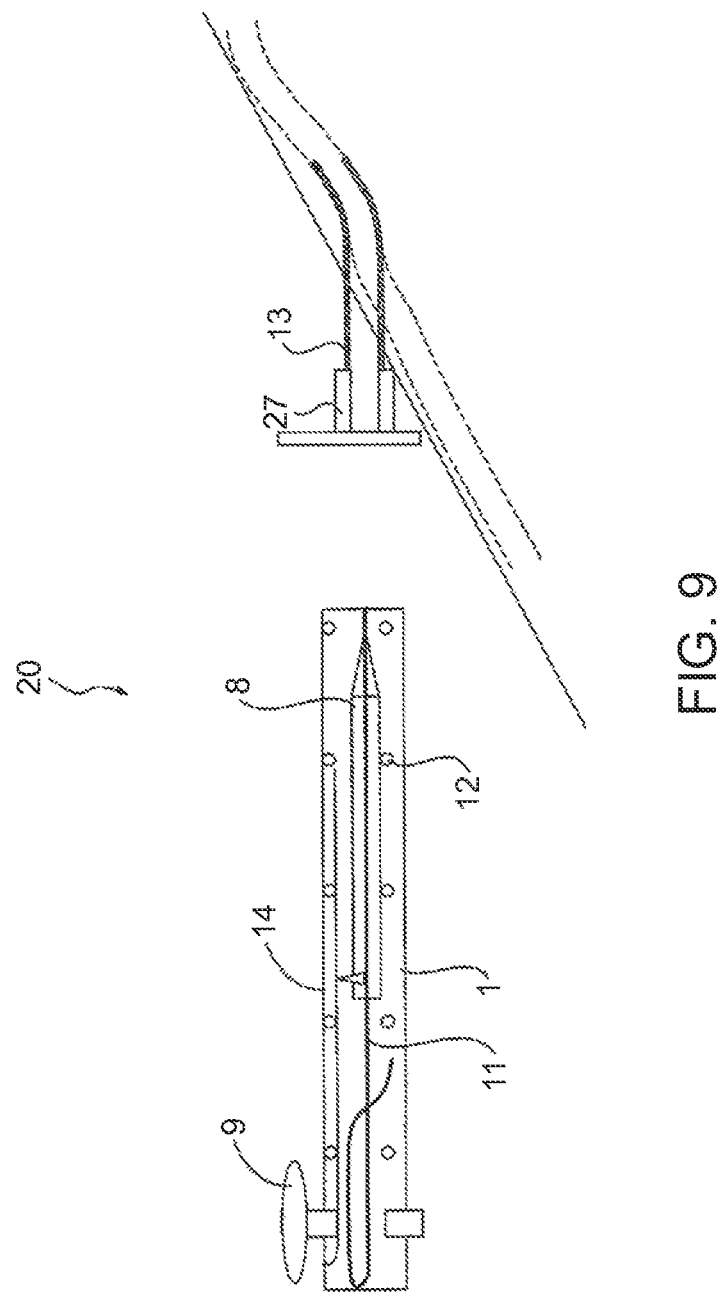

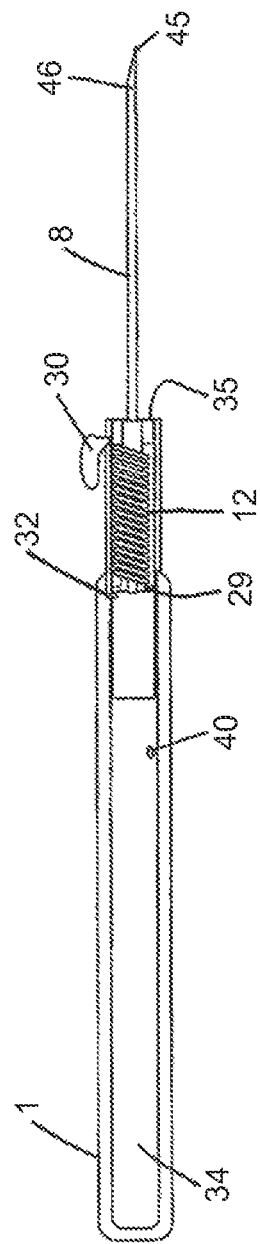
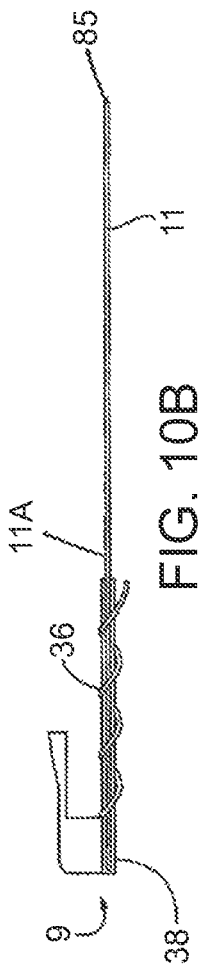
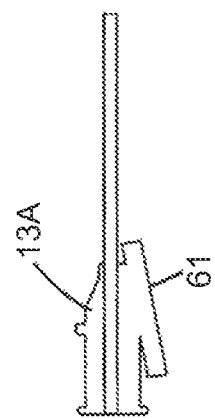
FIG. 10A
FIG. 10B
FIG. 10C
FIG. 10D

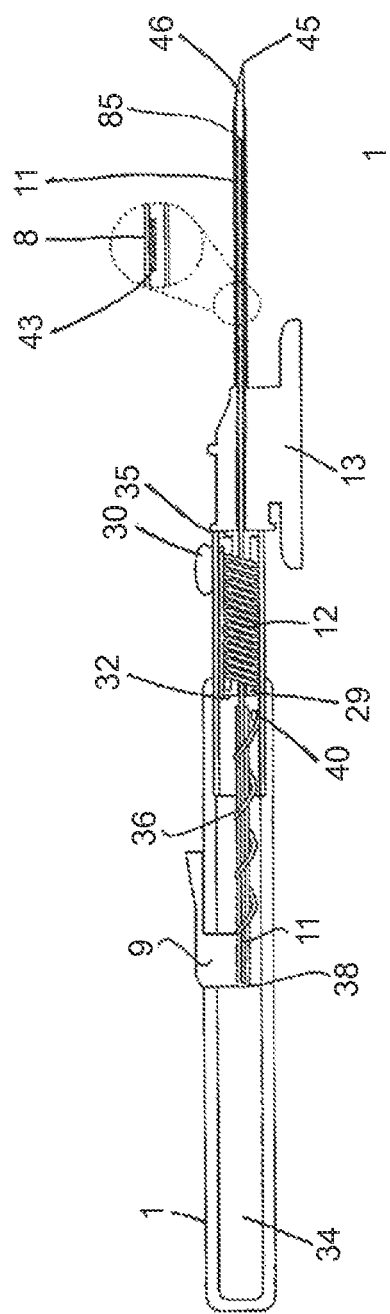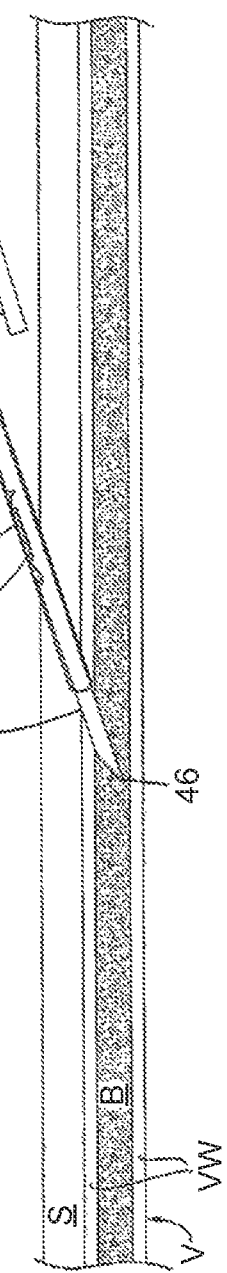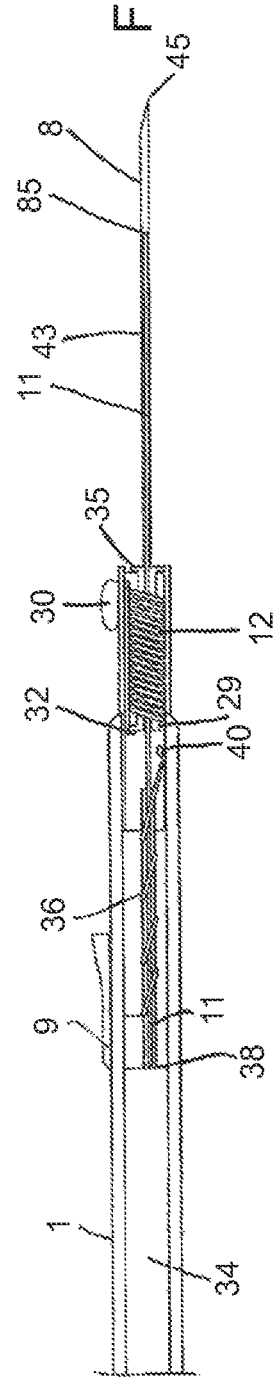

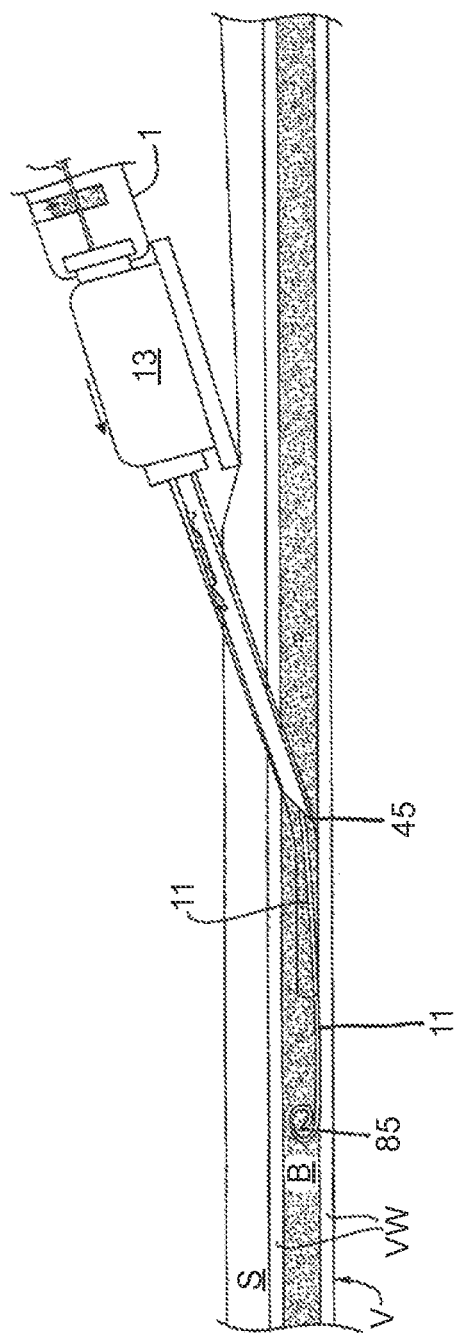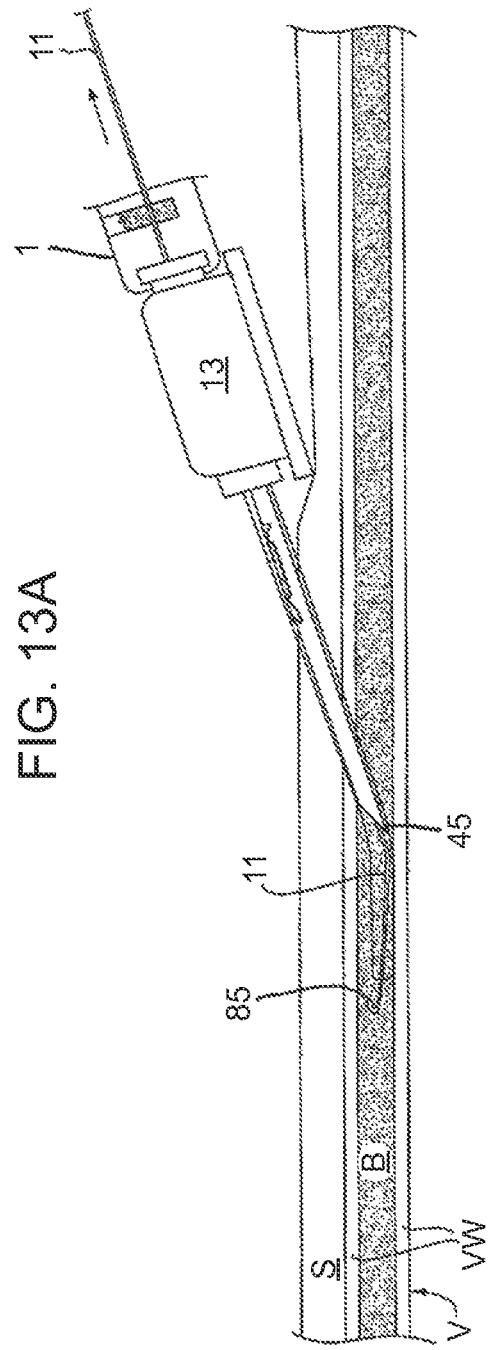

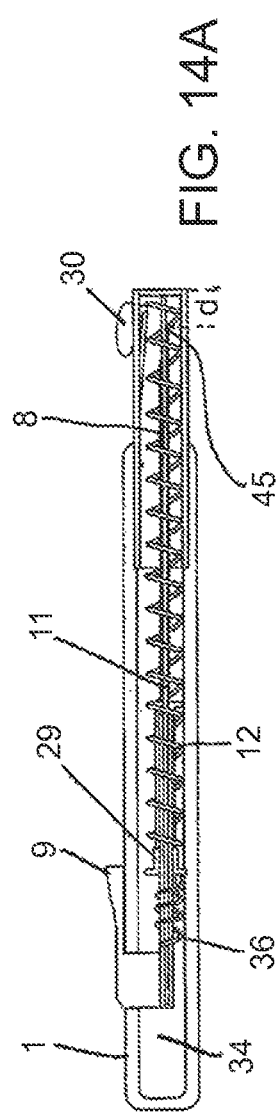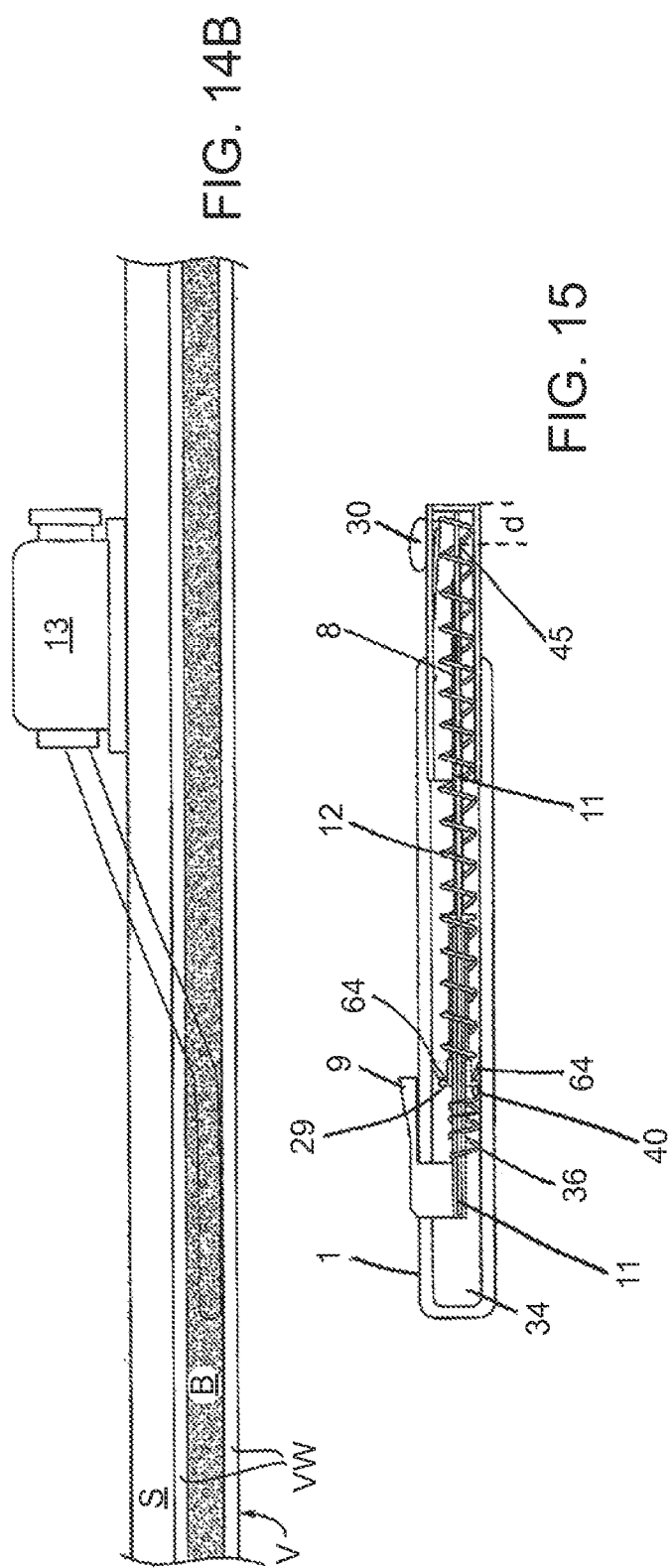

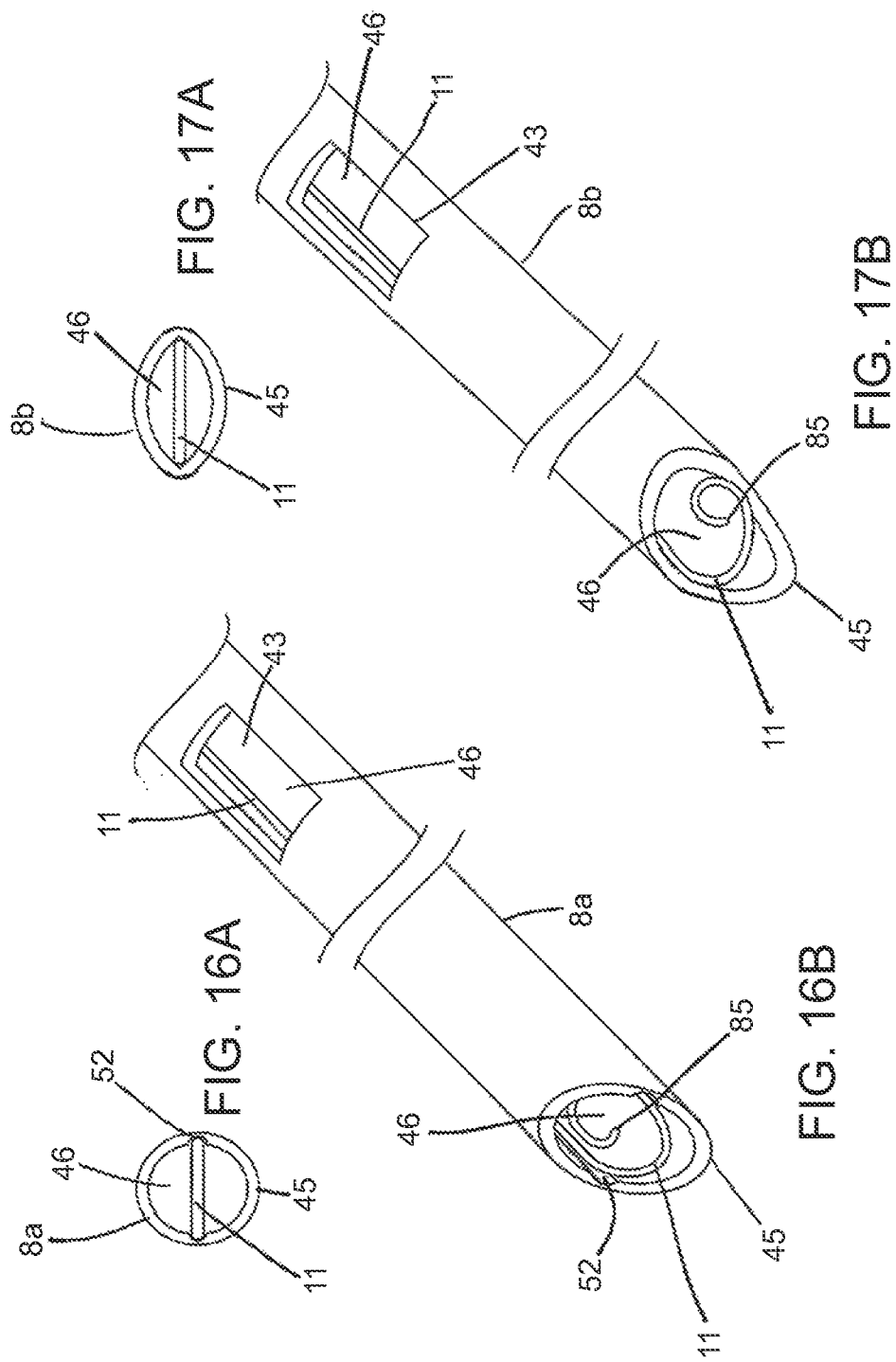

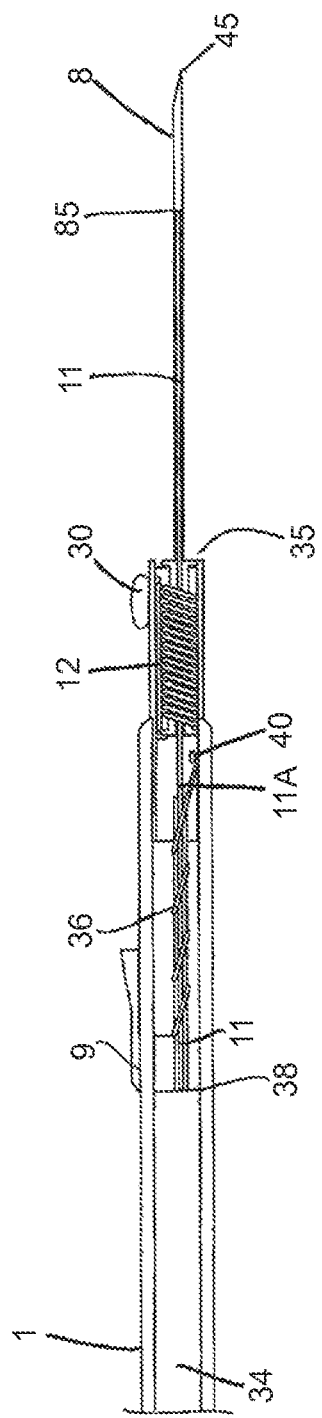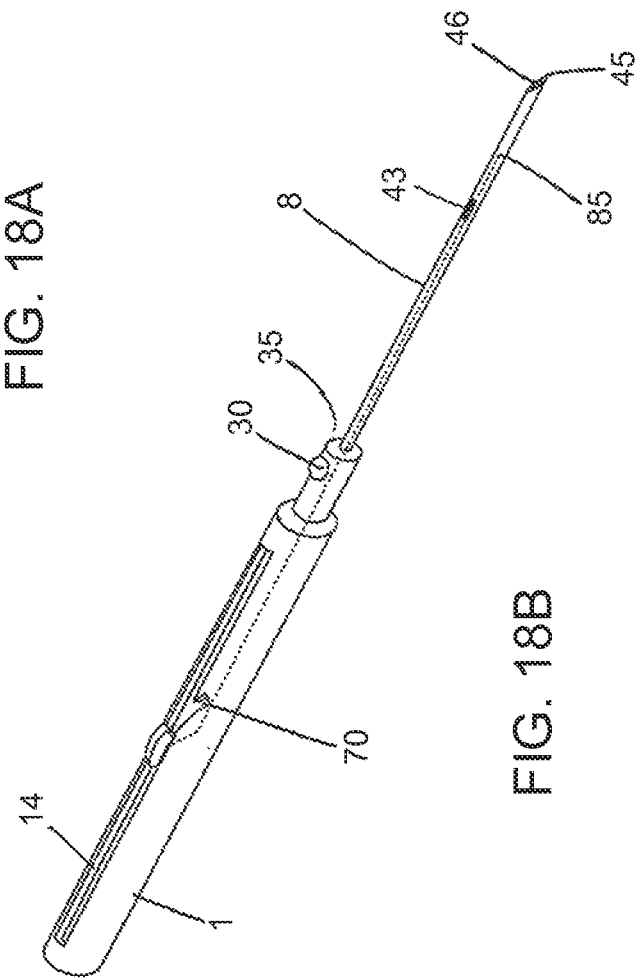
FIG. 18A
FIG. 18B

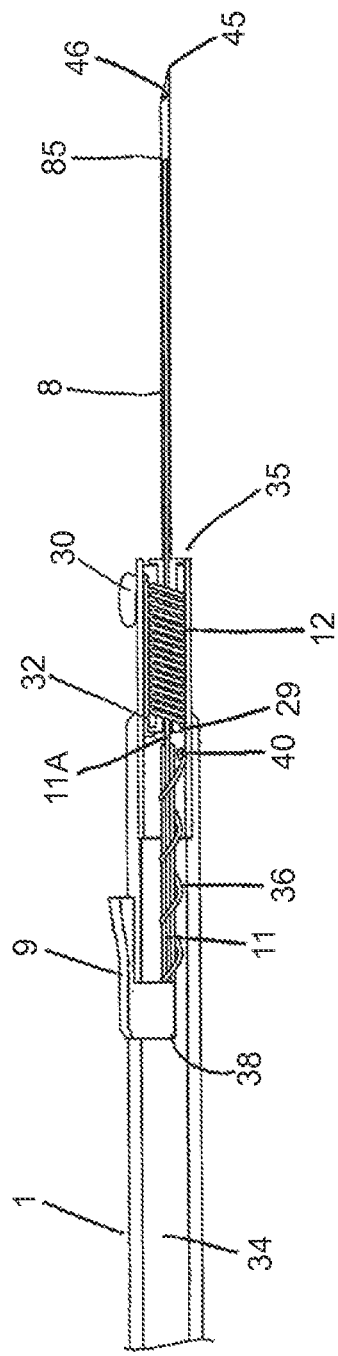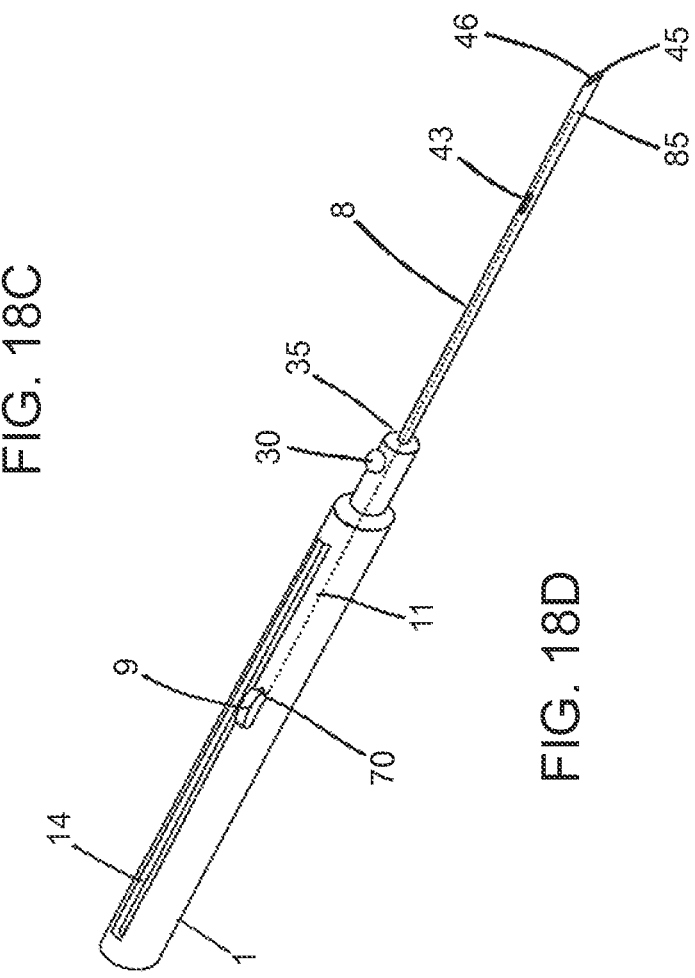
FIG. 18C
FIG. 18D

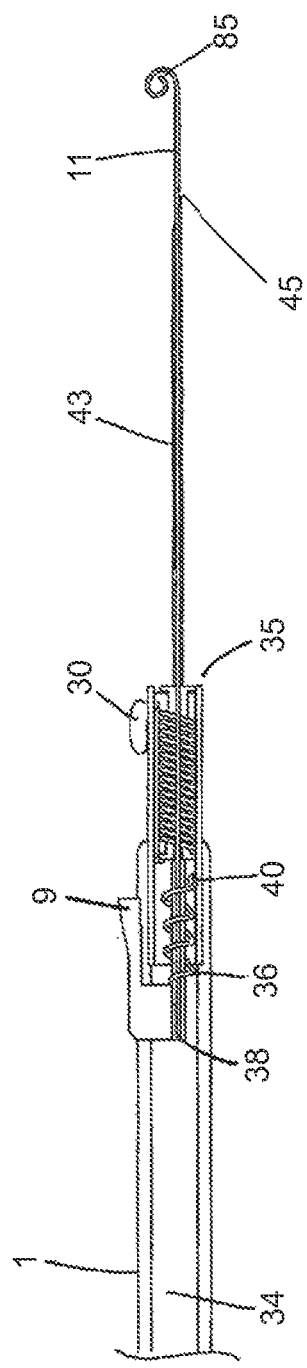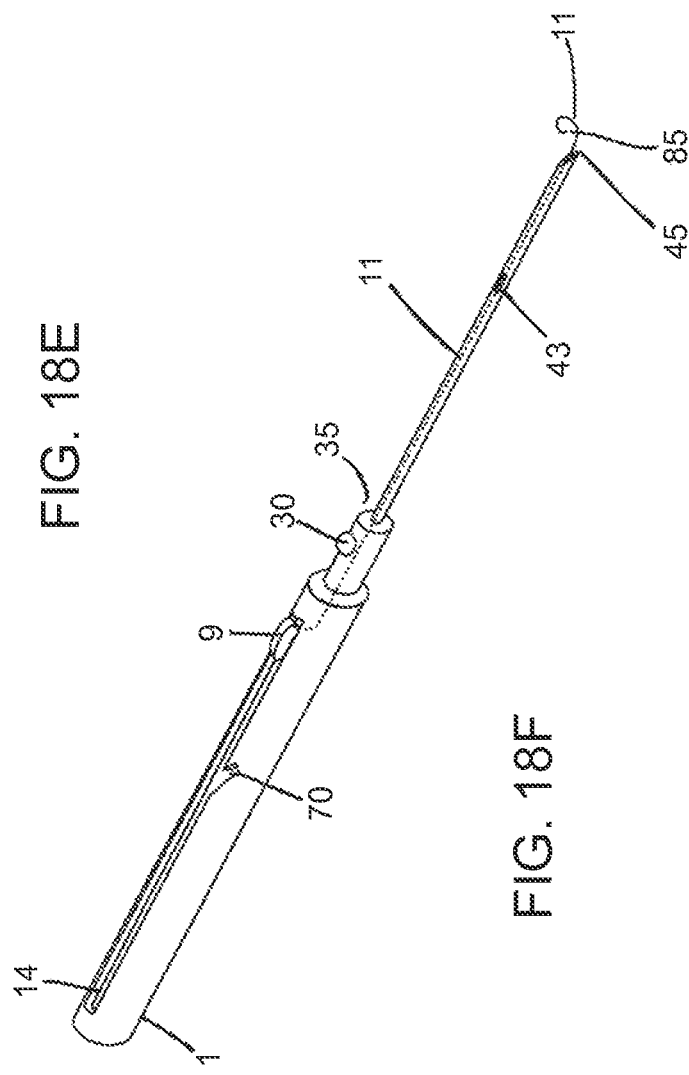
FIG. 18E
FIG. 18F

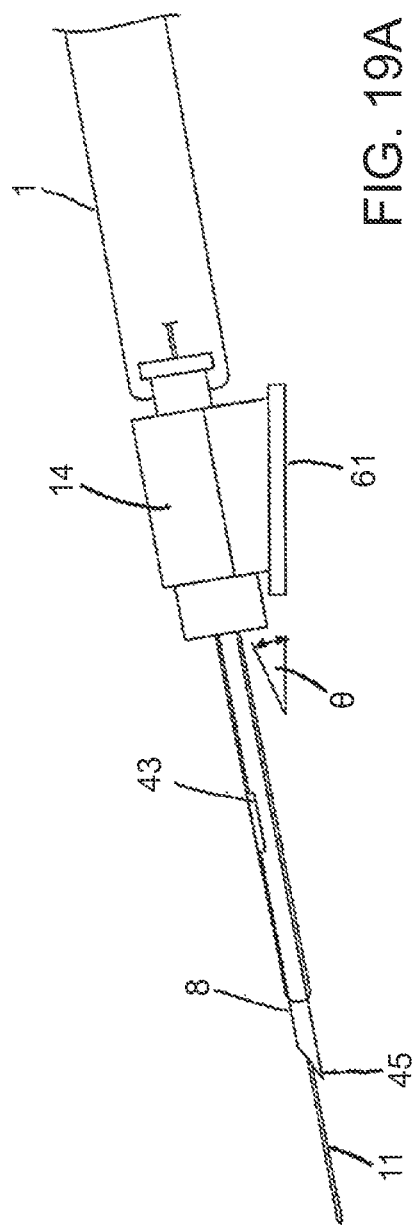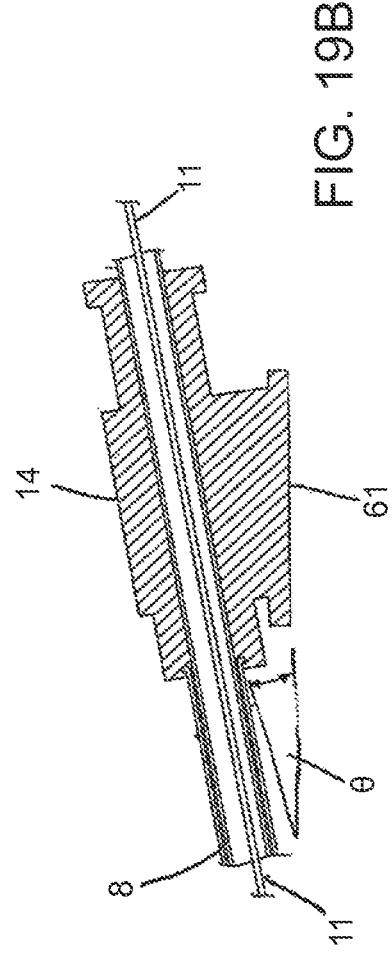

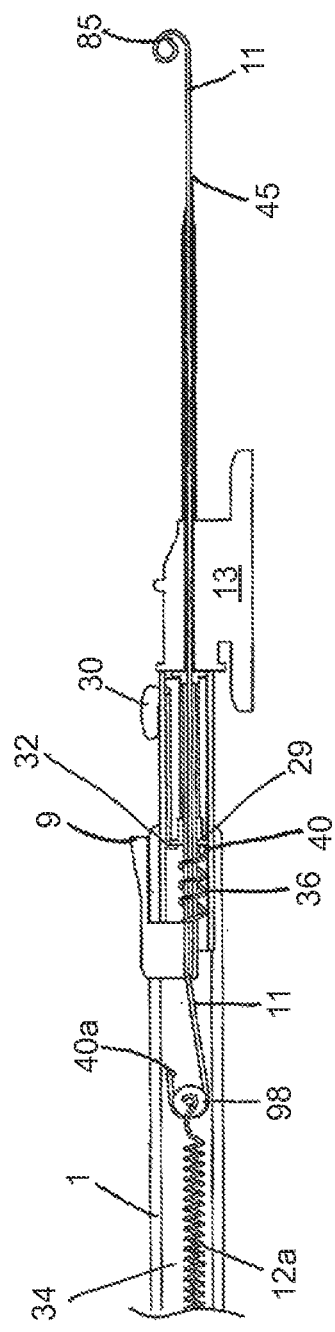
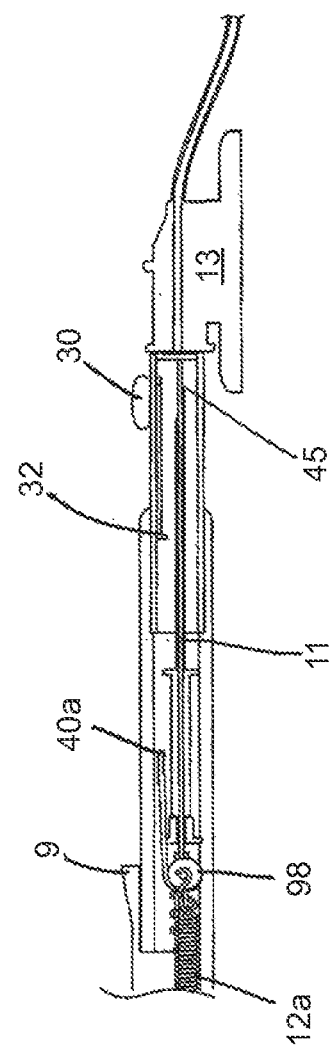
FIG. 26A
FIG. 26B

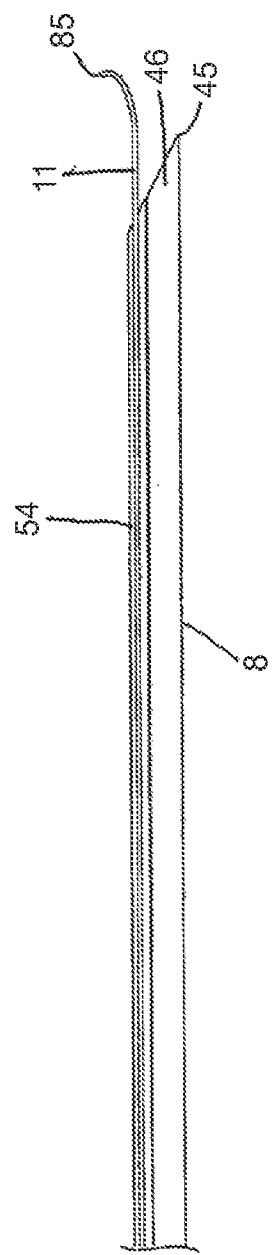
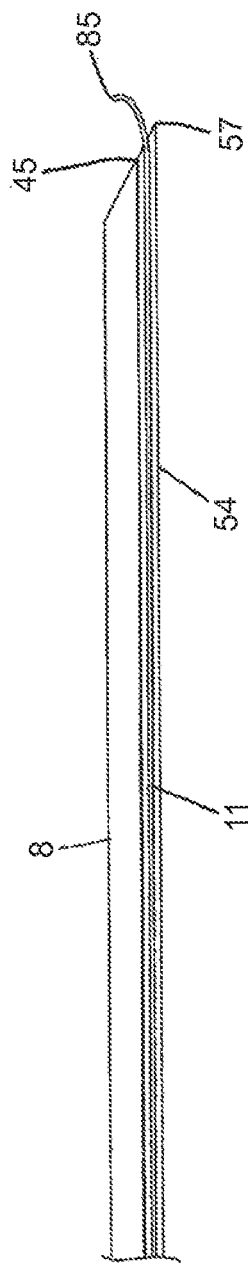
FIG. 27A
FIG. 27B

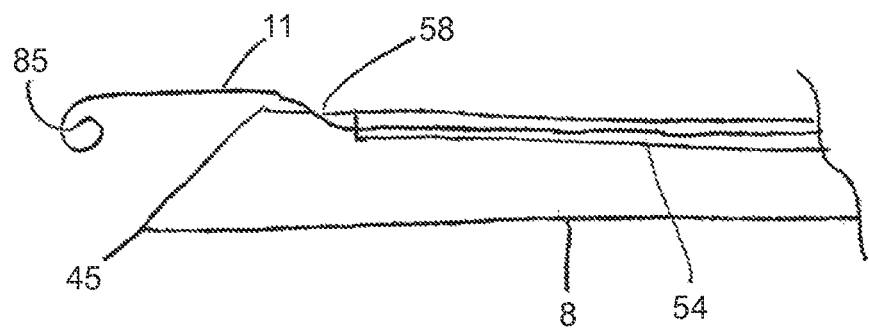
FIG. 27C
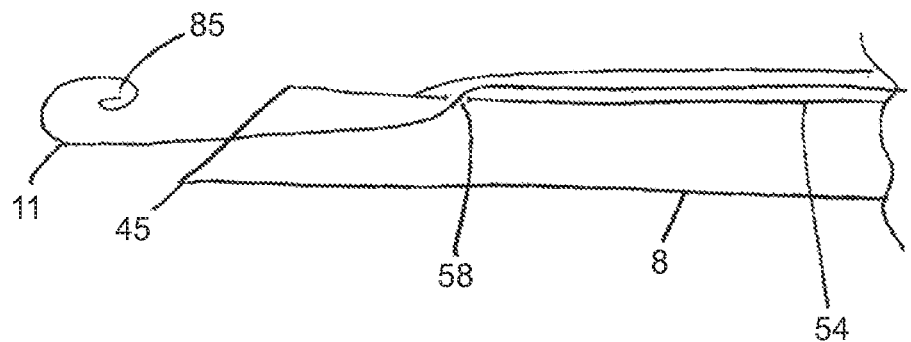
FIG. 27D
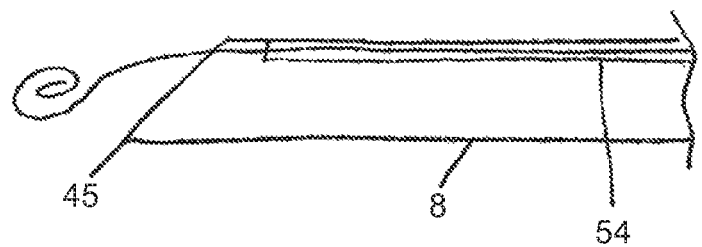
FIG. 27E
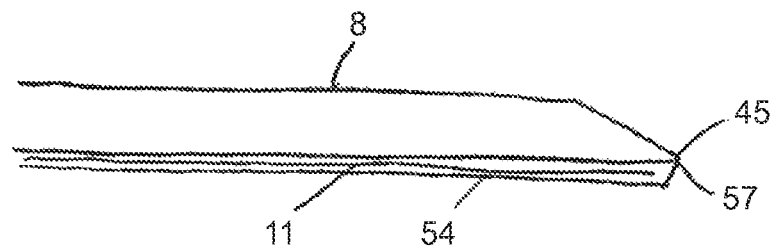
FIG. 27B1

INTRAVENOUS CATHETER INSERTION DEVICE AND METHOD OF USE

CROSS-REFERENCE TO RELATED APPLICATIONS

This application is a continuation of U.S. patent application Ser. No. 14/250,093, filed Apr. 10, 2014, now U.S. Pat. No. 10,806,906, which is a continuation of U.S. patent application Ser. No. 12/307,519, filed Dec. 3, 2009, now U.S. Pat. No. 8,728,035, which is a U.S. national stage application under 35 U.S.C. § 371 of International Application No. PCT/US2007/068393, filed May 7, 2007, which is a continuation-in-part of U.S. patent application Ser. No. 11/577,491, filed Apr. 18, 2007, now U.S. Pat. No. 9,162,037, which is a U.S. national stage application under 35 U.S.C. § 371 of International Application No. PCT/US2006/026671, filed Jul. 6, 2006, which claims the benefit of U.S. Provisional Patent Application No. 60/697,333, filed Jul. 6, 2005. Each of these patent applications and all patents and patent applications referred to in this application are each incorporated herein by reference in their entireties.

BACKGROUND OF THE INVENTION

1. Field of the Invention

The present invention relates to devices and methods for insertion and placement of an intravenous catheter into a vein or artery of a patient. The devices and methods of the invention facilitate safe placement of the catheter into the patient's vein or artery, which is of particular importance in the case of small, tortuous, collapsed, fragile, and/or difficult to locate vessels. The devices and methods also provide protection against accidental punctures and/or contamination by the needle after placement of the intravenous catheter.

2. Background Art

The following patents and publications describe prior intravenous catheter insertion devices and/or safety devices for syringes and needles: EP Patent No. 0 515 710 B1 to Haining, titled, "Intravenous catheter and insertion device"; U.S. Pat. No. 5,019,049 to Haining, titled, "Intravenous catheter and insertion device"; U.S. Pat. No. 5,176,650 to Haining, titled, "Intravenous catheter and insertion device"; EP Patent No. 0 567 321 B1 to Chang, titled, "Intravenous catheter with needle guard"; EP Patent No. 0 652 020 B1 to Mahurkar, titled, "Retractable hypodermic needle assembly"; EP Patent No. 0 910 988 B1 to Mahurkar, titled, "Blood sample collection assembly"; U.S. Pat. No. 5,891,105 to Mahurkar, titled, "Hypodermic needle assembly"; U.S. Pat. No. 3,572,334 to DeWitt, titled, "Intravenous catheter placement unit"; EP Publication No. 0 750 916 to van Heugten, titled, "Protective needle cover containment"; EP Patent No. 0 942 761 B1 to Botich, titled, "Medical device with retractable needle"; EP Patent No. 1 075 850 B1 to Botich, titled, "Apparatus for intravenous catheter insertion"; U.S. Pat. No. 5,800,395 to Botich et al, titled, "Medical device with retractable needle"; U.S. Pat. No. 6,436,070 to Botich et al, titled, "Catheter insertion device with retractable needle"; U.S. Patent Publication No. 2003/060760 to Botich et al, titled, "Catheter insertion device with retractable needle"; WO 2000/012160 to Botich et al, titled, "Fluid infusion device with retractable needle"; WO 1996/032981 to Botich et al, titled, "Safety stylet for intravenous catheter insertion"; WO 1998/024494 to Botich et al, titled, "Medical device with retractable needle"; EP Patent No. 1 457 229 B1 to Shue, titled, "Intravenous catheter inserting device"; U.S. Patent Publication No. 2004/106903 to Shue, titled, "Intravenous catheter inserting device"; U.S. Pat. No. 3,592,192 to Harautuneian, titled, "Intravenous catheter apparatus with catheter telescoped on outside of puncturing cannula"; U.S. Pat. No. 3,610,240 to Harautuneian, titled, "Intravenous catheter apparatus with catheter telescoped inside puncturing cannula"; U.S. Pat. No. 4,037,600 to Poncy et al, titled, "Catheter placement system"; U.S. Pat. No. 4,292,970 to Hession, titled, "Apparatus for intravenous catheter starter"; U.S. Patent No. 4,834,718 to McDonald, titled, "Safety needle apparatus"; U.S. Pat. No. 4,944,725 to McDonald, titled, "Safety needle apparatus"; U.S. Pat. No. 4,909,793 to Vining et al, titled, "Intravenous catheter apparatus with retractable stylet"; U.S. Pat. No. 4,944,728 to Carrell et al, titled, "Intravenous catheter placement device"; U.S. Pat. No. 4,966,589 to Kaufman, titled, "Intravenous catheter placement device"; U.S. Pat. No. 5,007,901 to Shields, titled, "Intravenous catheter insertion device"; U.S. Pat. No. 5,562,629 to Haughton et al, titled, "Catheter placement system utilizing a handle, a sharp, and a releasable retainer mechanism providing retraction of the sharp upon disengagement of the catheter from the handle"; U.S. Pat. No. 5,562,634 to Flumene et al, titled, "Intravenous catheter with automatically retracting needle-guide"; U.S. Pat. No. 5,573,510 to Isaacson titled, "Safety intravenous catheter assembly with automatically retractable needle"; U.S. Pat. No. 6,056,726 to Isaacson, titled, "Self-contained safety intravenous catheter insertion device"; WO 1995/023003 to Isaacson, titled, "Self-contained safety intravenous catheter insertion device"; U.S. Pat. No. 5,891,098 to Huang, titled, "Safety intravenous catheter"; U.S. Pat. No. 5,941,854 to Bhitiyakul, titled, "Intravenous catheter"; U.S. Pat. No. 5,997,507 to Dysarz titled, "Biased spring hard needle retractable IV catheter"; U.S. Pat. No. 6,193,690 to Dysarz titled, "Inclined plane latching device for an IV catheter"; U.S. Pat. No. 6,221,047 to Greene et al, titled, "Safety intravenous catheter assembly and method for use with a needle"; U.S. Pat. No. 6,689,102 to Greene et al, titled, "Safety intravenous catheter assembly"; U.S. Pat. No. 6,695,814 to Greene et al, titled, "Safety intravenous catheter assembly and method for use with a needle"; U.S. Patent Publication No. 2001/014786 to Greene et al, titled, "Safety intravenous catheter assembly and method for use with a needle"; U.S. Patent Publication No. 2002/165497 to Greene et al, titled, "Safety intravenous catheter assembly"; WO 2000/006226 to Greene et al, titled, "Safety intravenous catheter assembly and method for use with a needle"; U.S. Pat. No. 6,322,537 to Chang, titled, "Safety intravenous catheter"; U.S. Pat. No. 6,620,136 to Pressly, Sr. et al, titled, "Retractable IV catheter placement device"; WO 2000/047256 to Pressly, Sr. et al, titled, "Retractable IV catheter placement device"; U.S. Pat. No. 6,730,062 to Hoffman et al, titled, "Safety catheter with non-removable retractable needle"; U.S. Patent Publication No. 2003/073956 to Hoffman et al, titled, "Safety catheter with non-removable retractable needle"; U.S. Patent Publication No. 2004/267204 to Brustowicz, titled, "On-demand needle retaining and locking mechanism for use in intravenous catheter assemblies"; WO 2003/043686 to Garcia Andreo, titled, "Flow regulating/autovalve intravenous catheter"; WO 1992/022344 to Sircom, titled, "Needle guard for intravenous catheter placement"; WO 1995/019193 to Ogle, titled, "Retractable venipuncture catheter needle and receptacle"; WO 1997/005912 to Rohrbough et al, titled, "Retractable venipuncture catheter needle and receptacle";

and WO 1997/021458 to Hwang, titled, "Intravenous catheter with flexible extender and protector against needle tip."

BRIEF SUMMARY OF THE INVENTION

In one embodiment of the present invention, there is provided a catheter insertion device having a housing having an interior space; an access needle that is slideable with respect to the interior space; a guide wire supported by and moveable relative to the access needle; a handle attached to the guide wire that is moveable relative to the housing to move the guide wire relative to the interior space; and a restraining element attached to the handle to limit the motion of the guide wire relative to the access needle.

In one aspect, the restraining element attached to the handle limits the proximal motion of the guide wire relative to the access needle. In another aspect, wherein the access needle comprises a bleed back indicator within the portion of the access needle extending beyond the housing. In another aspect, the access needle comprises a bleed back indicator visible in the distal end of a catheter when the access needle is positioned within a catheter. In a further aspect, the bleed back indicator comprises an opening in the sidewall of the distal end of the access needle.

In another embodiment, the catheter insertion device also includes a biasing element and a release button adapted and configured to automatically withdraw one or both of the guide wire and the access needle. In a further aspect, the biasing element and the release button are adapted and configured to simultaneously withdraw the guide wire and the access needle into the interior space. In another aspect, biasing element and the release button are adapted and configured to sequentially withdraw the guide wire and the access needle. In one embodiment, the catheter insertion device also includes a restraining element within the interior space that limits distal movement of the access needle or guide wire within the interior space. In one alternative, the restraining element limits distal movement of the access needle or guide wire after the access needle or guide wire have been withdrawn into the interior space after use to insert a catheter. In another alternative, the restraining element limits distal movement of the access needle or guide wire such that the access needle and guide wire remain completely withdrawn into the interior space.

In one embodiment of the catheter insertion device, the interior space is sized and configured to contain all of the guide wire and the access needle after insertion of a catheter. In another aspect, the guide wire has a first portion with a first diameter, a reducing section and a second portion with a second diameter that is less than the first diameter. In still a further aspect, the first diameter and the second diameter are less than the interior diameter of the access needle. In still another aspect, the distal end of the second portion comprises one or more of a full radius distal tip, a spherical ball of the same material as the guide wire, a spherical ball of a different material than the guide wire or a distal end having a diameter about the same as the first diameter. In one alternative, the guide wire comprises a braided structure. In yet another alternative, the catheter insertion device includes a guide channel within the housing to confine the movement of the handle and a holding channel adjacent to the guide channel wherein the holding channel is adapted to prevent movement of the handle once the handle is in the holding channel. In one aspect, the restraining element prevents proximal guide wire movement and the holding channel prevents distal guide wire movement. In another aspect there is a pulley secured within the interior space configured to facilitate movement of the guide wire into the interior space.

In another embodiment, there is provided a catheter insertion device having a housing having an interior space; an access needle having a distal end, a proximal end and an interior wall defining a lumen that extends from the distal end to the proximal end; an access needle that is slideable relative to the interior space; an opening in the sidewall of the access needle in communication with the access needle lumen; and a guide wire supported by the access needle. In another aspect, the catheter insertion device also includes a restraining element attached to the guide wire and configured to prevent the guide wire from moving into the opening. In one aspect, there is also a restraining element attached to the guide wire wherein when the guide wire is positioned within the access needle distal to the opening the restraining element limits proximal movement of the guide wire towards the opening. In another alternative, the access needle lumen has a cross section shape that maintains the orientation of the guide wire relative to the access needle lumen. In one aspect, the access needle lumen has a non-circular cross section shape. In another aspect, the access needle lumen has an elliptical cross section shape. In another aspect, there is also a feature formed within the access needle sidewall to maintain the orientation of the guide wire relative to the access needle lumen. In one alternative, the feature is a groove. In one aspect, the opening in the sidewall of the access needle is positioned proximal to the distal end of the access needle.

In another alternative, the opening in the sidewall of the access needle is positioned distal to the distal end of the housing. In another alternative, the access needle constrains the guide wire into a non-coiled configuration within the access needle. In another alternative, the guide wire is coiled within the access needle. In one aspect, the guide wire is coiled to form at least one half of a rotation within the access needle lumen. In another aspect, the guide wire is coiled to form one or more rotations within the access needle lumen. In still another aspect, the guide wire is within the access needle. In another aspect, the guide wire is alongside the access needle. In one embodiment, there is also a guide wire channel supported by the access needle.

In another embodiment of the catheter insertion device of the invention, there is provided a housing having an interior space and a longitudinal axis; a feature on the distal end of the housing that when coupled to a catheter offsets the housing longitudinal axis from the longitudinal axis of the catheter; and an access needle passing through the feature and attached to a needle carrier wherein the needle carrier is slideable with respect to the interior space and the access needle is slideable relative to the feature. In one alternative, when the feature on the distal end of the housing is coupled to the catheter the housing longitudinal axis is offset from the longitudinal axis of the catheter to form an angle of less than 180 degrees. In one alternative, when the feature on the distal end of the housing is coupled to the catheter the housing longitudinal axis is offset from the longitudinal axis of the catheter to form an angle of less than 60 degrees. In another alternative, when the feature on the distal end of the housing is coupled to the catheter the housing longitudinal axis is offset from the longitudinal axis of the catheter to form an angle of less than 45 degrees. In another alternative, there is also a guide wire supported by and moveable relative to the access needle. In another alternative, there is also a handle attached to the guide wire that is moveable relative to the housing to move the guide wire relative to the interior space. In another alternative, there is also a restraining element attached to the handle to limit the motion of the guide wire relative to the access needle. In one aspect, when the access needle and the guide wire are withdrawn into the interior space the guide wire and the access needle are withdrawn substantially parallel to the longitudinal axis of the housing. In another aspect, the guide wire is disposed within the access needle. In another aspect, the guide wire is alongside the access needle.

In another embodiment of the catheter insertion device of the invention, there is a housing having an interior space; an access needle that is slideable with respect to the interior space; a guide wire supported by and moveable relative to the access needle; and a handle attached to the guide wire wherein the movement of the handle is limited so that at least a portion of the guide wire always remains in the interior space. In another alternative, there is also a biasing element adapted and configured to move the needle carrier proximally within the interior space when released. In one aspect, the biasing element is adapted and configured to move the guide wire proximally within the interior space when released. In one aspect, the biasing element is adapted and configured that, when released, moves the needle so that the needle is completely within the interior space. In another aspect, the biasing element is adapted and configured to move the guide wire so that the entire length of the guide wire is completely within the interior space. In another alternative, there is also a restraining element within the interior space that limits distal movement of the access needle or guide wire within the interior space once the access needle or guide wire has moved proximal to the restraining device. In one aspect, one end of the guide wire is secured to the housing. In one aspect, one end of the guide wire is constrained within the interior space when the guide wire is extended beyond the distal end of the access needle. In one aspect, the guide wire is disposed within the access needle. In another aspect, the guide wire is disposed alongside the access needle.

In another embodiment of the catheter insertion device of the invention, there is provided a housing having an interior space; an access needle that is slideable with respect to the interior space; a guide wire channel attached to the access needle; a guide wire supported by and moveable relative to the guide wire channel; and a handle attached to the guide wire wherein the movement of the handle moves the guide wire relative to the support channel. In one aspect, the movement of the handle is limited so that at least a portion of the guide wire always remains in the interior space. In another aspect, there is also provided a biasing element and a release button adapted and configured to automatically withdraw one or both of the guide wire and the access needle. In another aspect, there is also provided a restraining element within the interior space that limits distal movement of the access needle or guide wire within the interior space. In one aspect, the distal end of the guide wire channel is adjacent the distal end of the access needle. In another aspect, the guide wire channel is on the top of the access needle. In another aspect, the guide wire channel is on the bottom of the access needle. In another aspect, the guide wire passes out the distal end of the guide wire channel without passing through the access needle lumen. In still another aspect, the guide wire passes out the distal end of the guide wire channel and through a portion of the access needle lumen. In another aspect, the guide wire channel is attached to the access needle within the access needle lumen.

In other embodiments of the invention, there are provided several methods of introducing a catheter into a vessel including inserting a guide wire substantially contained within a housing into a vessel; advancing a catheter over the guide wire and into the vessel; and withdrawing the guide wire out of the vessel and completely into the housing. In one alternative, the step of advancing the guide wire along a needle inserted into the vessel is performed before performing the inserting step. In one alternative, the step of advancing the guide wire along a needle inserted into the vessel is performed before performing the inserting step. In another alternative, the step of coiling the guide wire within the vessel is performed after the inserting step.

In one aspect, the withdrawing step is accomplished manually. In another aspect, the withdrawing step is accomplished automatically. In another alternative, the withdrawing step is accomplished by releasing a biasing member to withdraw the guide wire completely into the housing. In another alternative, releasing a biasing member also withdraws a needle supporting the guide wire completely into the housing. In another alternative, the withdrawing step is initiated by pushing a button. In another alternative, inserting a needle attached to the housing into the vessel is performed before the step of inserting a guide wire step. In another alternative, the method also includes using a flashback indicator near the distal tip of the needle to determine that the needle has entered the vessel after the inserting a needle step. In another alternative, the method also includes moving a handle attached to the guide wire proximally before the inserting step.

Although the invention is described in relation to insertion of an intravenous catheter, the apparatus and methods described herein could readily be adapted for insertion of any catheter or similar device into a vein, artery or other internal body structure.

BRIEF DESCRIPTION OF THE DRAWINGS

In the drawings:

FIGS. 4A and 4B are detail drawings of a safety guide wire for use with the intravenous catheter insertion device.

FIGS. 5A, 5B and 5C are detail drawings of another safety guide wire for use with the intravenous catheter insertion device.

FIGS. 7-9 illustrate a method of intravenous catheter insertion according to the present invention.

FIGS. 10A and 10B illustrate cross section views of one embodiment of a catheter insertion device.

FIG. 10C is a section view of catheter hub with an angled base and FIG. 10D illustrates a section view of a conventional catheter.

FIGS. 11A-14B illustrate a catheter insertion device in use to insert a catheter into a vessel and automatically withdrawn the access needle and guide wire into a housing;

FIG. 15 is a section view of an alternative catheter insertion device with a restraint to prevent unintended distal movement within the housing interior;

FIGS. 16A and 16B illustrate perspective and end views, respectively, of an access needle adapted to maintain the orientation of a guide wire;

FIGS. 17A and 17B illustrate perspective and end views, respectively, of an access needle adapted to maintain the orientation of a guide wire;

FIGS. 18A-18H illustrate section and perspective views of the use of a catheter insertion device having a guide channel and restraining features;

FIGS. 19A and 19B are side and section views respectively of the catheter of FIG. 10C;

FIG. 26A illustrates a section view of a catheter insertion device with the guide wire extended;

FIG. 26B illustrates section view of catheter insertion device of FIG. 26B where a pulley has been used to withdraw the guide wire completely into the housing;

FIGS. 27A-27E illustrate section views of the access needle of a catheter insertion device with an attached guide wire channel. FIG. 27B1 is similar to FIG. 27B except that the guide wire is drawn back into the guidewire channel.

DETAILED DESCRIPTION OF THE INVENTION

Figure 1:
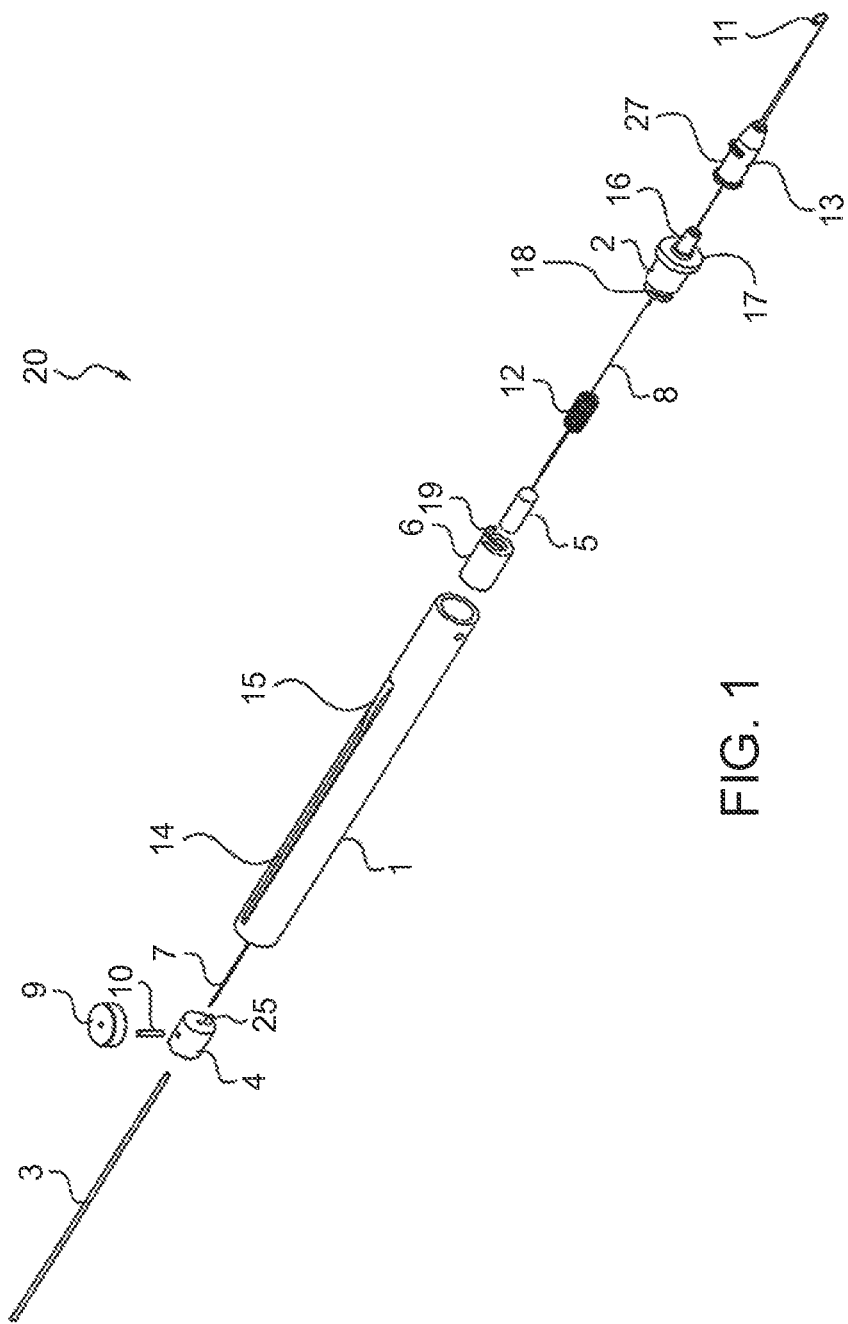
FIG. 1 shows an exploded view of an intravenous catheter insertion device according to the present invention.
Figure 2:
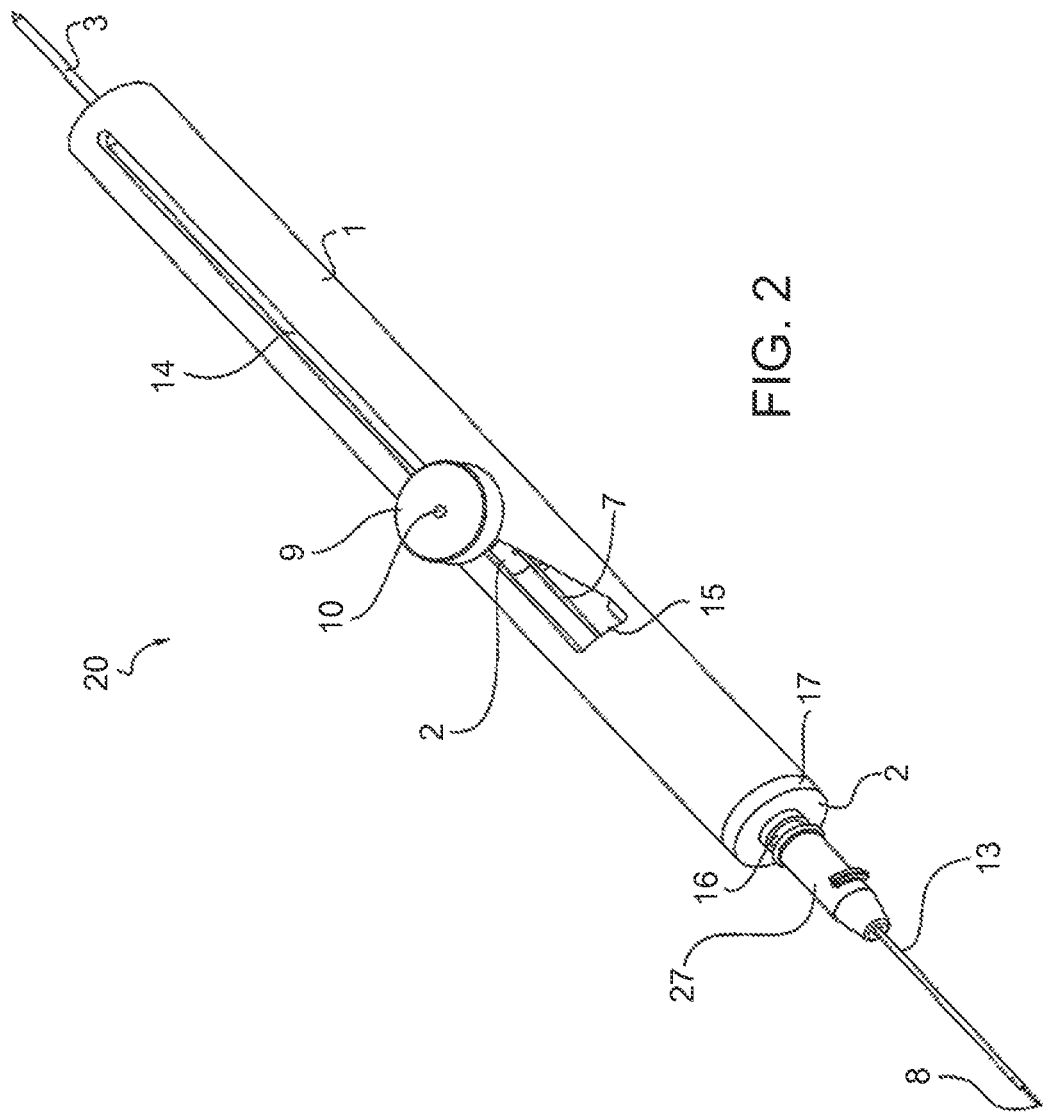
FIG. 2 shows an assembly drawing of the intravenous catheter insertion device in an undeployed state, ready for use.
Figure 3:
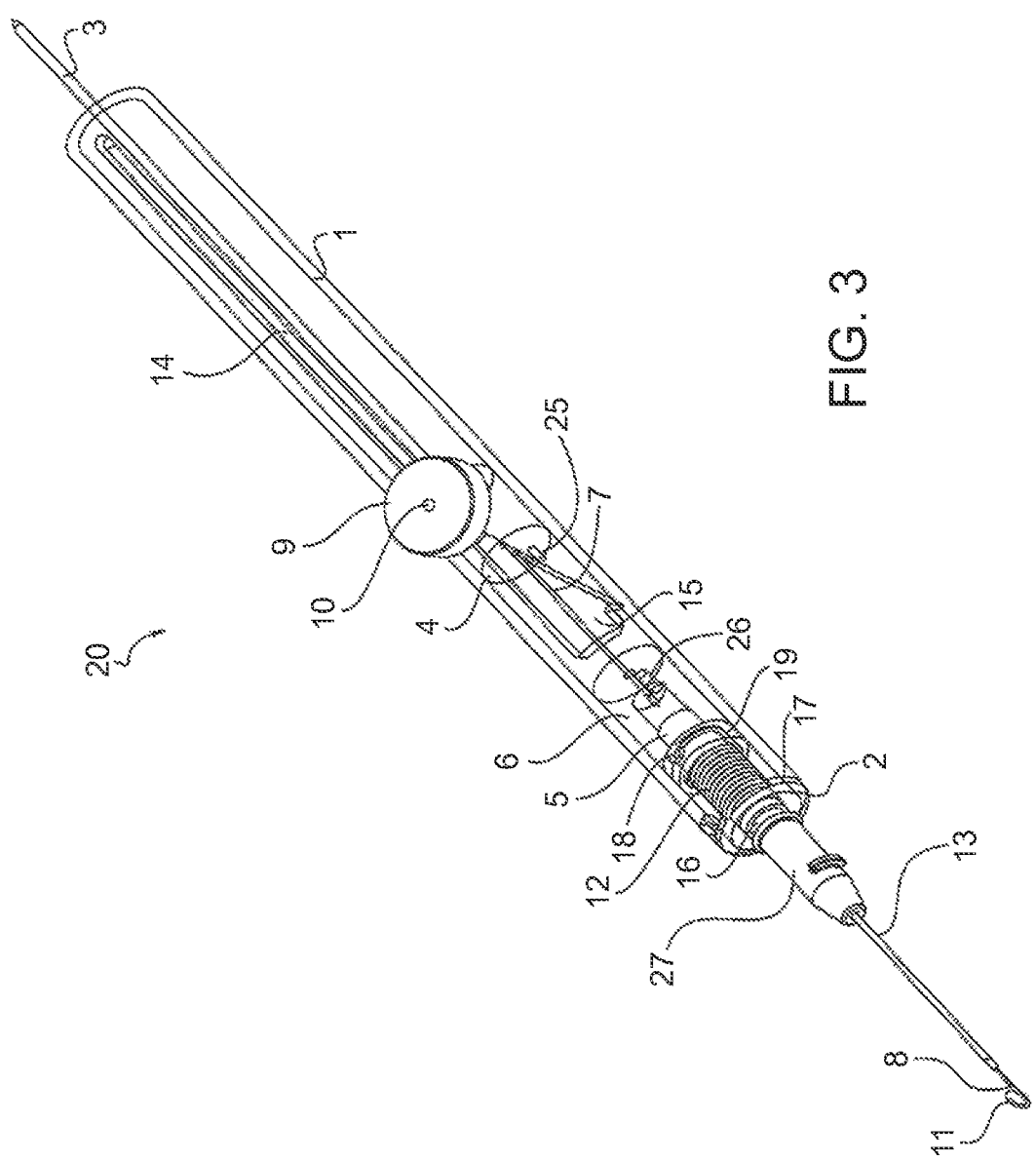
FIG. 3 shows a phantom view of the intravenous catheter insertion device with the safety guide wire advanced.

FIG. 1 shows an exploded view of one embodiment of an intravenous catheter insertion device 20 according to the present invention. FIG. 2 shows an assembly drawing of the intravenous catheter insertion device 20 in an undeployed state, ready for use. FIG. 3 shows a phantom view of the intravenous catheter insertion device 20 with the safety guide wire advanced.

The intravenous catheter insertion device 20 includes an outer housing 1. In the example shown, the outer housing 1 is in the form of an elongated hollow cylinder. Other shapes, including an ergonomic handle shape, are possible. The outer housing 1 may be formed from any material suited for use in medical applications. In one embodiment, the outer housing 1 is preferably molded from a rigid, transparent medical grade plastic. Alternatively, the outer housing 1 may be machined from an extruded plastic tube.

There is an elongated slot 14 in the outer housing 1 approximately parallel with the axis of the outer housing 1. The slot 14 is sized to accommodate the dowel pin 10 or provide a connection point to the slider 4 to move the slider along the interior of the outer housing 1. The distal end of the slot 14 widens into a triangular cutout 15, as seen in FIGS. 2 and 3. Other shapes of the cut out 15 are possible.

A front plug 2 is sized to fit onto the distal end of the outer housing 1. The front plug 2 is preferably molded, or alternatively machined, from a rigid, transparent medical grade plastic. The front plug 2 is glued, pinned, welded or otherwise fastened to the distal end of the outer housing 1. The distal end of the front plug 2 includes a luer slip fitting 16 or the like. There is a shoulder or flange 17 to mate with the distal end of the outer housing 1. The proximal end of the front plug 2 has an interlocking member 18 that interlocks with a mating interlocking member 19 on the needle carrier 6. In the example shown, the interlocking member 18 is a tab that interlocks with a corresponding spiral pawl or quarter-turn thread interlocking member 19 on the needle carrier 6. Other geometries for the interlocking members 18, 19 are possible.

In the exemplary embodiment of FIGS. 1-3, the geometry of the slot 14 and the triangular cutout 15 are chosen to operate cooperatively with the rotating interlocking members 18, 19. The slot 14 allows the actuator handle 9 to move in a longitudinal direction with respect to the outer housing 1 to advance the safety guide wire 11 distally, while at the same time restricting lateral motion to avoid premature withdrawal of the access needle 8 and the safety guide wire 11. The widening of the slot 14 at the distal end into a triangular cutout 15 allows the actuator handle 9 to be selectively rotated laterally to disengage the rotating interlocking members 18, 19 and release the biasing member 12 to withdrawal of the access needle 8 and the safety guide wire 11 after the safety guide wire 11 has been fully advanced. If a different geometry or different release mechanism is used in place of the rotating interlocking members 18, 19, the geometry of the slot 14 and the triangular cutout 15 may have to be modified to accommodate the release mechanism.

The needle carrier 6 is shaped and sized to fit inside the outer housing 1. In the embodiment shown in FIGS. 1-3, the needle carrier 6 has a cylindrical shape that is sized to have a sliding fit within the cylindrical outer housing 1. Other shapes are possible and generally the needle carrier 6 will be shaped to be compatible with the interior geometry of the outer housing 1. The needle carrier 6 is preferably molded, or alternatively machined, from any material suited for use in a medical environment. In one embodiment, the needle carrier 6 is formed from a rigid, transparent medical grade plastic. A tubular access needle 8 with a sharpened beveled distal end is attached to a needle carrier nose 5, which is in turn attached to the needle carrier 6. The access needle 8 is preferably made from stainless steel hypodermic tubing. A small cavity or blood flashback chamber that communicates with the lumen of the access needle 8 is positioned within the needle carrier 6, between the needle carrier nose 5 and the needle carrier 6. As mentioned above, the distal end of the needle carrier 6 has an interlocking member 19 that is configured to interlock with a mating interlocking member 18 on the proximal end of the front plug 2. In one exemplary embodiment, the interlocking members 18, 19 are adapted to lock and unlock by rotation of the needle carrier 6 with respect to the front plug 2. The interlocking members 18, 19 may also lock and unlock using a bayonet-type fitting. In the example shown, the interlocking member is a spiral pawl interlocking member 19 that interlocks with a corresponding tab interlocking member 18 on the front plug 2. In one embodiment, the interlocking members lock and/or unlock using less than one revolution of the needle carrier 6. In another embodiment, the interlocking members lock and/or unlock using less than one half a revolution of the needle carrier 6. In still another alternative embodiment, the interlocking members lock and/or unlock using less than one quarter revolution of the needle carrier 6. Other geometries for the interlocking members are possible.

A biasing member 12 is configured to fit between the needle carrier 6 and the front plug 2 to urge them apart. The force of the biasing member 12 is resisted by the interlocking members 18, 19 when the needle carrier 6 and the front plug 2 are locked together. In one embodiment, the biasing member 12 is a spring. Note that in FIG. 1 the biasing member or compression spring 12 is shown in a compressed condition as it would be in the assembled intravenous catheter insertion device 20 in an undeployed condition.

In an alternate embodiment, the interlocking members 18, 19 may be replaced by two members that are bonded together with a breakable bond or a single member with a breakable link. The member or members would be configured to constrain the biasing member 12 until it is desired to withdraw the access needle 8 and safety guide wire 11, at which time; the actuator would break the bond or link to release the biasing member 12. This configuration would make the device 20 more resistant to remanufacturing or reuse.

A tubular intravenous catheter 13, such as an ANGIO-CATH, fits coaxially around the access needle 8. Preferably, the intravenous catheter 13 has a close fit with the access needle 8 and a tapered distal end to minimize any step between the access needle 8 and the intravenous catheter 13 as they are inserted through the wall of a vein. There is a luer fitting 27 or the like on the proximal end of the intravenous catheter 13 that fits onto the luer slip fitting 16 on the distal end of the front plug 2 with a slight interference fit to hold the intravenous catheter 13 in place. Alternative configurations of the device may use a luer lock or other locking mechanism to attach the intravenous catheter 13 to the front plug 2.

A slider 4 is generally cylindrical in shape and sized for a sliding fit inside the cylindrical outer housing 1. Other shapes for the slider 4 are possible depending on the interior geometry of the outer housing 1. The slider 4 is preferably molded, or alternatively machined, from any suitable medical grade material. For example, the slider may be formed from a rigid medical grade plastic. A handle 9 or actuating member attaches to the slider 4 with a dowel pin 10 or other attachment member that extends through the slot 14 in the outer housing 1. The slider 4 fits into the outer housing 1 proximal to the needle carrier 6. A pin 25 extends from the distal surface of the slider 4 and is configured to reversibly engage with a hole, step, boss or similar mating feature 26 on the proximal end of the needle carrier 6. When pin 25 is coupled to the mating feature 26 during the appropriate step of the intravenous catheter insertion and placement procedure, rotation of the slider 4 is transferred to the needle carrier 6 to facilitate engagement and or disengagement of the interlocking members 18, 19. Pin 25 and feature 26 are merely illustrative. Pin 25 may be replaced with a female feature while a mating male feature may be placed on the proximal face of the needle carrier 6. Additionally, the mating features 25, 26 are aligned relative to the elongated slot and the sliding movement of the slider 4 so that distal movement of the slider 4 will engage the mating features 25, 26. Optionally, the device 20 may be configured so that the connection between the slider 4 and needle carrier 6 happens irreversibly when the device 20 is actuated.

As best seen in FIG. 3, a safety guide wire 11 is attached, directly or indirectly, to the slider 4 so that it can be advanced and retracted with the handle 9 attached to the slider 4. In a preferred embodiment, the safety guide wire 11 is constructed of super elastic Nickel-Titanium alloy (Nitinol) wire. Because this type of wire is extremely flexible, it is advantageous to have the safety guide wire 11 enclosed along most of its length to avoid bowing or buckling while advancing the safety guide wire 11. For this reason, the example shown includes a support tubing 7 that is attached to the proximal end of the needle carrier 6. The safety guide wire 11 extends through the internal lumen of a sheath tubing 3 and the proximal end of the safety guide wire 11 is attached at the proximal end of the sheath tubing 3. The distal end of the sheath tubing 3 is in turn attached to the slider 4, indirectly attaching the safety guide wire 11 to the slider 4. The support tubing 7 has a sliding fit inside the sheath tubing 3 so that the two parts telescope together as the slider 4 is advanced in the distal direction. The telescoping action of the support tubing 7 and the sheath tubing 3 provides a variable-length support for the proximal portion of the safety guide wire 11 to prevent bowing or buckling of the safety guide wire 11 as it is advanced. The support tubing 7 and the sheath tubing 3 are preferably made from stainless steel hypodermic tubing, however any suitable medical grade plastic material may also be used. In other embodiments, such as those using a larger diameter or stiffer guide wire, the telescoping support tubes may not be necessary and the proximal end of the safety guide wire 11 may be attached directly to the slider 4.

FIGS. 4A and 4B are detail drawings of a safety guide wire 11 for use with the intravenous catheter insertion device 20. The safety guide wire 11 is preferably constructed of super elastic Nickel-Titanium alloy wire approximately 0.004-0.012 inches in diameter and most preferably approximately 0.008 inches in diameter. As shown in FIG. 4B, the distal end of the safety guide wire 11 is preformed into a tightly wound spiral with an outer diameter smaller than the internal diameter of the target vessel into which it will be inserted. The spiral tip acts as a safety bumper on the guide wire to avoid puncturing or damaging the inside of target vessels. The coiled guide wire tip is particularly useful in protecting fragile or delicate veins. Due to the extreme flexibility of the Nickel-Titanium alloy wire, the spiral distal curve can straighten out when the safety guide wire 11 is withdrawn into the access needle 8 and completely recover into the spiral configuration without plastic deformation when the safety guide wire 11 is advanced out of the access needle 8. In the example shown, the distal end of the safety guide wire 11 has a first, small diameter coil of approximately 0.167 inches in diameter for approximately 0.75 revolutions and a second, larger diameter coil of approximately 0.175 inches in diameter for approximately 1 revolution. The first and second coils are preferably approximately coplanar with one another and preferably approximately coplanar with the straight proximal portion of the guide wire 11 also. Other configurations of the safety guide wire 11 may include: multi-planar, single coil, full radius on the end, and/or a balled end with diameter less than the diameter of the needle.

FIGS. 5A, 5B and 5C are detail drawings of another safety guide wire 11 for use with the intravenous catheter insertion device 20. In this embodiment, a distal portion of an approximately 0.008 inch diameter Nickel-Titanium alloy wire has been tapered by grinding, stretching, etc., to a diameter of approximately 0.004 inches to make it more flexible and to allow it to be formed into a smaller diameter spiral for use in smaller diameter veins. The spiral curve of the guide wire tip will preferably have an outer diameter smaller than the inner diameter of the target vessel. In the example shown, the spiral curve has a first, small diameter coil of approximately 0.034 inches in diameter for approximately 0.75 revolutions and a second, larger diameter coil of approximately 0.059 inches in diameter for approximately 1 revolution. The first and second coils are preferably approximately coplanar with one another and preferably approximately coplanar with the straight proximal portion of the guide wire 11 also.

Other sizes and geometries of safety guide wire 11 are also possible.

To assemble the intravenous catheter insertion device 20 shown in FIGS. 1-3, the access needle 8 is bonded flush with the proximal face of the needle carrier nose 5, which is in turn bonded into the needle carrier 6. The support tubing 3 is placed into the distal hole in the needle carrier 6, and bonded flush with the proximal face of the blood flashback chamber. The formed safety guide wire 11 is advanced through the lumen of the access needle 8 and support tubing 7 until the coiled section of the safety guide wire 11 meets the access needle 8 bevel. The sheath tubing 3 is slid through the slider 4, and bonded when flush with the distal face. The assembly of the sheath tubing 3 and slider 4 are advanced over the safety guide wire 11. When the safety guide wire 11 is flush with the proximal end of the sheath tubing 3, the two are bonded. The spring 12 is compressed on the needle carrier nose 5, advanced into the front plug 2 and the interlocking members 18, 19 of the front plug 2 and needle carrier 6 are engaged. This assembly of components is placed into the outer housing 1 and advanced until the front plug 2 is flush with the outer housing 1, and then the front plug 2 is rotated for proper alignment. The front plug 2 is then bonded to the outer housing 1. The dowel pin 10 and handle 9 are pressed together with the slider 4. The handle 9 is slid proximally to withdraw the safety guide wire 11 into the access needle 8, thereby straightening out the spiral distal curve. An intravenous catheter 13 is then mounted coaxially around the access needle 8. Optionally, the intravenous catheter 13 insertion device may be provided with a needle cover or other protective packaging. The assembled intravenous catheter insertion device 20, including the intravenous catheter 13, is then packaged, labeled and sterilized.

The preceding assembly description is provided to illustrate one example of a process for manufacturing an embodiment of the intravenous catheter insertion device 20 and also so that the interrelationship of the various components will be understood. Modifications and variations of this description are expected depending upon specific selected assembly or manufacturing techniques. For example, components that are bonded may be redesigned to be formed from a single integrated piece and the like. The manufacturing process can be modified and adapted for assembling other embodiments of the intravenous catheter insertion device 20.

Figure 6:
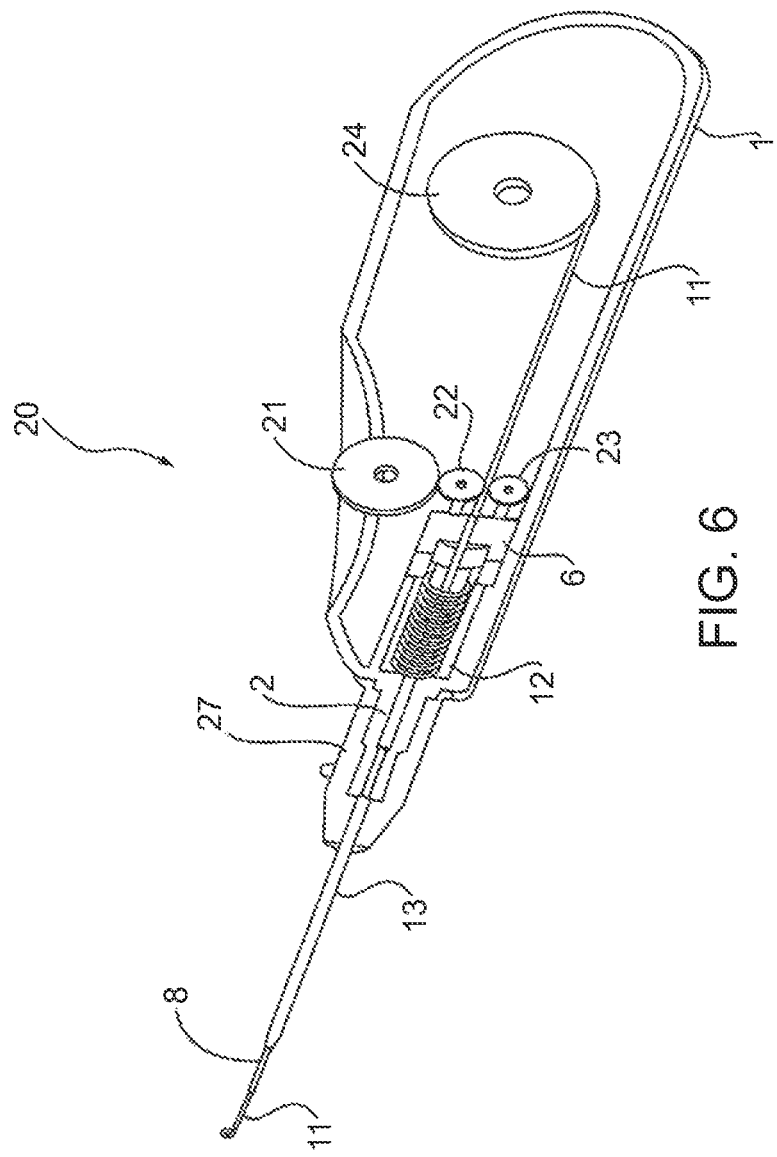
FIG. 6 shows another embodiment of an intravenous catheter insertion device according to the present invention.

FIG. 6 shows an interior view of another embodiment of an intravenous catheter insertion device 20 according to the present invention. This embodiment is similar in many respects to the intravenous catheter insertion device 20 of FIGS. 1-3. The intravenous catheter insertion device 20 includes an outer housing 1, front plug 2, which may optionally be molded integrally with the outer housing 1, a needle 8 attached to a needle carrier 6, a safety guide wire 11, spring 12 and intravenous catheter 13. However, the functions of the handle 9 and the slider 4 have been replaced by a thumbwheel 21 that engages a pair of friction wheels 22, 23, which are in contact with the safety guide wire 11. Likewise, the functions of the sheath tubing 3 and the support tubing 7 have been replaced by a guide wire spool 24. These features allow the intravenous catheter insertion device 20 to be constructed in a more compact configuration. In use, the safety guide wire 11 is advanced by turning the thumbwheel 21. A lateral movement of the thumbwheel 21 disengages the needle carrier 6 from the front plug 2, allowing the biasing member 12 to expand, thereby retracting the needle 8 and the safety guide wire 11 into the outer housing 1. Alternatively, a separate button, lever or other actuation member can be provided to actuate the withdrawal of the needle 8 and the safety guide wire 11. The guide wire spool 24 may optionally include a rotary spring or similar mechanism (not shown) to assist in the retraction of the safety guide wire 11 into the outer housing 1.

Figure 7:
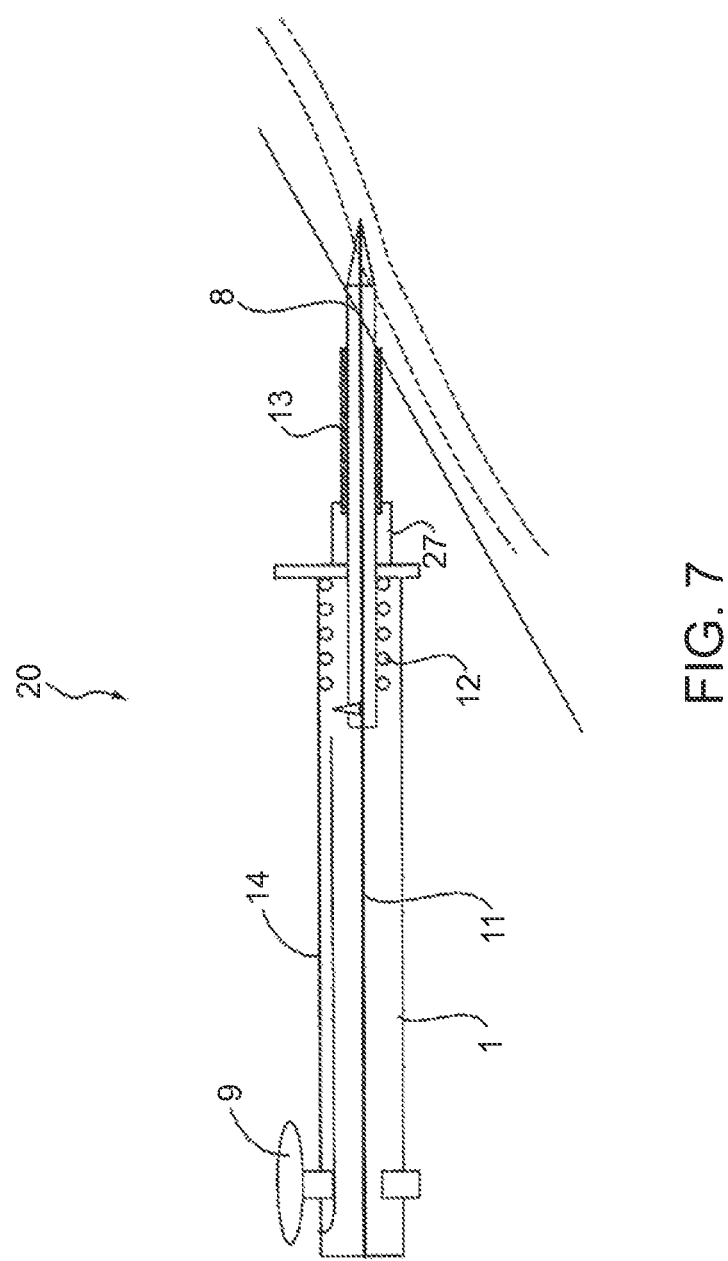

In one embodiment, the length of the guide wire 11 on the spool 24 is more than twice the length of the housing 1. In another aspect, the length of the guide wire on spool 24 is sufficient to provide guide wire access to a central vein. In one embodiment, the guide wire spool contains a guide wire having a length between 10 to 60 centimeters. The guide wire spool 24 may also be configured to include a clutch, cam or other releasable engagement element to disengage the spool 24 during advancement of the guide wire 11 in order to reduce the force needed to rotate thumbwheel 21 or wheels 22, 23. After advancement is completed, the releasable engagement element would then engage the retraction mechanism associated with the spool 24. Once guide wire withdrawal is desired, the withdrawal mechanism is actuated. The use of the guide wire spool 24 allows for the use of a guide wire insertion length that is much longer than the length of the housing containing the guide wire spool FIGS. 7-9 illustrate a method of inserting an intravenous catheter using an intravenous catheter insertion device 20, such as those described in FIGS. 1-3 or FIG. 6. The intravenous catheter insertion device 20 is a single-use, non-reusable device supplied to the physician or medical practitioner sterile in a ready-to-use, undeployed condition as shown in FIG. 2. In use, the physician uses the outer housing 1 as a handle to manipulate the intravenous catheter insertion device 20. With the device in the undeployed condition, the access needle 8 is used to puncture a vein, as shown in FIG. 7. When venous blood is observed in the blood flashback chamber, the distal tip of the access needle 8 is the lumen of the vein. The physician can then advance the handle 9 in the distal direction to extend the safety guide wire 11 out of the access needle 8 into the lumen of the vein. The distal portion of the safety guide wire 11 assumes its spiral configuration to act as a safety bumper to prevent accidental puncture of the far wall of the vein or other damage to the vein. With the safety guide wire 11 thus deployed, the physician can safely continue advancing the intravenous catheter insertion device 20 until the distal tip of the intravenous catheter 13 is in the lumen of the vein. Once the intravenous catheter 13 is inserted far enough into the vein, the physician rotates the handle 9 that rotates the slider 4, which in turn rotates the needle carrier 6 and disengages the interlocking member 18 of the needle carrier 6 from the mating interlocking member 19 on the front plug 2. (In the exemplary embodiment described above, the handle moves in a counterclockwise direction as allowed by the triangular cutout 15 at the distal end of the slot 14 in the outer housing 1. Additional structural features of the actuator mechanism are shown in more detail in FIGS. 1-3.) When the handle 9 is released, the biasing element (here a compression spring 12) urges the needle carrier 6 and the slider 4 in the proximal direction, thus simultaneously withdrawing the access needle 8 and the safety guide wire 11 into the outer housing 1, leaving only the intravenous catheter 13 in the lumen of the vein. FIG. 8 shows the access needle 8 and the safety guide wire 11 withdrawing into the outer housing 1. The shape of the triangular cutout 15 allows the handle 9 to make a smooth transition into the elongated slot 14 as it moves proximally under the influence of the biasing element 12. Finally, the intravenous catheter 13 is disengaged from the luer slip 16 fitting on the distal end of the front plug 2, as shown in FIG. 9, and a source of intravenous fluid, a syringe or other device is attached to the luer fitting 27 of the intravenous catheter 13.

While it is desirable for the intravenous catheter insertion device 20 to withdraw the access needle 8 and the safety guide wire 11 simultaneously, the actuator mechanism could also be modified to withdraw the access needle 8 and the safety guide wire 11 sequentially. For example, the actuator mechanism could withdraw the access needle 8 first and then, after a slight delay, withdraw the safety guide wire 11.

Alternatively, the actuator mechanism could be modified to require two separate motions of one actuator member or selective movements of two separate actuator members to withdraw the access needle 8 and the safety guide wire 11 selectively.

In an alternative embodiment of the intravenous catheter insertion device 20, the compression spring 12 may be omitted from the actuator mechanism, thus allowing the access needle 8 and the safety guide wire 11 to be withdrawn manually using the handle 9. Once the intravenous catheter 13 has been inserted into the patient's vein, the handle 9 is rotated laterally to disengage the needle carrier 6 from the front plug 2, then the handle 9 is moved proximally along the slot 14 to withdraw the access needle 8 and the safety guide wire 11 into the outer housing 1.

The components of another embodiment of a catheter insertion device 20 are illustrated in FIGS. 10A and 10B. FIG. 10A illustrates a housing 1 having an interior space 34. The housing 1 is illustrated as a generally cylindrical container with sufficient strength to hold the various components of the catheter insertion device 20. Attachment feature 40 is also visible within interior space 34. As is illustrated in the figures that follow, attachment feature 40 may be used to secure the restraining element 36 to the handle 1 or within the interior space 34. An access needle 8 is positioned on and exits the interior space 34 at the distal end of housing 1. The access needle has a distal end 45 and a lumen 46. The access needle 8 is slideable with respect to the interior space 34. A release bar 32 is used to hold the needle 8 within the housing 1. In this illustrative embodiment, the biasing member 12 is compressed between the housing 1 and the needle support 29. A release button 30 is used to tilt the release bar 32 allowing the biasing member 12 to expand and move the access needle 8 proximally within the interior space.

The catheter insertion devices described herein include a biasing element adapted and configured that, when released, move the insertion needle from a position where at least a portion of the needle is outside of the housing 1 to a position within the interior space 34. Additionally, the same or a different biasing element is adapted and configured, when released, to move the guide wire 11 from a position outside of the housing to a position within the housing 1. In the configurations illustrated in many of the embodiments described herein distal movement of the needle 8 or guide wire 11 denotes insertion into a target vessel and proximal movement denotes withdrawal from a target vessel. Biasing elements are described using this convention for purposes of discussion. Other movements may be used for advancement into or withdrawal from and the descriptions of biasing element movement and configuration would be adjusted accordingly. In one aspect, a biasing element is adapted and configured that, when released from a constrained condition, moves the needle 8 so that the needle 8 is completely within the interior space 34. In another embodiment, a biasing element is adapted and configured to, when released from a constrained configuration, move the guide wire 11 so that the entire length of the guide wire 11 is completely within the interior space 34. In the embodiment illustrated in FIG. 11A, the biasing member 12 is a spring.

FIG. 10B illustrates the guide wire 11 and associated components. In the illustrated embodiment, the proximal end of the guide wire 11 is attached to a guide wire support 38. The distal end of the guide wire will, in use, extend along the access needle and beyond the distal end of the housing 1. Prior to use, one end of the guide wire 11 is always attached to the handle 1 or within the interior space 34 or both. After use, the guide wire 11 is completely within the handle 1 or within the interior space 34. The handle 9 is directly or indirectly attached to the guide wire. The handle 9 is moveable relative to the housing 1 to move the guide wire 11 relative to the interior space 34.

The guide wire support 38 and the guide wire 11 may be joined using any suitable technique. The guide wire support 38 is used to provide mechanical strength to the guide wire 11 since the guide wire 11 is a small diameter, flexible line, coil, filament or wire as described herein and well known in the medical arts. The guide wire support 38 may have a shape different that the illustrated embodiment and still meet the functional requirement of supporting one end of the guide wire 11. A handle 9 is attached, directly or indirectly to the guide wire 11 so that movement of the handle 9 produces movement of the guide wire 11 relative to the interior space 34 or the housing 1. In the illustrated embodiment, the handle 9 is attached to the guide wire 11 using the guide wire support 38. FIG. 10B also illustrates a restraining element 36. The restraining element 36 is used to prevent movement of the guide wire 11. In one aspect, the restraining element 36 attached to the handle 9 to limit the motion of the guide wire 11 relative to the access needle 8. In the illustrated embodiment, one end of the restraining element 36 is attached to the guide wire support 38. The other end or some other portion of the restraining element 36 is attached to the handle 1. In one embodiment, the restraining element extends between the guide wire support 38 or the handle 9 and the handle 1 or the interior space 34. The restraining element 36 may be attached to an attachment feature 40 or by any suitable means to the handle 1 or within interior space 34.

FIGS. 10C and 10D illustrate side views of catheter hub embodiments. FIG. 10D is a conventional catheter hub assembly 13. FIG. 10C is a catheter hub 13A with an angled base 61 to allow easier catheter entry into a vessel as will be further described below with regard to FIGS. 19A and 19B.

Figure 10E:
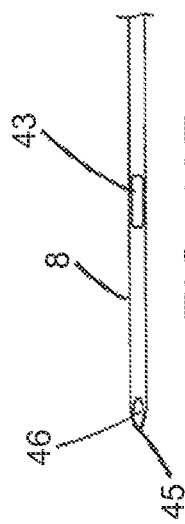
FIGS. 10E and 10F are top down views of an access needle having one bleed back indicator (FIG. 10E) or two bleed back indicators (FIG. 10F).
Figure 10F:
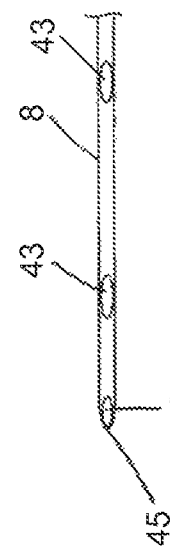

FIGS. 10E and 10F illustrate various apertures 43 in the access needle 8 to provide early indication of vessel puncture. FIG. 10E illustrates a single indicator opening 43 while FIG. 11F illustrates an embodiment with two indicators 43. The indicators 43 could have any suitable size and shape to provide indication that blood is present in the needle lumen 46. The illustrated shapes are rectangular in FIG. 10E and oval in FIG. 10F. Circular shapes could also be used.

Figure 10G:
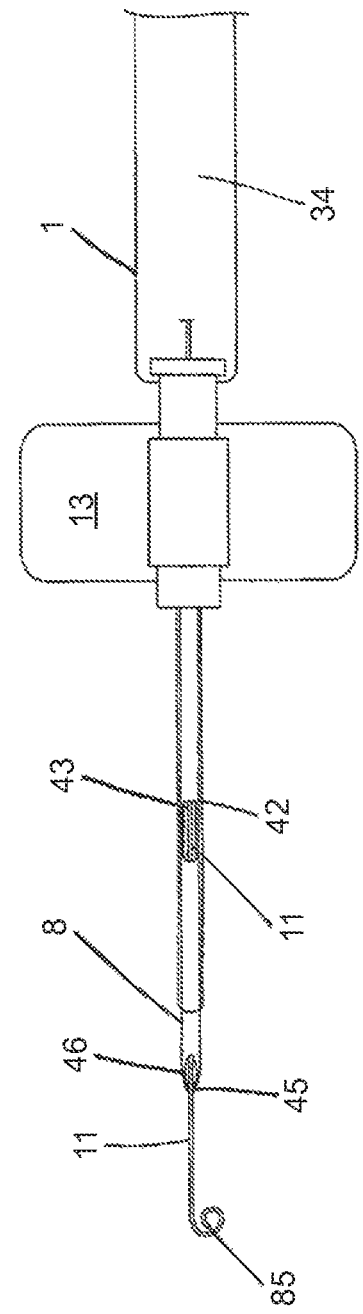
FIG. 10G is a top down view of a catheter insertion device inserted into a catheter.

FIG. 10G illustrates a top down view of a needle 6, guide wire 11 and the distal end of the handle 1 attached to a catheter hub 13. The length of needle 8 is selected to extend beyond the distal end of the catheter as shown. The needle distal end 45 extends far enough beyond the end of the catheter to allow for vessel puncture. The guide wire 11 is supported by and moveable relative to the access needle 8. The guide wire 11 is shown extended from the needle distal end 45.

The guide wire 11 coils into the plane of the page in this illustrated embodiment. The guide wire coil may be formed in the needle lumen 46 and advanced from the needle 8 in a coiled configuration or the guide wire 11 may be constrained into a straight configuration within the access needle lumen 46. Once extended out of the access needle lumen 46, the guide wire 11 assumes a previously defined coiled structure. In other embodiments, the guide wire 11 does not coil but instead remains straight during use. Various coil types are shown and described in FIGS. 1, 4A, 4B, 5B, 5A, 16A-17B, 22, 23 and 24.

The access needle 8 includes a bleed back indicator 42 visible in the distal end of a catheter 13 when the access needle 8 is positioned within a catheter 13. The bleed back indicator 43 in the illustrated embodiment includes an opening 43 in the sidewall of the distal end of the needle 8. The bleed back port 42 is visible through the catheter assembly 13 to provide a nearly immediate indication of vessel puncture. The bleed back indicator 42 is within a portion of the access needle 8 that extends beyond the housing 1. As illustrated, the bleed back indicator 42 is an opening 43 that is formed in the needle 8 in a portion of the needle that is distal to the distal end of the housing 1.

FIG. 10G also illustrates the relationship between the guide wire and the bleed back opening. One consideration in operating guide wire assisted access devices is inadvertent motion of the handle 9. If the handle 9 is advanced proximally, for example, the guide wire tip may pop out of the needle lumen 46 though the flash back channel 43. In this instance, the guide wire 11 would need to be re-threaded into the access needle lumen 46. FIGS. 11A and 11B illustrate one technique to prevent this undesired proximal movement using the restraining element 36. The restraining element 36 is used to restrict the movement of the guide wire 11. As best seen in FIG. 11A, the restraining element 36 is attached to the handle 9 and limits the proximal motion of the guide wire 11 relative to the access needle 8. The restraining element 36 is pulled tight and restricts further proximal movement of the handle 9. As shown, in the most proximal position prior to activation of the release button 30, the guide wire 11 remains within the access needle 8. In one embodiment, the restraining element 36 is a strip of Kevlar fabric cut to fit within the interior space 36. The restraining element 36 may be any of a wide variety of materials that will limit or prohibit the movement of the guide wire. The restraining element 36 could also be a flexible element that provides increasing resistance as the handle is moved to provide the user with a tactile feedback that the further movement of the handle in that direction is undesired.

Similar to FIGS. 7-9 above, FIGS. 11A-14B will be used to describe a illustrative catheter insertion sequence. The insertion of the catheter 13 and the operation of an embodiment of a catheter insertion device 20 will be described using a sequence of figures having a section view of the interior of the housing 1 and an illustration of the device being used to access a vessel.

FIG. 11A illustrates the housing 1 in position ready to use the needle to puncture a vessel. Note that the proximal movement of handle 9 is limited by the restraining device 36 so that the guide wire 11 remains in position within the interior space 34 and the needle lumen 46. FIG. 11B illustrates the device 20 inserted within a catheter 13 prior to vessel stick. FIG. 11C illustrates the needle 8 piercing through the vessel walls (vw) and into the vessel. Blood (B) appears in the bleed back indicator 42. Bleed back indicator 42 provides an early indication of vessel puncture. The guide wire 11 is maintained within the access needle lumen 46 between distal end of needle 45 and the bleed back opening 43.

Figure 12A:
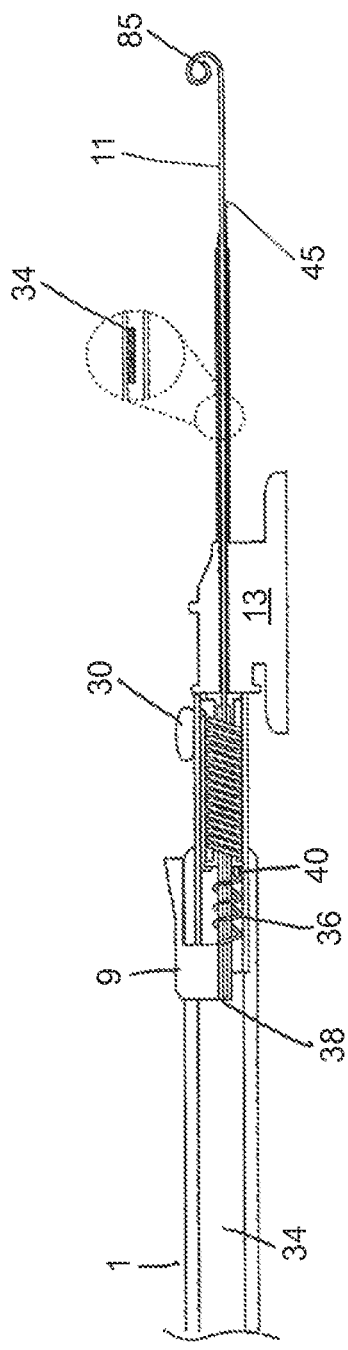
Figure 12B:
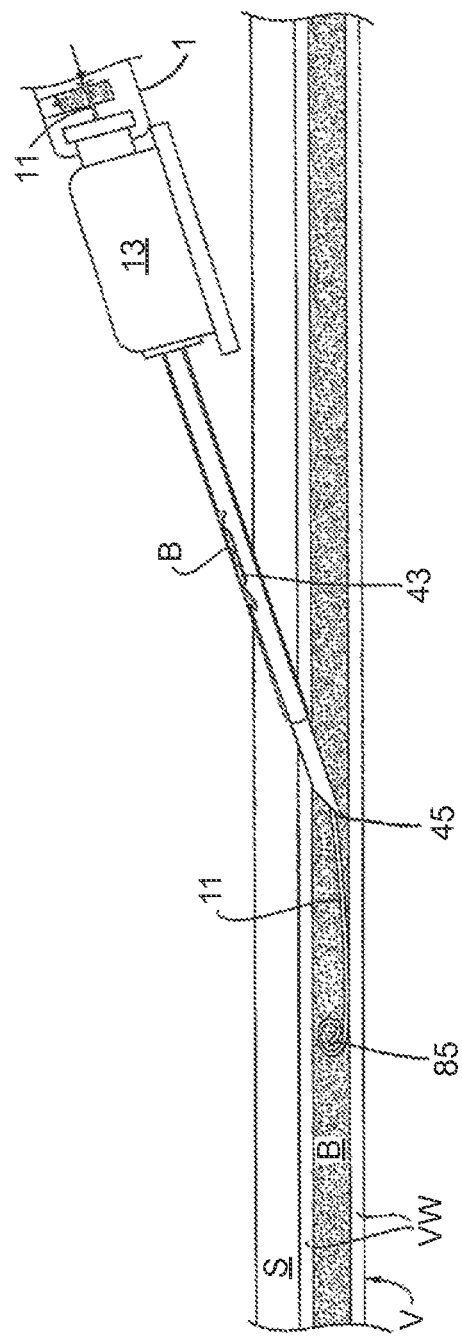

FIG. 12A illustrates the interior component position after guide wire advance. As shown, handle 9 has been moved distally relative to the housing 1. This movement advanced the guide wire 11 beyond the needle distal end 45 and reduced the tension in restraining element 36. FIG. 12B illustrates the guide wire 11 assuming a coiled shape after exiting the needle 8. Continued movement of the handle 9 advanced the guide wire 11 further into the vessel (v).

Figure 13C:
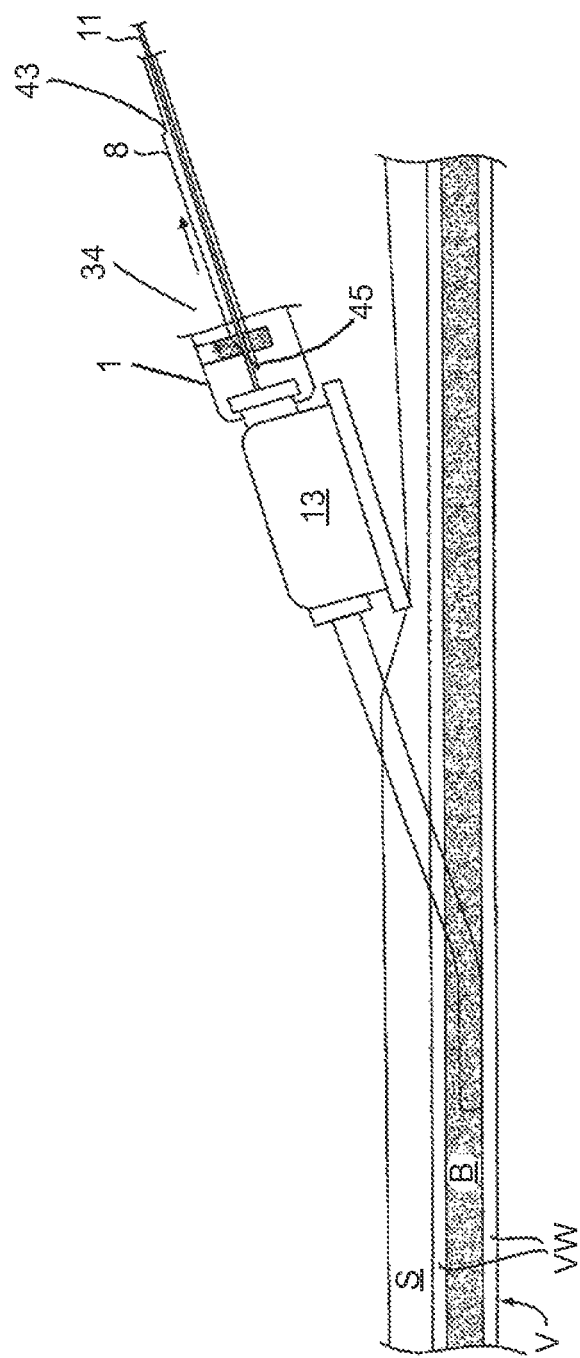

FIG. 13A illustrates the catheter 13 advanced beyond the needle distal end 45 and along the guide wire 11. Once the catheter is inserted into the vessel v, the guide wire 11 and access needle 8 can be withdrawn. Withdrawal of the guide wire 11 and needle 8 can occur in a wide variety of ways. Withdrawal may be simultaneous or sequential. If sequential, either the guide wire or the needle may be withdrawn first. Withdrawal may be performed by manual operation of a knob, handle, slider or other component attached directly or indirectly to either the guide wire 11, the needle 8 or to both the guide wire 11 and the needle 8. Withdrawal may also be performed using an automatic mechanism configured to withdraw on or both of the guide wire 11 and the needle 8. Automatic withdrawal of one element may be combined with manual withdrawal of the other element. Irrespective of withdrawal technique or sequence performed, a complete withdrawal sequence ends with both the needle and the guide wire proximal to the distal end of the housing 1 and/or within the interior space 34. In one aspect, at the conclusion of the withdrawal operation both the guide wire 11 and the needle 8 are completely within the interior space 38 so that sharp and blood exposed components are stowed within the housing 1. (see e.g., FIGS. 14A, 15 13C, 18G, and 31).

Figure 13D:
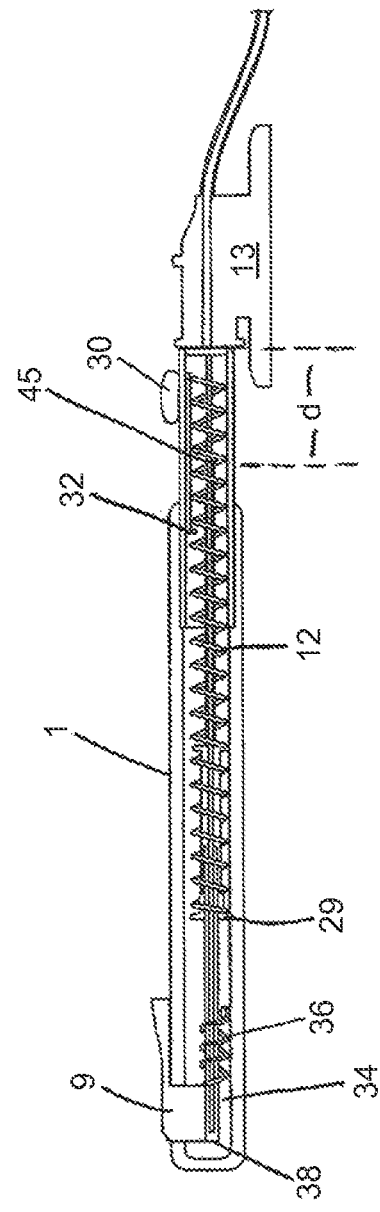

An automatic withdrawal sequence will be described beginning with FIG. 12A. The release button 30 is depressed so that the release bar 32 is lifted clear of the proximal end of needle support 29. The biasing member 12 is now unconstrained in the proximal direction and will expand that way. As the biasing member 12 moves proximally it will also move the needle support 29 proximally and along with it the needle 8. Proximal movement of the needle support 29 will also move the guide wire support 38 and handle 9 proximally along with the guide wire 11. FIG. 13B illustrates the proximal movement of the guide wire 11 shown near the distal end of the catheter 13 instead of further down the vessel as shown in FIG. 13A. FIG. 13C illustrates continued proximal movement indicated by the arrow. Here both the guide wire 11 and the needle 8 have been withdrawn from the catheter 13 and are now proximal to the distal end of housing 1. FIG. 13D is a section view of the housing 1 at the conclusion of the withdrawal sequence. At the conclusion of the withdrawal operation, the catheter 13 is inserted into the vessel v but the housing 1 is still attached to the catheter 13 as shown. The needle 8 and guide wire 11 are both proximal to the distal end of the housing 1 and within the interior space 34. Additionally, FIG. 13D illustrates both the guide wire 11 and the needle 8 completely within the housing 1 and interior space 34.

Figure 18G:
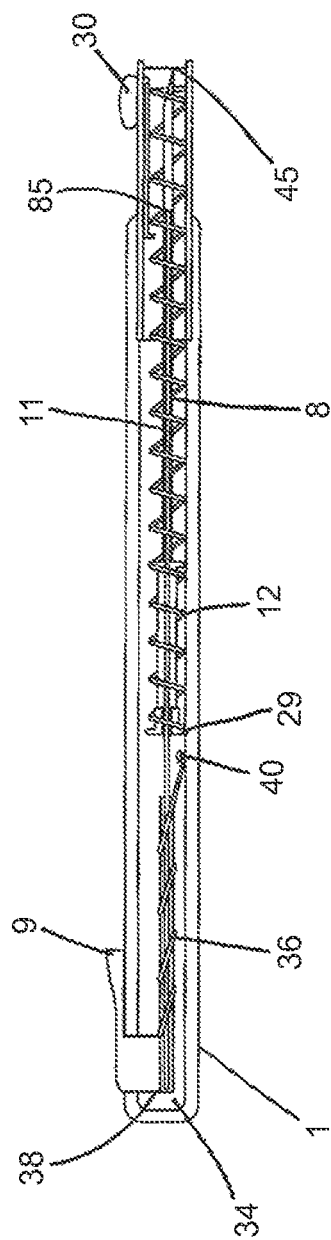

FIG. 14A illustrates the housing 1 disconnected from the catheter assembly 13. At this point, the housing 1 is ready for disposal and the catheter 13 is within the vessel as shown in FIG. 14B. As shown in FIGS. 14A and 15, the needle distal end 45 is withdrawn a distance d from the housing distal end 35. The needle 8 and the guide wire 11 are completely within the housing interior 34. The distance d may be adjusted based on a number of design factors such as the housing length, needle length, size of and energy stored in the biasing element, and the length of travel needed for withdrawal. The distance d may be from 1 mm to about 20 mm or may be just proximal to the housing distal end 35 as illustrated in FIG. 18G.

Returning to FIG. 14A, once the needle 8 and guide wire 11 are withdrawn into the housing 11, the blood exposed and sharp components of the device 20 typically the needle 8 and the guide wire 11, are within the handle interior space 34. This additional feature to provide additional security to ensure that the needle and the guide wire remain in the housing or within the interior space. In one aspect of the invention, a restraining element is positioned within the interior space 34 to limit distal movement of one or both of the access needle 8 or guide wire 11. The restraining device is positioned within the interior space based on the length of travel needed during a withdrawal sequence. The restraining element is, in some embodiments, positioned within the interior space 36 near the end of travel for the needle and/or guide wire. The end of travel for the needle and guide wire may vary with application. When positioned properly, the distal movement of the guide wire 11, the needle 8 or any component connected to the guide wire or the needle will be restricted so that neither the guide wire nor the needle will extend from the distal end of the housing 1. Alternatively, when positioned properly, the distal movement of the guide wire 11, the needle 8 or any component connected to the guide wire or the needle will be restricted so that the guide wire and the needle will remain within the interior space 34. The interior space 34 could be a cavity within the housing 1 or it could be the hollow space within housing 1.

In one embodiment, the restraining device restricts both proximal and distal movement. In another embodiment, the restraining device allows proximal movement but restricts distal movement. FIG. 15 illustrates one embodiment of a restraining device 64 within the interior space 34. The restraining device 64 has a truncated cone shape with the base opened towards the distal end of the housing 1. The restraining device is made of a flexible material with sufficient access to allow the one way proximal movement of the guide wire 11, needle 8 and the associated sub-components. In the illustrated embodiment, the restraining device is adapted and configured to seize on the proximal end of the needle support 29. The restraining device 29 could be configured to engage with, capture, confine or restrict any component in order to maintain the desired position of the guide wire and the needle. The restraining device 64 could also be a narrowing within the interior space 34 that produces a friction fit between the interior walls of the housing and the guide wire and/or needle components. In addition, the guide wire and needle components could be configured to engage and lock upon initiation of proximal movement of either the needle or the guide wire. In one embodiment, proximal movement locks the guide wire and the needle together such that they move as a single unit proximally within the housing 1. The restraining device 64 is then adapted and configured to engage with a feature on one of the guide wire or the needle or on the single guide wire/needle unit.

In another embodiment, the restraining device 64 includes one or more pins angled towards the proximal end of the interior space 34. Virtually any shape that will allow one way (here, proximal) passage of the needle/guide wire and prevent the opposite movement (here, distally) could be used. While illustrated as confining the movement of the needle guide, this is only for purposes of discussion. The retraining device could be adapted and configured to engage within any component of the needle or guide wire assemblies so long as the engagement allows withdrawal into the housing interior and prevents advancement out of the housing interior. Other restraining features and configurations include, for example, one or more rings, wedges, or any other friction lock configuration.

The guide wire 11 may have any of a number of different configurations including curved, coiled and straight configurations as shown and described in FIGS. 3, 4A, 4B, 5A-5C, 8, 22, 23 and 24 or in any other configuration conventional to field of guide wires for medical applications. In the illustrative embodiments of FIGS. 16A-17B, the guide wire 11 is coiled within the access needle lumen 46. FIGS. 16A-17B illustrate end views (FIGS. 16A and 17A) and isometric views (FIGS. 16B and 17B) of the distal portion of an embodiment of an access needle 8 used in a catheter insertion device 20. The illustrated access needles 8a and 8b have a distal end 45 and an interior wall defining a lumen 46 that extends from the distal end to a proximal end. As described above with access needle 8, the access needles 8a and 8b are slideable relative to the interior space 46 and extend beyond the distal end of the housing 1. An opening 43 in the sidewall of the access needles 8a, 8b is in communication with the access needle lumen 46. The opening 43 in the sidewall of the access needle is positioned proximal to the access needle distal end 45. A guide wire 11 is supported by the access needle.

The lumen of the access needles 8a, 8b have a cross section shape that maintains the orientation of the guide wire 11 relative to the access needle lumen 46. The access needles 8a, 8b illustrate access needle lumens having a non-circular cross section shapes. In one aspect, the shape of the access needle lumen is used to maintain the orientation of the guide wire to help prevent the guide wire from inadvertently exiting the access needle lumen through the bleed back indicator or opening 43. In the illustrative configurations of the FIGS. 16A-17B, if the guide wire 11 is withdrawn proximally into the area of the bleed back opening 43 then either a feature (FIGS. 16A and 16B) or the interior shape in the needle (FIGS. 17A and 17B) maintains the guide wire 11 in an orientation that will prevent the guide wire 11 from exiting the access needle lumen 46 via the opening 43. The orientation maintaining features illustrated in FIGS. 16A-17B may be used alone or in combination with each other. In another variation, an orientation maintaining feature may be used in combination with or in lieu of the restraining device 36 described and illustrated in FIGS. 10B and 11A.

In some embodiments, a feature formed within the access needle sidewall maintains the orientation of the guide wire 11 relative to the access needle lumen 46. The feature could be any formed on or in the sidewall or a separate component joined to the sidewall. FIGS. 16A and 16B illustrate a feature 52 formed within the access needle sidewall to maintain the orientation of the guide wire 11 relative to the access needle lumen. In the illustrated embodiment feature 52 is a groove formed along the sidewall. The depth of the groove is sufficient to confine the guide wire 11 and maintain its orientation within the needle lumen 46.

In the embodiment illustrated in FIGS. 17A and 17B, the cross section shape of the access needle lumen 46 is used to confine the guide wire 11 in the needle lumen 46 to prevent the guide wire 11 from exiting the lumen 46 through the bleed back opening 43. FIGS. 17A, 17B illustrate an access needle lumen 46 having an elliptical cross section shape. Other cross section shapes may be used to confine the guide wire 11 within the access needle lumen 46.

In one embodiment, the access needle lumen 46 confines the coiled guide wire 11 to form at least one half of a rotation within the access needle lumen 46. In an alternative embodiment, the access needle lumen confines the coiled guide wire 11 to form one or more rotations within the access needle lumen 46.

Another challenge related to the use of guide wire aided vessel access devices is the premature distal advancement of the guide wire during or prior to needle puncture. FIGS. 18A-18H illustrate an embodiment of a catheter insertion device 20 having a main channel 14 and a guide channel 70. The main channel 14 within the housing 1 confines the movement of the handle 9 along the housing 1. The guide channel 70 is adjacent to and accessible from the main channel 14. The guide channel 70 is adapted to prevent or restrict movement of the handle 9 once the handle 9 is in the guide channel 70.

The insertion device illustrated is used in an insertion sequence similar to the sequence described and illustrated above in FIGS. 7-9, and FIGS. 11A-14B. The components and operation of the catheter device 20 in FIGS. 18A-18H are similar to the embodiments described above and the same reference numbers are used on similar elements. The guide channel is an example of an additional feature to restrict or prevent distal movement of the guide wire 11. The housing 1 has a guide channel 70 in addition to the main channel 14. The guide channel 70 is best seen in the isometric view of FIG. 18B.

FIGS. 18A and 18B illustrate side and isometric views respectively of an embodiment of a catheter insertion device 20 with handle 9 in a proximal position in the main channel 14. This embodiment of the catheter insertion device 20 includes a housing 1 having an interior space 34. An access needle 8 is slideable with respect to the interior space 34 and extends from the distal end of the housing 1. A guide wire 11 is supported by and moveable relative to the access needle 8. A handle 9 is attached to the guide wire. The movement of the handle is limited so that at least a portion of the guide wire 11 always remains in the interior space 34. In the illustrated embodiment, the handle 9 is attached to the guide wire 11 using the guide wire support 38. The handle 9 and the guide wire support 38 could be a single component. As illustrated in the beginning of the sequence (FIG. 18A) and the end of the sequence (FIG. 18G) the movement of the handle 9 is confined so that the guide wire proximal portion 11A always remains in the interior space 34.

As shown in FIG. 18A, proximal movement of the handle 9 is restricted or stopped by the restraining device 36. As best seen in FIG. 18B, even though the handle 9 and the guide wire 11 are with drawn proximally, the guide wire 11 remains within the needle lumen 46 distal to opening 43 and proximal to distal end 45. In the embodiment illustrated in FIGS. 18A-18D the restraining element 36 prevents proximal guide wire movement and the holding channel 70, when used, prevents distal guide wire movement. One end of the guide wire 11 is secured to the housing 1 using attachment point 40. As shown in FIGS. 18A and 18B the guide wire 11 is disposed within the access needle 8.

Guide channel 70 may also include a friction or interference fit or otherwise restrict the handle 9 once the handle 9 is moved into the guide channel. For example, the guide channel may have a uniform width with a lock, tab or other feature in the distal end of the channel 70 to releasably secure the handle 9 within the channel 70. Alternatively, movement of the handle relative to the guide channel 70 may be used to lock and unlock the handle 9 from the guide channel 70. For example, the handle 9 may move into a J-shaped guide channel to lock and out of the j-shaped channel to return to the channel 14. In another alternative embodiment, the width of the guide channel 70 decreases distally to cause a friction with a distally advanced handle 9.

FIGS. 18C and 18D illustrate the handle 9 advanced distally into the guide channel 70. As compared to FIGS. 18A, 18B, the distal movement of the handle 9 produced corresponding distal movement of the guide wire 11. As best seen in FIG. 18D, the guide wire 11 is still within the access needle 8 and proximal to the distal end 45, the guide channel 70 is so designed that when the handle 9 is moved into the channel 70, the guide wire 11 remains within the needle 8. For those embodiments where the needle 8 includes an opening 43, the channel 70 confines the guide wire 11 movement between the opening 43 and the distal end of the needle 45.

FIGS. 18E and 18F illustrate guide wire advancement as described and illustrate above in FIGS. 8, 12A, and 13. FIGS. 18E and 18F also illustrate a catheter insertion device embodiment where one end of the guide wire 11 is constrained within the interior space 34 when the guide wire 11 is extended beyond the access needle distal end 45.

Figure 18H:
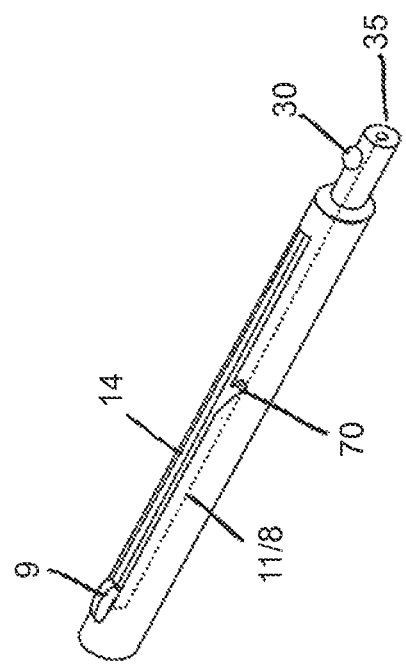

FIGS. 18G and 18H illustrate the position of the components at the conclusion of a withdrawal sequence as described and illustrated above with reference to FIGS. 9, 13A, 13B, 13C, 13D, 14 and 15. FIG. 18G illustrates the withdrawal of the needle distal end 45 to a position just proximal to the housing distal end 35. This final position is in contrast to FIGS. 14A and 15 where the needle distal end 45 is withdrawn a distance d from the housing distal end 35. The spatial relationship of the components used in this configuration may be altered so that the needle distal end may be withdrawn a distance d. In each of the embodiments described herein, the guide wire is withdrawn to the same position or proximal to the needle distal end 45, or at least proximal to the housing distal end 35 or a distance d as described.

FIGS. 18A-18D illustrate the restrictions on handle 9 movement provided by restraint device 36 and the guide channel 70. The catheter insertion device 20 may also be provided to a user in a "ready for use" configuration illustrated in FIGS. 18C and 18D. In this configuration, inadvertent distal guide wire 11 advancement is mitigated by the placement of the handle 9 in the guide channel 70. In order to advance the guide wire 11 distally or beyond the needle distal end 45, the handle 9 and guide wire 11 are moved proximally as needed to free the handle 9 from the guide channel 70. This proximal movement is limited by the restraining device 36 as shown in FIG. 18A to maintain the guide wire 11 in the needle 8. Thereafter, the handle 9 and guide wire 11 is advanced distally as described herein for catheter insertion followed by a needle/guide wire withdrawal sequence.

Another challenge facing vessel puncture or entry generally is providing an orientation of the catheter for patient comfort after insertion. One potential orientation issue is best illustrated in FIG. 14B. FIG. 14B illustrates a conventional catheter hub assembly 13 where the catheter lumen is bent down to accommodate the flat base and generally rectangular arrangement of the hub. In contrast, FIGS. 19A and 19B illustrate an angled catheter lumen. The catheter lumen angle Θ is selected to optimize the approach angle of the needle 8 for entering the vessel v. As shown in FIG. 19A, the housing 1 is aligned with the catheter lumen. As a result, the needle 8 is also aligned to the catheter lumen angle Θ. FIG. 19 is a section view of the catheter hub 13A illustrating catheter lumen angle Θ formed between the base 61 and the catheter lumen. In one embodiment, the catheter lumen angle Θ ranges from about 0 degrees to about 90 degrees. In another embodiment, the catheter lumen angle Θ ranges from about 0 degrees to less than about 25 degrees. The catheter 13A is used differently that the catheter hub 13. As shown in FIGS. 7 and 11C the housing and catheter unsupported above the vessel where the catheter base is not in contact with the skin. In contrast, when catheter 13A is used, base 61 is in contact the with skin and, when properly placed on the skin, the catheter lumen angle Θ may be used to guide the needle distal end 45 through the skin and into the vessel v. An angled catheter hub may increase patient comfort and reduce the possibility of catheters being inadvertently pulled out. These advantages result from the hub and lumen will be in better contact with the skin because catheter lumen is angled for insertion into the vessel.

Figure 20:
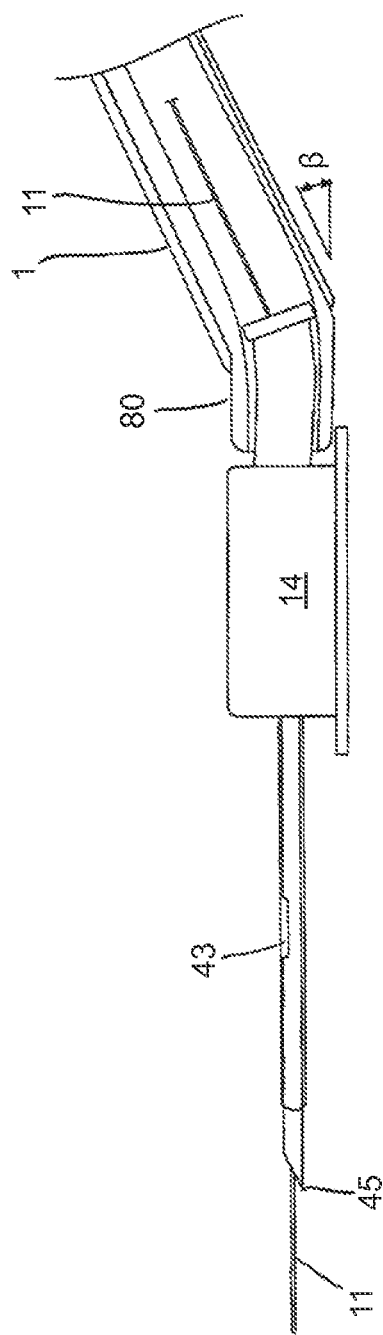
FIG. 20 is a side view of a catheter insertion device with a housing offset angle.

FIG. 20 illustrates an embodiment of a catheter insertion device having a housing 1 with an interior space 34 and a longitudinal axis. The feature 80 is positioned on or formed from the housing distal end 35. When the feature 80 is coupled to a catheter 13, the housing longitudinal axis is offset from the longitudinal axis of the catheter 13. The offset is indicated by the housing offset angle β. As illustrated, the housing offset angle β is about 10 degrees to about 15 degrees. In other embodiments, the housing offset angle β ranges from about 5 degrees to less than about 50 degrees. The access needle 8 passes through the feature 80 and is and attached to a needle carrier or other component within the housing 1. The needle and/or needle carrier is slideable with respect to the interior space 34 and the access needle 8 is slideable relative to the feature 80. In one embodiment, when the feature 80 is coupled to the catheter 13 the housing longitudinal axis is offset from the longitudinal axis of the catheter to form a housing offset angle β of less than 180 degrees. In another aspect, when the feature 80 is coupled to the catheter 13 the housing longitudinal axis is offset from the longitudinal axis of the catheter to form a housing offset angle β of less than 60 degrees. In another aspect, when the feature 80 is coupled to the catheter 13 the housing longitudinal axis is offset from the longitudinal axis of the catheter to form a housing offset angle β of less than 45 degrees. As a result of the offset angle β, the withdrawal sequence will produce needle and guide wire movement that it initially at an angle to the longitudinal axis of the housing and corresponding to the offset angle β. After passing through the feature 80, the withdrawal movement would change into a movement that is parallel and in some embodiments coextensive with the longitudinal axis of the housing 1. As such, once the guide wire and/or needle are withdrawn past the feature 80, the access needle and the guide wire are withdrawn into the interior space 34 substantially parallel to the longitudinal axis of the housing 1.

Another technique to adjust the angle of entry into the vessel and ease the use of the catheter insertion device involves altering the point where the needle exits the housing. It is believed that by moving the needle exit from the central portion of the housing as illustrated in the previous embodiments and conventional to safety syringes generally, a different access angle is formed between the housing 1 and the target vessel.

Figure 21:
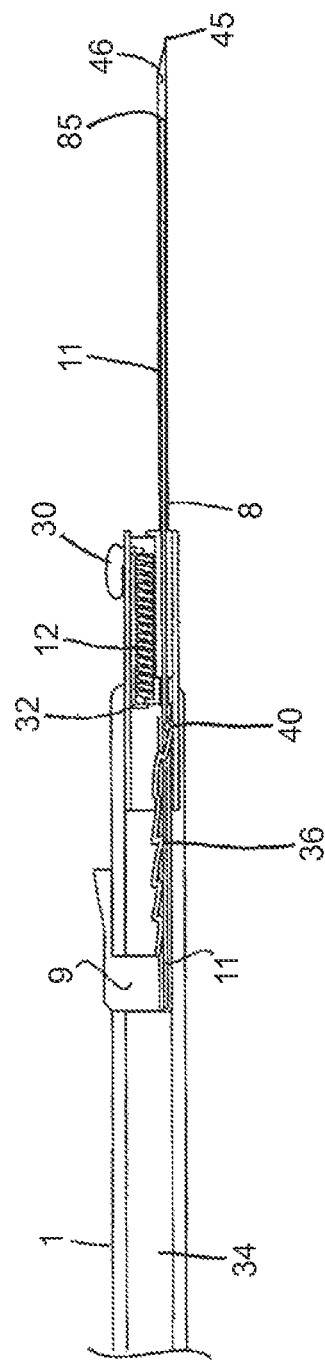
FIG. 21 is a section view of a catheter insertion device with an offset longitudinal axis.

FIG. 21 illustrates an embodiment of a catheter insertion device having a housing 1 with an interior space 34 and a longitudinal axis. The interior space 34 is sized and configured to contain all of the guide wire 11 and the access needle 8 after catheter insertion is complete. An access needle 8 is slideable with respect to the interior space 34. The needle axis is offset from the housing longitudinal axis. The offset needle is closer to one wall of the housing and exits the housing from a non-central portion of the housing distal end. Here, the needle axis extends parallel and below the housing longitudinal axis.

The biasing element 12 is coextensive with the housing axis. The release bar 32 is adapted to engage the needle support 21 where positioned towards one wall of the housing. Otherwise, the components operate as described above to needle and guide wire insertion and withdrawal.

In the illustrated embodiment, the longitudinal axis of the housing extends through the axis of the biasing element 12. The guide wire 11 is coextensive with the needle 8. The needle axis is parallel to but offset from the housing longitudinal axis. The biasing element 12 is above the needle 8 in contrast to previous embodiments where the needle and the biasing element were coextensive. Here the needle and guide wire may be moved closed to one wall of the housing. As a result, the needle exits the housing closer to one wall thereby allowing the housing to be held closer to the skin than in previous embodiments where the needle exited the housing in about the middle of the housing. In another aspect, the restraining element 36 and attachment point 40 may be moved above the needle to aid in moving the needle closer to one wall of the housing.

Various guide wire configurations are available as illustrated and described in, for example, FIGS. 1, 3, 4A, 4B, 5A, 5B, 5C, 8, 10B, 10G, and 16A-17B. Additional guide wire designs may also be used with the catheter insertion devices described herein. As illustrated and described herein, the guide wire 11 could be used in a coiled, uncoiled or curved configuration. In addition, the distal end of the second portion comprises one or more of a full radius distal tip, a spherical ball of the same material as the guide wire, a spherical ball of a different material than the guide wire or a distal end having a diameter about the same as the first diameter.

Figure 22:
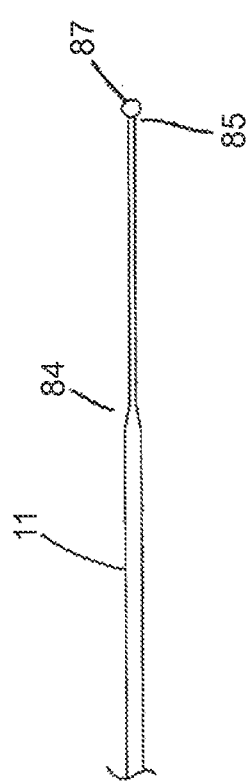
FIGS. 22, 23 and 24 illustrate guide wire alternatives.

FIG. 22 is a section view of a guide wire 11 having a first portion with a first diameter, a reducing section 84 and a second portion with a second diameter that is less than the first diameter. The guide wire distal end 85 is formed into a rounded tip 87 or a ball tip 87 is attached to distal end 85. The first diameter and the second diameter are less than the interior diameter of the access needle 8. In one embodiment, the first diameter is formed from 0.008 inch diameter wire and the second diameter is formed from 0.004 inch diameter wire having a full radius distal end 85. The transition or taper 84 is a linear change from the first diameter to the second diameter as illustrated. In one embodiment, the tip 87 is a spherical ball having a diameter between 0.005 and 0.012 inches formed with or a separate component attached to distal end 85. The spherical ball 87 may be formed from any metal, alloy, plastic, nitinol or other material suited for use in the body.

Figure 23:
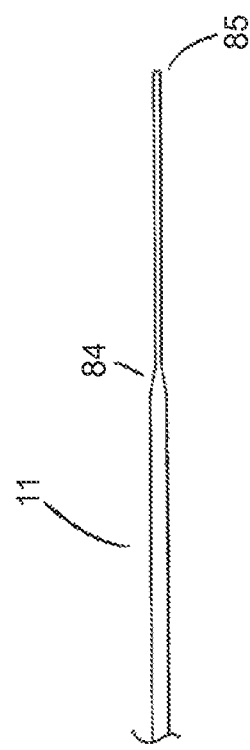

FIG. 23 is a section view of a guide wire 11 having a first portion with a first diameter, a reducing section 84 and a second portion with a second diameter that is less than the first diameter. The guide wire distal end 85 is formed into a rounded end. The first diameter and the second diameter are less than the interior diameter of the access needle 8. In one embodiment, the first diameter is formed from 0.008 inch diameter wire and the second diameter is formed from 0.004 inch diameter wire having a full radius distal end 85. The transition or taper 84 is a linear change from the first diameter to the second diameter as illustrated. In an alternative embodiment, the transition segment 84 is removed and the guide wire has a single diameter from proximal to distal end. In one specific embodiment, the wire used for the guide wire has a diameter of 0.006 inches.

Figure 24:
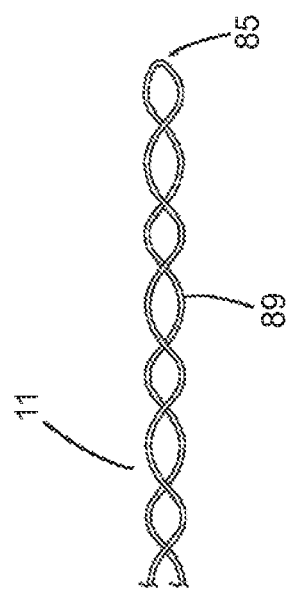

FIG. 24 illustrates a guide wire 11 formed in a braided structure 89.

In one exemplary embodiment, the braided structure 89 is formed from nitinol wore having a 0.002 inch diameter.

Figure 25A:
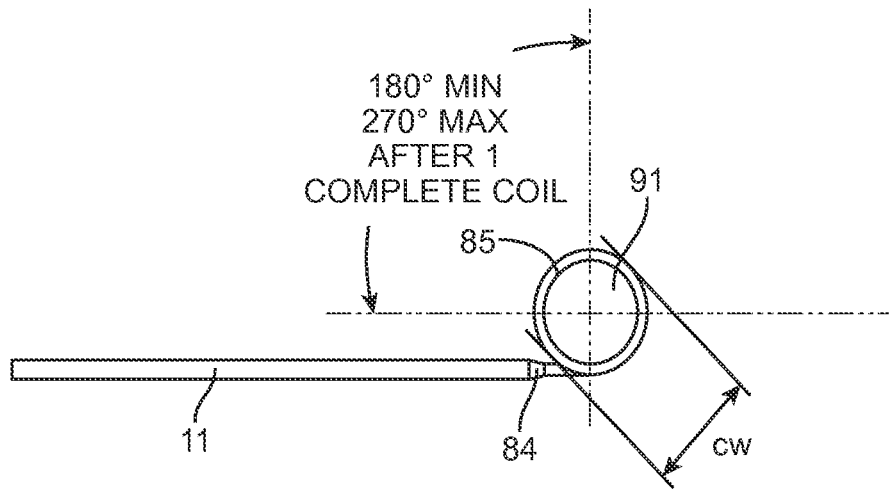
FIGS. 25A and 25B illustrate side and end views, respectively, of a coiled portion of a guide wire.
Figure 25B:
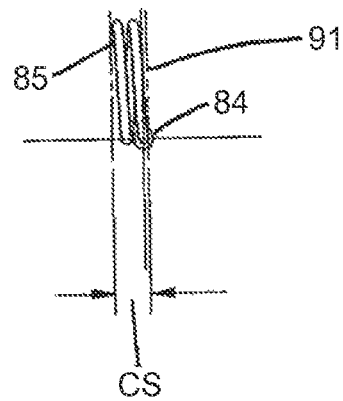

FIGS. 25A and 25B illustrate one embodiment of a guide wire 11 having a coiled portion 91. FIG. 25A is a side view of the guide wire 11 having a first diameter region, a taper or transition region 84 and a second diameter region formed into a coiled portion 91. The coil portion 91 may be described in terms of coil width (cw) and coil span (sc). Coil width (cw) is best seen in FIG. 25A. Coil span (cs) is best seen in FIG. 25B. In one embodiment, the distal tip 85 moves through an angular displacement of at least 180 degrees when moving from a straight configuration (FIG. 23) to a coiled configuration (FIG. 25A). In another embodiment, the distal tip 85 moves through an angular displacement of no more than 270 degrees when moving from a straight configuration (FIG. 23) to a coiled configuration (FIG. 25A). In another embodiment, the coiled portion 91 includes at least one completely formed coil. In another embodiment, the coil width is from about 0.04 to about 0.05 inches. In another embodiment, the coil span is less than 0.015 inches.

FIGS. 26A and 26B illustrate section views of a catheter insertion device embodiment similar in many aspects to the device illustrated and described above in FIGS. 10A, 10B and 11A. FIG. 6 utilizes a spring loaded drum 24 to provide a mechanism to ensure complete withdrawal of the guide wire 11 into the housing 1 when the length of guide wire 11 used exceeds the length of the housing. Along the same lines as FIG. 6, FIGS. 26A and 26B illustrate a catheter insertion device that also provides a mechanism to withdraw a length of guide wire 11 longer than the length of the housing 1.

FIGS. 26A and 26B illustrate an embodiment of a catheter insertion device with a pulley 98 secured within the interior space 34. The pulley 98 is configured to facilitate movement of the guide wire 11 into the interior space 34. FIG. 26A illustrates another catheter insertion device embodiment where one end of guide wire is constrained in the interior space when the guide wire is advanced beyond the needle distal end 45.

The housing interior 34 is dimensioned to store more guide wire but in a manner that accounts for the fact that the guide wire to be retrieved is longer than the housing 1 and at the conclusion of the withdrawal operation sequence, all of the guide wire 11 is within the housing 1. The guide wire 11 passes around the pulley 98 and is attached to the housing at attachment 40a. The biasing member 12a replaces the biasing element 12. The biasing member 12a is extended as the guide wire 11 is advanced distally as shown in FIG. 26A. When released, the pulley 98 moves proximally within the housing 1 as shown in FIG. 26B. The proximal movement of the pulley is the motive force for a withdrawal sequence used to withdraw the needle 8 and guide wire 11 as described above. The reference numbers used correspond to components described above that perform similar functions in this embodiment.

FIGS. 27A-27E illustrate several section views of the distal end of an access needle 8 configured for use with a guide wire channel 54. In these embodiments, the guide wire channel 54 is supported by the access needle 8. In one embodiment, the guide wire channel 54 is suitably dimensioned needle that is attached to the access needle 8 using any suitable joining or bonding technique. The guide wire channel diameter is less than half the size of the access needle diameter in some embodiments. In other embodiments the guide wire channel diameter ranges from 0.016 inches to about 0.028 inches. In other embodiments, the access needle is a standard size, commercially available needle and the guide wire channel is also a standard size, commercially available larger gauge needle. For example, if the access needle is a standard 17 gauge needle (0.058" diameter) then the guide wire channel may be any larger gauge needle such as 18 gauge to 27 gauge. In other embodiments, the guide wire channel is a standard, gauge needle selected to accommodate the guide wire 11. For example, a 27-20 gauge needle (diameters ranging from 0.016-0.035 inches) may be used for a guide wire diameter of 0.008 inches depending upon desired amount of clearance. In other configurations the guide wire channel inner diameter is about twice the diameter of the guide wire in the channel 54.

In the embodiments that follow, the side of the needle having distal end 45 will denote the bottom of the needle and the side opposite that surface as the top of the needle. FIG. 27A illustrates an embodiment where the guide wire channel 54 is on top of the needle 8. The guide wire 11 remains in the guide wire channel 54. In this embodiment, the guide wire may be advanced proximally and distally without passing through or within the access needle lumen 46.

FIG. 27B illustrates an embodiment where the guide wire channel 54 is on the bottom of the needle 8. The guide wire 11 remains in the guide wire channel 54. In this embodiment, the guide wire may be advanced proximally and distally without passing through or within the access needle lumen 46. FIG. 27B1 illustrates an alternative embodiment where the guide channel 54 is a needle with a distal tip 57 positioned adjacent the access needle distal tip 45.

FIG. 27C illustrates an embodiment where the guide wire channel 54 is on the top of the needle 8 inside the needle lumen 45. In this embodiment, the length of guide wire channel 54 is less than the length of the access needle lumen. The access needle includes a port 58 in the needle sidewall distal to the end of the guide wire channel and proximal to the distal end of the needle. The guide wire passes out the end of the guide wire channel through the port 58 and into the vessel. The guide wire 11 remains in the guide wire channel 54 for most of the length of the access needle lumen.

FIG. 27D illustrates an embodiment where the guide wire channel 54 is on the top of the needle 8. In this embodiment, the length of guide wire channel 54 is less than the length of the access needle lumen. The access needle includes a port 58 in the needle sidewall at the end of the guide wire channel and proximal to the distal end of the needle. The guide wire passes out the end of the guide wire channel through the port 58 and into the access needle lumen 46. The guide wire 11 remains in the guide wire channel 54 for most of the length of the access needle lumen.

FIG. 27E illustrates an embodiment where the guide wire channel 54 is on the top of the needle 8 inside the needle lumen 45. In contrast to FIG. 27C, the access needle does not include a port 58 in the needle sidewall. As with FIG. 27C, the length of guide wire channel 54 is less than the length of the access needle lumen. However, instead of exiting the needle lumen, the distal to the end of the guide wire channel opens into the needle lumen proximal to the distal end of the access needle. The guide wire passes out the end of the guide wire channel passes through the distal end of the needle lumen and hence into the vessel v. As with the previous embodiments, the guide wire 11 remains in the guide wire channel 54 for most of the length of the access needle lumen but does not exit the guide channel and enter the vessel directly as with the embodiments of FIGS. 27A, 27B and 27B1.

While described as using a single button to automatically withdraw both the guide wire and the needle with a single action, one of the guide wire or the needle may be withdrawn from the vessel manually. In another alternative, both the guide wire and the needle are withdrawn manually. In one aspect of this embodiment, the biasing element 12 illustrated in FIG. 10A may be removed and the needle support 29 attached to a second handle. In this embodiment, needle withdrawal is accomplished by moving the second slider attached to the needle proximally until the needle is within the housing interior 34. In addition, the device may be adapted so that the handle 9 may be used to manually withdrawn the guide wire separately or in sequence with the needle withdrawal.

The above described catheter insertion devices may be used to perform a number of different methods of introducing a catheter into a vessel. One exemplary basic method includes three steps. First, insert a guide wire substantially contained within a housing into a vessel. Next, advance a catheter over the guide wire and into the vessel. Finally, withdrawing the guide wire out of the vessel and completely into the housing.

The basic method may include other steps. In one alternative, the guide wire is advanced along and within a needle inserted into the vessel before performing the inserting step. In another alternative, the guide wire is advanced along and outside a needle inserted into the vessel before performing the inserting step. In yet another alternative, the guide wire is advanced within a guide wire channel before entering the vessel. In yet another aspect, the guide wire is coiled within the vessel after the inserting step, while in the access needle or after exiting a guide wire channel.

Other alternative or modified method steps may also be performed. In one aspect, the withdrawing step is accomplished manually and in another embodiment withdrawal occurs automatically. In one alternative, the withdrawing step is accomplished by releasing a biasing member to withdraw the guide wire completely into the housing. In another aspect, releasing a biasing member also withdraws a needle supporting the guide wire completely into the housing. In one alternative, the withdrawing step or a withdrawal sequence is initiated by pushing a button. In an additional aspect, a step of inserting a needle attached to the housing into the vessel is performed before the step of inserting a guide wire step. One additional optional step includes using a flashback indicator near the distal tip of the needle to determine that the needle has entered the vessel after the inserting a needle step. In another aspect, the method may include the step of moving a handle attached to the guide wire proximally before the inserting step.

Each of the patent application, patents and references mentioned in this application are incorporated herein by reference in it's entirely. Additionally, each of U.S. Pat. Nos. 4,747,831; 4,509,945; 4,900,307; and 5,749,371 are incorporated herein by reference in its entirety.

While the present invention has been described herein with respect to the exemplary embodiments and the best mode for practicing the invention, it will be apparent to one of ordinary skill in the art that many modifications, improvements and sub-combinations of the various embodiments, adaptations and variations can be made to the invention without departing from the spirit and scope thereof. For example, all dimensions and materials included in the specification or drawings are intended only as examples of presently preferred embodiments and are not intended to limit the scope of the invention.

What is claimed is:

1. A catheter insertion device, comprising:
   a housing;
   a needle having a proximal end in the housing and a distal end extending from a distal end of the housing in an insertion position;
   a guide wire having a distal portion disposed in a lumen of the needle in a withdrawn position, the guide wire including a safety tip having a non-coiled configuration in the withdrawn position and a coiled configuration in an advanced position, the coiled configuration comprising a preformed spiral including a plurality of revolutions, the plurality of revolutions including adjacent revolutions in different planes;
   a sliding member attached to the guide wire, wherein movement of the sliding member translates the guide wire from the withdrawn position to the advanced position; and
   a catheter disposed coaxially over the needle.

2. The catheter insertion device according to claim 1, wherein the needle comprises a side wall opening, and wherein a distal end of the guide wire is distal of the side wall opening in the withdrawn position.

3. The catheter insertion device according to claim 1, wherein the guide wire has a first portion having a first diameter and a second portion having a second diameter less than the first diameter, and wherein the safety tip is formed in the second portion.

4. The catheter insertion device according to claim 1, wherein the guide wire is formed from a superelastic Nickel-Titanium alloy.

5. The catheter insertion device according to claim 1, wherein the catheter includes a tapered distal end disposed proximally of a tip of the needle in the insertion position.

6. The catheter insertion device according to claim 1, further comprising a support tube disposed over a proximal portion of the guide wire.

7. The catheter insertion device according to claim 6, wherein a proximal end of the guide wire is attached to the support tube.

* * * * *